US006833371B2

(12) United States Patent
Atkinson et al.

(10) Patent No.: US 6,833,371 B2
(45) Date of Patent: Dec. 21, 2004

(54) PYRAZOLOPYRIMIDINES

(75) Inventors: Robert N. Atkinson, Raleigh, NC (US); Michael F. Gross, Durham, NC (US); Albert M. van Rhee, Durham, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 10/286,687

(22) Filed: Nov. 1, 2002

(65) Prior Publication Data

US 2003/0176450 A1 Sep. 18, 2003

Related U.S. Application Data

(60) Provisional application No. 60/335,874, filed on Nov. 1, 2001.

(51) Int. Cl.[7] .............................................. A61K 31/519
(52) U.S. Cl. ................. 514/259.3; 514/259.1; 514/259.2; 514/256
(58) Field of Search ........................ 514/259.3, 259.1, 514/259.2, 256

(56) References Cited

U.S. PATENT DOCUMENTS 4,178,449 A * 12/1979 Dusza et al. ................ 544/281
5,571,813 A    11/1996 Ruhter et al.

* cited by examiner

*Primary Examiner*—Dwayne Jones
(74) *Attorney, Agent, or Firm*—Townsend and Townsend and Crew LLP

(57) ABSTRACT

Compounds, compositions and methods are provided which are useful in the treatment of diseases through the inhibition of sodium ion flux through voltage-dependent sodium channels. More particularly, the invention provides pyrazolopyrimidines, compositions and methods that are useful in the treatment of central or peripheral nervous system disorders, particularly pain and chronic pain by blocking sodium channels associated with the onset or recurrance of the indicated conditions. The compounds, compositions and methods of the present invention are of particular use for treating neuropathic or inflammatory pain by the inhibition of ion flux through a channel that includes a PN3 subunit.

8 Claims, No Drawings

PYRAZOLOPYRIMIDINES

CROSS-REFERENCES TO RELATED APPLICATIONS

This application claims priority to U.S. Provisional Patent Application No. 60/335,874 filed Nov. 1, 2001, which is incorporated herein by reference in its entirety for all purposes.

FIELD OF THE INVENTION

This invention relates to the use of certain pyrazolopyrimidine compounds as sodium channel inhibitors and to the treatment of neuropathic pain by the inhibition of sodium channels. Additionally, this invention relates to novel pyrazolopyrimidine-based compounds that are useful as sodium channel inhibitors.

BACKGROUND OF THE INVENTION

Sodium channel-blocking agents have been reported to be effective in the treatment of various disease states, and have found particular use as local anesthetics and in the treatment of cardiac arrhythmias. It has also been reported that sodium channel-blocking agents may also be useful in the treatment of pain, including neuropathic pain; see, for example, Tanelian et al. *Pain Forum.* 4(2), 75–80 (1995). Preclinical evidence demonstrates that sodium channel-blocking agents selectively suppress abnormal ectopic neural firing in injured peripheral and central neurons, and it is via this mechanism that they are believed to be useful for relieving pain. Consistent with this hypothesis, it has been shown that sodium channels accumulate in the peripheral nerve at sites of axonal injury (Devor et al. *J. Neurosci.* 132: 1976 (1993)). Alterations in either the level of expression or distribution of sodium channels within an injured nerve, therefore, have a major influence on the pathophysiology of pain associated with this type of trauma.

An increasing body of evidence suggests that a voltage-dependent, tetrodotoxin (TTX)-resistant Na channel, PN3 ($Na_v 1.8$), may play a key role in sensitization in neuropathic pain states. Neuropathic pain can be described as pain associated with damage or permanent alteration of the peripheral or central nervous system. Clinical manifestations of neuropathic pain include a sensation of burning or electric shock, feelings of bodily distortion, allodynia and hyperalgesia.

PN3 is a member of a family of voltage-gated sodium channel alpha subunits. Names for this family include SCN, SCNA, and $Na_v x.x$. There are currently 10 known members falling into two subfamilies $Na_v 1$ (all but SCN6A) and $Na_v 2$ (SCN6A). The human channel was cloned by Rabert et al. (*Pain* 78(2): 107–114 (1998)). PN3 of other species has also been cloned. See, for example, Chen et al., *Gene* 202(1–2), 7–14 (1997); Souslova et al., *Genomics* 41(2), 201–209 (1997); Akopian et al., *Nature* 379(6562), 257–262 (1996).

PN3-null mutant mice exhibit a pronounced analgesia to mechanical noxious stimuli (Akopian A. N. et al., *Nature Neurosci.*, 2(6): 541–548 (1999)). Selective "knock down" of PN3 protein in the rat dorsal root ganglion with specific antisense oligodeoxynucleotides prevents hyperalgesia and allodynia caused by either chronic nerve or tissue injury (Porreca et al., *Proc. Nat. Acad. Sci., USA*, 96: 7640–7644 (1999)). The biophysical properties of PN3 make it ideally suited to sustain repetitive firing of sensory neurons at the depolarized potentials characteristic of injured peripheral nerves. In both human and animal models of neuropathic pain, there is an increased expression of PN3 at the site of peripheral nerve injury (Clare et al., *DDT* 5: 506–519 (2000); Coward et al., *Pain* 85: 41–50 (2000)).

Patients with neuropathic pain do not respond to non-steroidal anti-inflammatory drugs (NSAIDS) and resistance or insensitivity to opiates is common. Most other treatments have limited efficacy or undesirable side effects. Mannion et al., *Lancet*, 353: 1959–1964 (1999) from the Department of Anesthesia and Critical Care, Massachusetts General Hospital and Harvard Medical School wrote: "There is no treatment to prevent the development of neuropathic pain, nor to adequately, predictably and specifically control established neuropathic pain."

PN3 is a promising molecular target for the treatment of neuropathic pain. One of the most attractive features of PN3 is the highly restricted and peripheral nature of its expression. Antisense studies have revealed no overt (particularly CNS-related) adverse effects, consistent with the localized, peripheral distribution of the channel (Novakovic et al., *J. Neurosci.*, 18(6): 2174–2187 (1998)). Additionally, the high activation threshold of PN3 suggests that the channel may be relatively uninvolved in normal nociception. These properties of PN3 present the possibility that selective blockade of this particular voltage-gated sodium channel (VGSC) may offer effective pain relief without the significant side effect liability normally associated with more promiscuous VGSC blocking drugs. The compounds of the invention are potent inhibitors of PN3 channels.

Ohkawa et al. have described a class of cyclic ethers that are of use as sodium channel blockers (U.S. Pat. No. 6,172,085).

Currently, gabapentin is the market leading treatment for neuropathic pain. As with epilepsy, its mechanism of action for pain is unknown. It is a very safe, easy to use drug, which contributes to its sales. Efficacy for neuropathic pain is not impressive, as few as only 30% of patients respond to gabapentin treatment. Carbamazepine is also used to treat neuropathic pain.

In view of the limited number of agents presently available and the low levels of efficacy of the available agents, there is a pressing need for compounds that are potent, specific inhibitors of ion channels implicated in neuropathic pain. The present invention provides such compounds, methods of using them, and compositions that include the compounds.

SUMMARY OF THE INVENTION

It has now been discovered that pyrazolopyrimidines are potent inhibitors of sodium channels. In the discussion that follows, the invention is exemplified by reference to the inhibition of sodium channels that are localized in the peripheral nervous system, and in particular those inhibitors that are selective inhibitors of PN3, and are useful for treating neuropathic pain through the inhibition of sodium ion flux through channels that include the PN3 subunit. The focus of the discussion is for clarity of illustration only.

The compounds and methods of the present invention are useful for treating diseases in which blocking or inhibiting one or more PN3 ion channel provides relief from the disease. Of particular interest is the use of the compounds and methods of the invention for treating pain and central or peripheral nervous system disorders. The present invention is of use for treating both inflammatory and neuropathic pain.

The present invention provides compounds which are useful in the treatment of diseases through the inhibition of sodium ion flux through voltage-dependent sodium channels. More particularly, the invention provides compounds, compositions and methods that are useful in the treatment of central or peripheral nervous system disorders, particularly pain and chronic pain.

In one aspect, the present invention provides compounds according to Formula I:

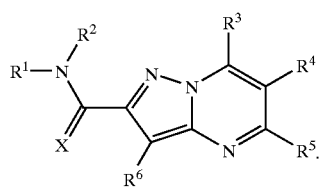

(I)

In Formula I, $R^1$ represents substituted or unsubstituted alkyl, substituted or unsubstituted aryl, substituted or unsubstituted heteroaryl, substituted or unsubstituted heterocycloalkyl, and substituted or unsubstituted aryl (alkyl). $R^2$ is a member selected from hydrogen and substituted or unsubstituted alkyl. $R^1$ and $R^2$ taken together with the nitrogen atom to which they are optionally joined to form a 4- to 8-membered heterocycloaryl ring. The symbol $R^3$ represents a member selected from hydrogen, substituted or unsubstituted alkyl, halo, amino, substituted or unsubstituted aryl, substituted or unsubstituted heteroaryl and substituted or unsubstituted heterocycloalkyl. The symbol $R^4$ represents a member selected from hydrogen, halo, substituted or unsubstituted alkyl and substituted or unsubstituted aryl. $R^5$ is a member selected from substituted or unsubstituted alkyl, substituted or unsubstituted aryl, substituted or unsubstituted heteroaryl and substituted or unsubstituted heterocycloalkyl. $R^6$ is a member selected from hydrogen, halo, substituted or unsubstituted aryl, substituted or unsubstituted heteroaryl, and substituted or unsubstituted heterocycloalkyl. X is either O or S.

In another aspect, the present invention provides pharmaceutical compositions comprising a pharmaceutically acceptable excipient and a compound provided above.

In yet another aspect, the present invention provides a method for inhibiting ion flux through voltage dependent sodium channels, comprising contacting a cell containing the target ion channels with a compound of the formula provided above.

In still another aspect, the present invention provides a method for the treatment of diseases through inhibition of ion flux through voltage dependent sodium channels, the method comprising treating the host with an effective amount of a sodium channel inhibiting compound of the formula provided above.

Other objects, advantages and embodiments of the invention will be apparent from review of the detailed description that follows.

DETAILED DESCRIPTION OF THE INVENTION AND THE PREFERRED EMBODIMENTS

Abbreviations and Definitions:

The abbreviations used herein have their conventional meaning within the chemical and biological arts. For example: CHO, Chinese hamster ovary; EBSS, Earl's Balanced Salt Solution; SDS, sodium dodecyl sulfate; $Et_3N$, triethylamine; MeOH, methanol; and DMSO, dimethylsulfoxide.

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., *Harrison's Principles of Internal Medicine*, pp. 93–98 (Wilson et al., eds., 12th ed. 1991); Williams et al., *J. of Medicinal Chem.* 42:1481–1485 (1999), herein each incorporated by reference in their entirety).

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic" pain, as described above, refers to pain resulting from injury to or chronic changes in peripheral and/or central sensory pathways, where the pain often occurs or persists without an obvious noxious input.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Compound of the invention," as used herein refers to the compounds discussed herein, pharmaceutically acceptable salts and prodrugs of these compounds.

"Inhibiting" and "blocking," are used interchangeably herein to refer to the partial or full blockade of a PN3 channel by a compound of the invention, which leads to a decrease in ion flux either into or out of a cell in which a PN3 channel is found.

Where substituent groups are specified by their conventional chemical formulae, written from left to right, they equally encompass the chemically identical substituents which would result from writing the structure from right to left, e.g., —$CH_2O$— is intended to also recite —$OCH_2$—; —$NHS(O)_2$— is also intended to represent. —$S(O)_2HN$—, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo (C$_1$–C$_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: -hydrogen, —OR', =O, =NR''', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR''', —C(O)NR'R'', —NR'C(O)$_2$R', —NR'''—C(NR'R'')=NR''', —NR'''—C(NR'R'')=NR''', —S(O)R', —S(O)$_2$R', —S(O)$_2$NR'R'', —NR'SO$_2$R'', —NR'''SO$_2$NR'R'' —CN, —R' and —NO$_2$ in a number ranging from zero to (2m'+1), where m' is the total number of carbon atoms in such radical. R', R'', R''' each preferably independently refer to hydrogen, substituted or unsubstituted alkyl, substituted or unsubstituted heteroalkyl, substituted or unsubstituted aryl, (e.g., aryl substituted with 1–3 halogens, substituted or unsubstituted alkyl, alkoxy or thioalkoxy groups), substituted or unsubstituted heteroaryl and substituted or unsubstituted arylalkyl. R'''' refers to hydrogen, alkyl, substituted or unsubstituted heteroalkyl, substituted or unsubstituted aryl, substituted or unsubstituted heteroaryl, substituted or unsubstituted arylalkyl, —CN, —NO$_2$ and —S(O)$_2$R'. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl, 1-piperidinyl, 1-piperazinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: hydrogen, —OR', —C=NR""NR'R", —NR'''SO$_2$NR'R", —NR'R", —SR', -halogen, —SiR"R"', —OC(O)R', —C(O)R', —CO$_2$R', —CONR'R", —OC(O)NR'R", —NR"C(O)R', —NR'''—C(O)NR'R", —NR"C(O)$_2$R', —NR'''—C(NR'R")=NR"", —S(O)R', —S(O)$_2$R', —S(O)$_2$NR'R", —NR"SO$_2$R', —CN and —NO$_2$, —R', —N$_3$, —CH(Ph)$_2$, fluoro(C$_1$–C$_4$)alkoxy, and fluoro(C$_1$–C$_4$) alkyl, in a number ranging from zero to the total number of open valences on the aromatic ring system; and where R', R" and R''' each preferably independently refer to hydrogen, substituted or unsubstituted alkyl, substituted or unsubstituted heteroalkyl, substituted or unsubstituted aryl, (e.g., aryl substituted with 1–3 halogens, substituted or unsubstituted alkyl, alkoxy or thioalkoxy groups), substituted or unsubstituted heteroaryl and substituted or unsubstituted arylalkyl. R"" refers to hydrogen, alkyl, substituted or unsubstituted heteroalkyl, substituted or unsubstituted aryl, substituted or unsubstituted heteroaryl, substituted or unsubstituted arylalkyl, —CN, —NO$_2$ and —S(O)$_2$R'. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl, 1-piperidinyl, 1-piperazinyl and 4-morpholinyl.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$–C$_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Description of the Embodiments

I. Inhibitors of Voltage-dependent Sodium Channels

In one aspect, the present invention provides compounds according to Formula I:

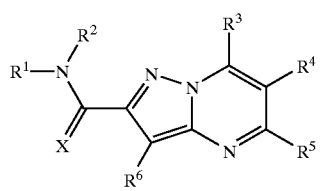

(I)

In Formula I, $R^1$ represents substituted or unsubstituted alkyl, substituted or unsubstituted aryl, substituted or unsubstituted heteroaryl, substituted or unsubstituted heterocycloalkyl, and substituted or unsubstituted aryl (alkyl). $R^2$ is a member selected from hydrogen and substituted or unsubstituted alkyl. $R^1$ and $R^2$ taken together with the nitrogen atom to which they are optionally joined to form a 4- to 8-membered heterocycloaryl ring. The symbol $R^3$ represents a member selected from hydrogen, substituted or unsubstituted alkyl, halo, amino, substituted or unsubstituted aryl, substituted or unsubstituted heteroaryl and substituted or unsubstituted heterocycloalkyl. The symbol $R^4$ represents a member selected from hydrogen, halo, substituted or unsubstituted alkyl and substituted or unsubstituted aryl. $R^5$ is a member selected from substituted or unsubstituted alkyl, substituted or unsubstituted aryl, substituted or unsubstituted heteroaryl and substituted or unsubstituted heterocycloalkyl. $R^6$ is a member selected from hydrogen, halo, substituted or unsubstituted aryl, substituted or unsubstituted heteroaryl, and substituted or unsubstituted heterocycloalkyl. X is either O or S, preferably O.

In those embodiments, in which X is O, $R^3$ is preferably a member selected from hydrogen and substituted or unsubstituted alkyl.

Representative compounds according to Formula I are set forth in FIG. 1.

Also within the scope of the present invention are compounds of the invention that are poly- or multi-valent species, including, for example, species such as dimers, trimers, tetramers and higher homologs of the compounds of the invention or reactive analogues thereof. The poly- and multi-valent species can be assembled from a single species or more than one species of the invention. For example, a dimeric construct can be "homo-dimeric" or "heterodimeric." Moreover, poly- and multi-valent constructs in which a compound of the invention or a reactive analogue thereof, is attached to an oligomeric or polymeric framework (e.g., polylysine, dextran, hydroxyethyl starch and the like) are within the scope of the present invention. The framework is preferably polyfunctional (i.e. having an array of reactive sites for attaching compounds of the invention). Moreover, the framework can be derivatized with a single species of the invention or more than one species of the invention.

Moreover, the present invention includes compounds within the motif set forth in Formula I, which are functionalized to afford compounds having water-solubility that is enhanced relative to analogous compounds that are not similarly functionalized. Thus, any of the substituents set forth herein can be replaced with analogous radicals that have enhanced water solubility. For example, it is within the scope of the invention to, for example, replace a hydroxyl group with a diol, or an amine with a quaternary amine, hydroxy amine or similar more water-soluble moiety. In a preferred embodiment, additional water solubility is imparted by substitution at a site not essential for the activity towards the ion channel of the compounds set forth herein with a moiety that enhances the water solubility of the parent compounds. Methods of enhancing the water-solubility of organic compounds are known in the art. Such methods include, but are not limited to, functionalizing an organic nucleus with a permanently charged moiety, e.g., quaternary ammonium, or a group that is charged at a physiologically relevant pH, e.g. carboxylic acid, amine. Other methods include, appending to the organic nucleus hydroxyl- or amine-containing groups, e.g. alcohols, polyols, polyethers, and the like. Representative examples include, but are not limited to, polylysine, polyethyleneimine, poly (ethyleneglycol) and poly(propyleneglycol). Suitable functionalization chemistries and strategies for these compounds are known in the art. See, for example, Dunn, R. L., et al., Eds. POLYMERIC DRUGS AND DRUG DELIVERY SYSTEMS, ACS Symposium Series Vol. 469, American Chemical Society, Washington, D.C. 1991.

Preparation of Sodium Channel Inhibitors

Compounds of the present invention can be prepared using readily available starting materials or known intermediates. The synthetic scheme set forth below provides an exemplary synthetic pathway for the preparation of compounds of the invention.

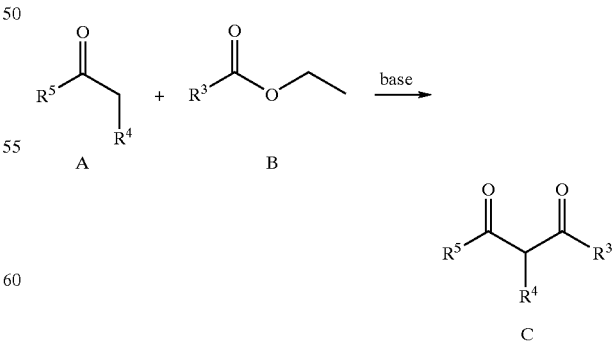

In step 1, the ketone (A) is made to react with an ester (B) in the presence of a base such as sodium methoxide in a solvent such as methanol to give the di-ketone (C).

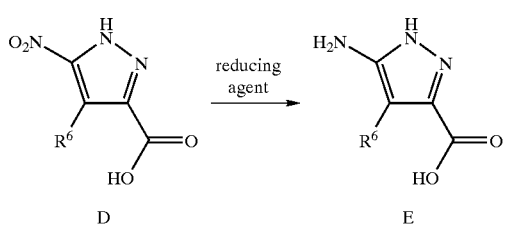

In step 2, the nitro functionality (D) is reduced under standard conditions such as treatment with hydrogen in the presence of palladium on carbon in a solvent such as methanol to give the amino compound (E).

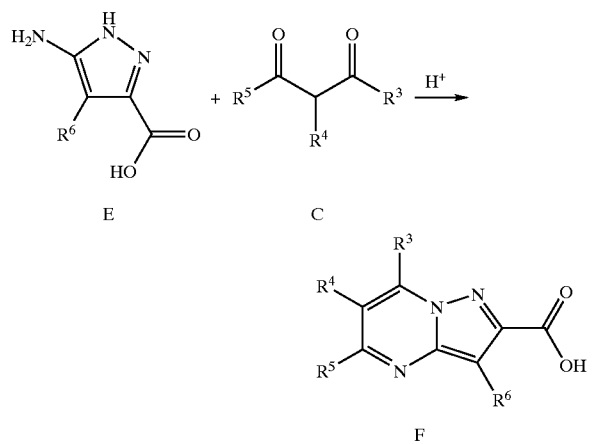

In step 3, the amine compound (E) is made to react with the di-ketone (C) in the presence of an acid, such as acetic acid, at elevated temperatures to produce the pyrazolopyrimidine carboxylic acid (F).

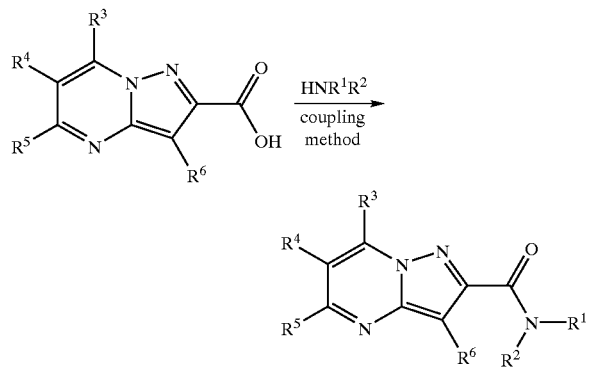

In step 4, the pyrazolopyrimidine carboxylic acid (F) may be made to react with an amine, $HNR^1R^2$, using standard coupling procedures in a variety of organic solvents to give a compound of Formula I where X is O.

Methods for preparing dimers, trimers and higher homologs of small organic molecules, such as those of the present invention, as well as methods of functionalizing a polyfunctional framework molecule are well known to those of skill in the art. For example, an aromatic amine of the invention is converted to the corresponding isothiocyanate by the action of thiophosgene. The resulting isothiocyanate is coupled to an amine of the invention, thereby forming either a homo- or heterodimeric species. Alternatively, the isothiocyanate is coupled with an amine-containing backbone, such as polylysine, thereby forming a conjugate between a polyvalent framework and a compound of the invention. If it is desired to prepare a heterofuntionalized polyvalent species, the polylysine is underlabeled with the first isothiocyanate and subsequently labeled with one or more different isothiocyanates. Alternatively, a mixture of isothiocyanates is added to the backbone. Purification proceeds by, for example, size exclusion chromatography, dialysis, nanofiltration and the like.

II. Assays for Blockers of Sodium Ion Channels

PN3 monomers as well as PN3 alleles and polymorphic variants are subunits of sodium channels. The activity of a sodium channel comprising PN3 subunits can be assessed using a variety of in vitro and in vivo assays, e.g., measuring current, measuring membrane potential, measuring ion flux, e.g., sodium or guanidinium, measuring sodium concentration, measuring second messengers and transcription levels, and using e.g., voltage-sensitive dyes, radioactive tracers, and patch-clamp electrophysiology.

A number of experimental models in the rat are appropriate for assessing the efficacy of the compounds of the invention. For example, the tight ligation of spinal nerves described by Kim et al., Pain 50: 355–363 (1992) can be used to experimentally determine the effect of the compounds of the invention on a PN3 channel. For example, a sodium channel blockade in vitro assay can be used to determine the effectiveness of compounds of Formula I as sodium channel blockers in an in vitro model by the inhibition of compound action potential propagation in isolated nerve preparations (Kourtney and Stricharz, LOCAL ANESTHETICS, Springer-Verlag, New York, 1987). The mechanical allodynia in vivo assay is also of use in determining the efficacy of compounds of the invention (Kim and Chung Pain 50:355 (1992)). Mechanical sensitivity can be assessed using a procedure described by Chaplan et al., J. Neurosci. Methods 53: 55–63 (1994). Other assays of use are known to those of skill in the art. See, for example, Loughhead et al., U.S. Pat. No. 6,262,078.

Inhibitors of the PN3 sodium channels can be tested using biologically active recombinant PN3, or naturally occurring TTX-resistant sodium channels, or by using native cells, like cells from the nervous system expressing a PN3 channel. PN3 channels can be isolated, co-expressed or expressed in a cell, or expressed in a membrane derived from a cell. In such assays, PN3 is expressed alone to form a homomeric sodium channel or is co-expressed with a second subunit (e.g., beta subunits) so as to form a heteromeric sodium channel. Exemplary expression vectors include, but are not limited to, PN3-pCDNA3.1. The PN3 channel can be stably expressed in mammalian expression systems.

Inhibition can be tested using one of the in vitro or in vivo assays described above. Samples or assays that are treated with a potential sodium channel inhibitor or activator are compared to control samples without the test compound, to examine the extent of inhibition. Control samples (untreated with activators or inhibitors) are assigned a relative sodium channel activity value of 100. Inhibition of channels comprising PN3 is achieved when the sodium channel activity value relative to the control is less than 70%, preferably less than 40% and still more preferably, less than 30%. Compounds that decrease the flux of ions will cause a detectable decrease in the ion current density by decreasing the probability of a channel comprising PN3 being open, by decreasing conductance through the channel, decreasing the number of channels, or decreasing the expression of channels.

Changes in ion flux may be assessed by determining changes in polarization (i.e., electrical potential) of the cell or membrane expressing the sodium channel. A preferred means to determine changes in cellular polarization is by measuring changes in current or voltage with the voltage-clamp and patch-clamp techniques, using the "cell-attached" mode, the "inside-out" mode, the "outside-out" mode, the "perforated cell" mode, the "one or two electrode" mode, or the "whole cell" mode (see, e.g., Ackerman et al., *New Engl. J. Med.* 336: 1575–1595 (1997)). Whole cell currents are conveniently determined using the standard methodology (see, e.g., Hamil et al., *Pflugers. Archiv.* 391: 85 (1981). Other known assays include: radiolabeled rubidium flux assays and fluorescence assays using voltage-sensitive dyes (see, e.g., Vestergarrd-Bogind et al., *J. Membrane Biol.* 88: 67–75 (1988); Daniel et al., *J. Pharmacol. Meth.* 25: 185–193 (1991); Holevinsky et al., *J. Membrane Biology* 137: 59–70 (1994)). Assays for compounds capable of inhibiting or increasing sodium flux through the channel proteins can be performed by application of the compounds to a bath solution in contact with and comprising cells having a channel of the present invention (see, e.g., Blatz et al., *Nature* 323: 718–720 (1986); Park, *J. Physiol.* 481: 555–570 (1994)). Generally, the compounds to be tested are present in the range from about 1 pM to about 100 mM, preferably from about 1 pM to about 1 $\mu$M. Other compounds range from about 1 nM to about 100 nM, preferably from about 1 nM to about 1 $\mu$M.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or guanidinium ions (see, e.g., Berger et al., U.S. Pat. No. 5,688,830). The cations can be measured in a variety of standard ways. They can be measured directly by concentration changes of the ions or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin-binding assay. When the functional consequences are determined using intact cells or animals, one can also measure a variety of effects such as transmitter release, hormone release, transcriptional changes to both known and uncharacterized genetic markers, changes in cell metabolism such as cell growth or pH changes, and changes in intracellular second messengers such as $Ca^{2+}$, or cyclic nucleotides.

High throughput screening (HTS) is of use in identifying promising candidates of the invention. Physiologically, Na channels open and close on a ms timescale. To overcome the short time in which channels are open the HTS assay can be run in the presence of an agent that modifies the gating of the channel, such as deltamethrin. This agent modifies the gating of Na channels and keeps the pore open for extended periods of time. In addition, while Na channels are primarily selective for Na, other monovalent cations can permeate the channel.

The specificity and effect of the PN3 blocking agents of the invention can also be assayed against non-specific blockers of PN3, such as tetracaine, mexilitine, and flecainide.

III. Pharmaceutical Compositions of Sodium Channel Inhibitors

In another aspect, the present invention provides pharmaceutical compositions comprising a pharmaceutically acceptable excipient and a compound of Formula I provided above.

Formulation of the Compounds (Compositions)

The compounds of the present invention can be prepared and administered in a wide variety of oral, parenteral and topical dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermnally. Accordingly, the present invention also provides pharmaceutical compositions comprising a pharmaceutically acceptable carrier or excipient and either a compound of Formula I, or a pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

IV. Methods for Inhibiting Ion Flow in Voltage-dependent Sodium Channels

In yet another aspect, the present invention provides methods for decreasing ion flow through voltage dependent sodium channels in a cell, comprising contacting a cell containing the target ion channels with a sodium channel-inhibiting amount of a compound of Formula I provided above.

The methods provided in this aspect of the invention are useful for the diagnosis of conditions that can be treated by inhibiting ion flux through voltage-dependent sodium channels, or for determining if a patient will be responsive to therapeutic agents, which act by inhibiting sodium channels.

V. Methods for Treating Conditions Mediated by Voltage-dependent Sodium Channels In still another aspect, the present invention provides a method for the treatment of a disorder or condition through inhibition of a voltage-dependent sodium channel. In this method, a subject in need of such treatment is administered an effective amount of a compound having the formula provided above. In a preferred embodiment, the compounds provided herein are used to treat a disorder or condition by inhibiting an ion channel of the voltage gated sodium channel family, e.g., PN3.

The compounds provided herein are useful as sodium channel inhibitors and find therapeutic utility via inhibition of voltage-dependent sodium channels in the treatment of diseases or conditions. The sodium channels that are typically inhibited are described herein as voltage-dependent sodium channels such as the PN3 sodium channels.

The compounds of the invention are particularly preferred for use in the treating, preventing or ameliorating pain or seizures. The method includes administering to a patient in need of such treatment, a therapeutically effective amount of a compound according to Formula I, or a pharmaceutically acceptable salt thereof.

The compounds, compositions and methods of the present invention are of particular use in treating pain, including both inflammatory and neuropathic pain. Exemplary forms of pain treated by a compound of the invention include, postoperative pain, osteoarthritis pain, pain associated with metastatic cancer, neuropathy secondary to metastatic inflammation, trigeminal neuralgia, glossopharangyl neuralgia, adiposis dolorosa, burn pain, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, pain following stroke, thalamic lesions, radiculopathy, and other forms of neuralgic, neuropathic, and idiopathic pain syndromes.

Idiopathic pain is pain of unknown origin, for example, phantom limb pain. Neuropathic pain is generally caused by injury or infection of the peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies.

Moreover, any sodium channel inhibitory substance possessed of satisfactory sodium channel modulating activity coupled with favorable intracranial transfer kinetics and metabolic stability is expected to show efficacy in central nervous system (CNS) diseases and disorders such as central nervous system ischemia, central nervous system trauma (e.g. brain trauma, spinal cord injury, whiplash injury, etc.), epilepsy, seizures, neurodegenerative diseases (e.g. amyotrophic lateral sclerosis (ALS), Alzheimer's disease, Huntington's chorea, Parkinson's disease, diabetic neuropathy, etc.), vascular dementia (e.g. multi-infarct dementia, Binswanger's disease, etc.), manic-depressive psychosis, depression, schizophrenia, chronic pain, trigeminal neuralgia, migraine, ataxia, bipolar disorder, spasticity, mood disorders, psychotic disorders, hearing and vision loss, age-related memory loss, learning deficiencies, anxiety and cerebral edema.

In treatment of the above conditions, the compounds utilized in the method of the invention are administered at the initial dosage of about 0.001 mg/kg to about 1000 mg/kg daily. A daily dose range of about 0.1 mg/kg to about 100 mg/kg is more typical. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day, if desired.

EXAMPLES

The following examples are offered to illustrate, but not to limit the claimed invention.

In the examples below, unless otherwise stated, temperatures are given in degrees Celsius (° C.); operations were carried out at room or ambient temperature (typically a range of from about 18–25° C.; evaporation of solvent was carried out using a rotary evaporator under reduced pressure (typically, 4.5–30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours), PS (polystyrene), DIE (diisopropylethylamine).

Example 1
1.1 $^{14}$C Guanidinium Ion Influx Binding Assay

PN3 stably expressed in a host cell line were maintained in DMEM with 5% fetal bovine serum and 300 μg/ml G-418. The cells were subcultured and grown to confluence in 96-well plates 24–48 h before each experiment. After the growth medium was removed, the cells were washed with warm buffer (25 mM Hepes-Tris, 135 mM choline chloride, 5.4 mM potassium chloride, 0.98 mM magnesium sulfate, 5.5 mM glucose, and 1 mg/ml BSA, pH 7.4) and incubated in buffer on a 36° C. slide warmer for approximately 10 minutes. Various concentrations of the test compounds or standard sodium channel blockers (10 μM) and then deltamethrine (10 μM) were added to each well. After the cells were exposed to deltamethrine for 5 minutes, 5 μM of $^{14}$C-guanidinium was added, incubated with the radioligand (30–60 min), washed with ice-cold buffer, and dissolved in 0.1N sodium hydroxide. The radioactivity and the protein concentration of each cell lysate were determined by liquid scintillation counting and the protein assay using Pierce BCA reagent.

Example 2
2.1 Mechanical Allodynia In vivo Assay

This assay determines the effectiveness of compounds of Formula I in relieving one of the symptoms in an in vivo model of neuropathic pain produced by spinal nerve ligation, namely mechanical allodynia.

Tactile allodynia was induced in rats using the procedures described by Kim and Chung, *Pain* 50: 355–363 (1992). Briefly, the rats were anesthetized with 2–5% inhaled isoflurane and maintained by 1% isoflurane. Each animal was then placed in a prone position, a 3 cm lateral incision was made, and the left paraspinal muscles separated from the spinous process at the $L_4$-$S_2$ level. The $L_6$ transverse process was then removed in order to visually identify the $L_4$-$L_6$ spinal nerves. The $L_5$ and $L_6$ spinal nerves were then individually isolated and tightly ligated with silk thread. The wound was then closed in layers by silk sutures. These procedures produced rats which developed a significant increase in sensitivity to mechanical stimuli that did not elicit a response in normal rats.

Mechanical sensitivity was assessed using a procedure described by Chaplan et al., *J. Neurosci. Methods* 53: 55–63 (1994). Briefly, a series of eight Von Frey filaments of varying rigidity strength were applied to the plantar surface of the hind paw ipsilaterial to the ligations with just enough force to bend the filament. The filaments were held in this position for no more than three seconds or until a positive allodynic response was displayed by the rat. A positive allodynic response consisted of lifting the affected paw followed immediately by licking or shaking of the paw. The order and frequency with which the individual filaments were applied were determined by using Dixon up-down method. Testing was initiated with the middle hair of the series with subsequent filaments being applied in consecutive fashion, either ascending or descending, depending on whether a negative or positive response, respectively, was obtained with the initial filament.

2.2 Thermal Hyperalgesia In vivo Assay

This assay determines the effectiveness of compounds in relieving one of the symptoms of neuropathic pain produced by unilateral mononeuropathy, namely thermal hyperalgesia.

The rats having had surgery as described above were assessed for thermal hyperalgesia sensitivity at least 5–7 days post-surgery. Briefly, the rats were placed beneath inverted plexiglass cages upon an elevated glass platform and a radiant heat source beneath the glass was aimed at the plantar hindpaw. The duration of time before the hindpaw was withdrawn from the floor was measured to the nearest tenth of a second. The cutoff time for the heat stimulus was 40 seconds, and the light was calibrated such that this stimulus duration did not burn or blister the skin. Three latency measurements were taken for each hindpaw ipsilateral to the ligation in each test session, alternating left and right hindpaws, with greater than 1 minute intervals between tests.

2.3 Results

The results show that after oral administration the compounds of the invention produce efficacious anti-allodynic effects at doses less then or equal to 100 mg/kg. The results show that after IV administration the compounds of the invention produce efficacious anti-hyperalgesic effects at doses less than or equal to 30 mg/kg. Overall, the compounds of the present invention were found to be effective in reversing mechanical allodynia-like and thermal hyperalgesia-like symptoms.

Example 3
General Procedure for Diketone Formation

Trifluoro-acetic acid ethyl ester (2 equivalents) was added to a solution of ketone (1 equivalent) in methanol containing sodium methoxide (1.5 equivalents). The reaction mixture was heated at reflux overnight, concentrated under reduced pressure and acidified with aqueous hydrochloric acid (10%). The aqueous solution was extracted with ethyl acetate (10×50 mL). The organic layers are collected, dried over sodium sulfate, filtered and concentrated under reduced pressure. The crude product was purified by column chromatography on silica gel to give the trifluoromethyl diketone.

Example 4
Preparation of 4,4,4-trifluoro-1-pyridin-2-yl-butane-1,3-dione

Trifluoro-acetic acid ethyl ester (9.82 mL, 82.5 mmol) was added to a solution of 1-pyridin-2-yl-ethanone (5.00 g, 41.2 mmol) in methanol (40 mL) containing sodium methoxide (61.8 mmol). The reaction mixture was heated at reflux overnight, concentrated under reduced pressure and acidified with aqueous hydrochloric acid (10%). The aqueous solution was extracted with ethyl acetate (10×50 mL). The organic layers were collected, dried over sodium sulfate, filtered, and concentrated under reduced pressure. The crude product was purified by column chromatography on silica gel to give 4,4,4-trifluoro-1-pyridin-2-yl-butane-1,3-dione (7.26 g, 81%).

Example 5
General Procedure for Pyrazolopyrimidine Carboxylic Acid Formation Procedure A A diketone (1 equivalent) and 5-amino-1H-pyrazole-3-carboxylic acid (1 equivalent) in acetic acid was heated at reflux for 12–24 hours. The reaction was concentrated under reduced pressure and the crude product was purified by column chromatography on silica gel to provide the pyrazolopyrimidine carboxylic acid.

5.1 Preparation of 5-pyridin-2-yl-7-trifluoromethyl-pyrazolo[1,5-a]pyrimidine-2-carboxylic acid 4,4,4-Trifluoro-1-pyridin-2-yl-butane-1,3-dione (3.00 g, 13.8 mmol) and 5-amino-1H-pyrazole-3-carboxylic acid (1.76 g, 13.8 mmol) in acetic acid (100 ml) was heated at reflux overnight. The reaction mixture was concentrated under reduced pressure and the crude product was purified by column chromatography on silica gel to give 5-pyridin-2-yl-7-trifluoromethyl-pyrazolo[1,5-a]pyrimidine-2-carboxylic acid (3.04 g, 71%).

5.2 Preparation of 5-(3,4-Dichloro-phenyl)-7-trifluoromethyl-pyrazolo[1,5-a]pyrimidine-2-carboxylic acid 1-(3,4-Dichloro-phenyl)-4,4,4-trifluoro-butane-1,3-dione (1.00 g, 3.51 mmol) and 5-amino-1H-pyrazole-3-carboxylic acid (0.446 g, 3.51 mmoL) in acetic acid (100 mL) was heated at reflux for 48 hours. The reaction concentrated under reduced pressure and the crude product was purified by column chromatography on silica gel to give 5-(3,4-dichloro-phenyl)-7-trifluoromethyl-pyrazolo[1,5-a]pyrimidine-2-carboxylic acid (1.20 g, 90%).

Procedure B

An α-cyano ketone (1 equivalent) and 5-amino-1H-pyrazole-3-carboxylic acid (1 equivalent) in pyridine was heated at reflux for 24–96 hours. The reaction was concentrated under reduced pressure and the crude product was purified by column chromatography on silica gel to provide the pyrazolopyrimidine carboxylic acid.

5.3 Preparation of 7-amino-5-(3,4-dichloro-phenyl)-pyrazolo[1,5-a]pyrimidine-2-carboxylic acid 3-(3,4-Dichloro-phenyl)-3-oxo-propionitrile (1.00 g, 4.67 mmol) and 5-amino-1H-pyrazole-3-carboxylic acid (0.593 g, 4.67 mmol) in pyridine (50 mL) was heated at reflux for 3 days. The reaction was concentrated under reduced pressure and the crude product was purified by column chromatography on silica gel to give 7-amino-5-(3,4-dichloro-phenyl)-pyrazolo[1,5-a]pyrimidine-2-carboxylic acid (0.125 g, 8%).

General Procedure for amide Formation

Benzotriazol-1-yloxy-tris(dimethylamino)-phosphonium hexafluorophosphate (BOP) (1.2 equivalents) was added to a suspension of a pyrazolopyrimidine carboxylic acid (1 equivalents) and an amine (1.2 equivalents) in tetrahydrofuran containing triethylamine (3 equivalents). The reaction mixture was stirred overnight at room temperature, diluted with ethyl ether (reaction volume) and washed with a saturated aqueous solution of sodium bicarbonate. The organic layer was collected and concentrated under reduced pressure. The crude product was purified by column chromatography on silica gel to give the amide.

5.4 Preparation of 5-(3,4-dichloro-phenyl)-7-trifluoromethyl-pyrazolo[1,5-a]pyrimidine-2-carboxylic acid benzylamide Benzotriazol-1-yloxy-tris(dimethylamino)-phosphonium hexafluorophosphate (BOP) (0.845 g, 1.91 mmol) was added to a suspension of 5-(3,4-dichloro-phenyl)-7-trifluoromethyl-pyrazolo[1,5-a]pyrimidine-2-carboxylic acid (0.600 g, 1.59 mmol) and benzylamine (0.209 mL, 1.91 mmol) in tetrahydrofuran (25 ml) containing triethylamine (0.665 mL, 4.77 mmol). The reaction mixture was stirred overnight at room temperature, diluted with ethyl ether (25 mL) and washed with a saturated aqueous solution of sodium bicarbonate (50 mL). The organic layer was collected, concentrated under reduced pressure and the crude product was purified by column chromatography on silica gel to give 5-(3,4-dichloro-phenyl)-7-trifluoromethyl-pyrazolo[1,5-a]pyrimidine-2-carboxylic acid benzylamide (0.665 g, 89%).

5.5 Preparation of 5-Pyridin-2-yl-7-trifluoromethyl-pyrazolo[1,5-a]pyrimidine-2-carboxylic acid benzylamide Benzotriazol-1-yloxy-tris(dimethylamino)-phosphonium hexafluorophosphate (BOP) (0.430 g, 0.973 mmol) was added to a suspension of 5-pyridin-2-yl-7-trifluoromethyl-pyrazolo[1,5-a]pyrimidine-2-carboxylic acid (0.250 g, 0.811 mmol) and benzylamine (0.106 mL, 0.973 mmol) in tetrahydrofuran (10 mL) containing triethylamine (0.339 ml, 2.43 mmol). The reaction mixture was stirred overnight at room temperature, diluted with ethyl ether (10 mL) and washed with a saturated aqueous solution of sodium bicarbonate (10 mL). The organic layer was collected, concentrated under reduced pressure and crude the product was purified by column chromatography on silica gel to give 5-pyridin-2-yl-7-trifluoromethyl-pyrazolo[1,5-a]pyrimidine-2-carboxylic acid benzylamide (0.280 g, 86%).

5.6 Preparation of 7-amino-5-(3,4-dichloro-phenyl)-pyrazolo[1,5-a]pyrimidine-2-carboxylic acid benzylamide Benzotriazol-1-yloxy-tris(dimethylamino)-phosphonium hexafluorophosphate (BOP) (0.081 g, 0.184 mmol) was added to a suspension of 7-amino-5-(3,4-dichloro-phenyl)-pyrazolo[1,5-a]pyrimidine-2-carboxylic acid (0.050 g, 0.154 mmol) and benzylamine (0.034 mL, 0.308 mmol) in tetrahydrofuran (5 ml) containing triethylamine (0.064 mL, 0.462 mmol). The reaction mixture was stirred overnight at room temperature, diluted with ethyl ether (5 mL) and washed with a saturated aqueous solution of sodium bicarbonate (10 mL). The organic layer was collected, concentrated under reduced pressure and the crude product was purified by column chromatography to give 7-amino-5-(3,4-dichloro-phenyl)-pyrazolo[1,5-a]pyrimidine-2-carboxylic acid benzylamide (0.026 g, 55%).

5.7 Preparation of 5-(4-Bromo-phenyl)-7-trifluoromethyl-pyrazolo[1,5-a]pyrimidine-2-carboxylic acid (thiophen-2-ylmethyl)-amide Benzotriazol-1-yloxy-tris(dimethylamino)-phosphonium hexafluorophosphate (BOP) (0.144 g, 0.327 mmol) was added to a suspension of 5-(4-bromo-phenyl)-7-trifluoromethyl-pyrazolo[1,5-a]pyrimidine-2-carboxylic acid (0.115 g, 0.298 mmol) and thiophene-2-methylamine (0.034 mL, 0.327 mmol) in THF (10 mL) containing triethylamine (0.124 mL, 0.893 mmol). The reaction mixture was stirred overnight at room temperature, diluted with ethyl ether (5 mL) and washed with a saturated aqueous solution of sodium bicarbonate (10 mL). The organic layer was collected, concentrated under reduced pressure and the crude product was purified by column chromatography to give 5-(4-bromo-phenyl)-7-trifluoromethyl-pyrazolo[1,5-a]pyrimidine-2-carboxylic acid (thiophen-2-ylmethyl)-amide (0.105 g, 73%).

5.8 Preparation of 5-(3,4-Dichloro-phenyl)-7-trifluoromethyl-pyrazolo[1,5-a]pyrimidine-2-carboxylic acid (pyridin-2-ylmethyl)-amide Benzotriazol-1-yloxy-tris(dimethylamino)-phosphonium hexafluorophosphate (BOP) (0.141 g, 0.319 mmol) was added to a suspension of 5-(3,4-dichloro-phenyl)-7-trifluoromethyl-pyrazolo[1,5-a]pyrimidine-2-carboxylic acid (0.100 g, 0.265 mmol) and C-Pyridin-2-yl-methylamine (0.033 mL, 0.319 mmol) in tetrahydrofuran (10 mL) containing triethylamine (0.111 mL, 0.795 mmol). The reaction mixture was stirred overnight at room temperature, diluted with ethyl ether (10 mL) and washed with a saturated aqueous solution of sodium bicarbonate (10 mL). The organic layer was collected, concentrated under reduced pressure and the crude product was purified by column chromatography on silica gel to give 5-(3,4-dichloro-phenyl)-7-trifluoromethyl-pyrazolo[1,5-a]pyrimidine-2-carboxylic acid (pyridin-2-ylmethyl)-amide (0.073 g, 59%).

Example 6

Preparation of 5-(4-Chloro-phenyl)-7-trifluoromethyl-pyrazolo[1,5-a]pyrimidine-2-carboxylic acid (3-methanesulfonyl-phenyl)-amide 5-(4-Chloro-phenyl)-7-trifluoromethyl-pyrazolo[1,5-a]pyrimidine-2-carbonyl chloride (0.100 g, 0.277 mmol)

(prepared from 5-(4-chloro-phenyl)-7-trifluoromethyl-pyrazolo[1,5-a]pyrimidine-2-carboxylic acid using standard procedures, e.g.; thionyl chloride) was added to a solution of 3-methanesulfonyl-phenylamine (0.052 mL, 0.304 mmol) in acetonitrile (10 mL) containing pyridine (0.067 mL, 0.831 mmol). The reaction mixture was stirred overnight at room temperature, diluted with ethyl acetate (25 mL) and washed with 1M hydrochloric acid (50 mL). The organic layer was collected, concentrated under reduced pressure and the crude product was purified by column chromatography on silica gel to give 5-(4-chloro-phenyl)-7-trifluoromethyl-pyrazolo[1,5-a]pyrimidine-2-carboxylic acid (3-methanesulfonyl-phenyl)-amide (0.128 g, 93%).

Example 7

Example 7 sets forth representative compounds of the invention.

| name | MZ |
| --- | --- |
| 5-Phenyl-7-trifluoromethyl-pyrazolo[1,5-a]pyrimidine-2-carboxylic acid (5-bromo-pyridin-2-yl)-amide | 461 |
| 6-Bromo-pyrazolo[1,5-a]pyrimidine-2-carboxylic acid (5-bromo-pyridin-2-yl)-amide | 395 |
| 3-Chloro-5-phenyl-7-trifluoromethyl-pyrazolo[1,5-a]pyrimidine-2-carboxylic acid (5-bromo-pyridin-2-yl)-amide | 495 |
| 5-Thiophen-2-yl-7-trifluoromethyl-pyrazolo[1,5-a]pyrimidine-2-carboxylic acid (2-morpholin-4-yl-ethyl)-amide | 425 |
| 5-(4-Methoxy-phenyl)-7-trifluoromethyl-pyrazolo[1,5-a]pyrimidine-2-carboxylic acid (furan-2-ylmethyl)-amide | 416 |
| 3-Bromo-5-(4-methoxy-phenyl)-7-trifluoromethyl-pyrazolo[1,5-a]pyrimidine-2-carboxylic acid (furan-2-ylmethyl)-amide | 494 |
| 5-Phenyl-7-trifluoromethyl-pyrazolo[1,5-a]pyrimidine-2-carboxylic acid (2-morpholin-4-yl-ethyl)-amide | 419 |
| 3-Chloro-5-phenyl-7-trifluoromethyl-pyrazolo[1,5-a]pyrimidine-2-carboxylic acid (furan-2-ylmethyl)-amide | 420 |
| 5-Thiophen-2-yl-7-trifluoromethyl-pyrazolo[1,5-a]pyrimidine-2-carboxylic acid (furan-2-ylmethyl)-amide | 392 |
| 5-Furan-2-yl-7-trifluoromethyl-pyrazolo[1,5-a]pyrimidine-2-carboxylic acid (pyridin-3-ylmethyl)-amide | 387 |
| 3-Chloro-5-thiophen-2-yl-7-trifluoromethyl-pyrazolo[1,5-a]pyrimidine-2-carboxylic acid (pyridin-3-ylmethyl)-amide | 437 |
| 3-Chloro-5-thiophen-2-yl-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 532 |
| 3-Chloro-5-phenyl-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 526 |
| 5-Thiophen-2-yl-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 498 |
| 3-Bromo-5-(4-bromo-phenyl)-7-trifluoromethyl-pyrazolo[1,5-a]pyrimidine-2-carboxylic acid (2-morpholin-4-yl-ethyl)-amide | 575 |
| 5-(4-Nitro-phenyl)-7-trifluoromethyl-pyrazolo[1,5-a]pyrimidine-2-carboxylic acid (furan-2-ylmethyl)-amide | 431 |
| 5-(4-Nitro-phenyl)-7-trifluoromethyl-pyrazolo[1,5-a]pyrimidine-2-carboxylic acid (2-morpholin-4-yl-ethyl)-amide | 464 |
| 7-Trifluoromethyl-5,6-dihydro-7a,8,11-triaza-cyclopenta[b]phenanthrene-9-carboxylic acid (2-morpholin-4-yl-ethyl)-amide | 445 |
| 3-Chloro-5-furan-2-yl-7-trifluoromethyl-pyrazolo[1,5-a]pyrimidine-2-carboxylic acid (pyridin-3-ylmethyl)-amide | 421 |
| 3-Chloro-5-furan-2-yl-7-trifluoromethyl-pyrazolo[1,5-a]pyrimidine-2-carboxylic acid (furan-2-ylmethyl)-amide | 410 |
| 3-Chloro-5-(4-methoxy-phenyl)-7-trifluoromethyl-pyrazolo[1,5-a]pyrimidine-2-carboxylic acid (pyridin-3-ylmethyl)-amide | 461 |
| 3-Chloro-5-(4-chloro-phenyl)-7-trifluoromethyl-pyrazolo[1,5-a]pyrimidine-2-carboxylic acid (2-morpholin-4-yl-ethyl)-amide | 487 |
| 3-Chloro-5-(4-chloro-phenyl)-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 560 |
| 3-Chloro-5-p-tolyl-7-trifluoromethyl-pyrazolo[1,5-a]pyrimidine-2-carboxylic acid (furan-2-ylmethyl)-amide | 434 |
| 3-Chloro-5-p-tolyl-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 540 |
| 3-Chloro-5-(3,4-dimethoxy-phenyl)-7-trifluoromethyl-pyrazolo[1,5-a]pyrimidine-2-carboxylic acid (furan-2-ylmethyl)-amide | 480 |
| 5-p-Tolyl-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 506 |
| 5-Benzo[1,3]dioxol-5-yl-7-trifluoromethyl-pyrazolo[1,5-a]pyrimidine-2-carboxylic acid (furan-2-ylmethyl)-amide | 430 |
| 5-Phenyl-7-trifluoromethyl-pyrazolo[1,5-a]pyrimidine-2-carboxylic acid (furan-2-ylmethyl)-amide | 386 |

-continued

| name | MZ |
|---|---|
| (6-Bromo-pyrazolo[1,5-a]pyrimidin-2-yl)-piperidin-1-yl-methanone | 308 |
| (6-Bromo-pyrazolo[1,5-a]pyrimidin-2-yl)-morpholin-4-yl-methanone | 310 |
| 6-Bromo-pyrazolo[1,5-a]pyrimidine-2-carboxylic acid benzylamide | 330 |
| 6-Bromo-pyrazolo[1,5-a]pyrimidine-2-carboxylic acid butylamide | 296 |
| 3,6-Dibromo-pyrazolo[1,5-a]pyrimidine-2-carboxylic acid butylamide | 374 |
| Morpholin-4-yl-(5-thiophen-2-yl-7-trifluoromethyl-pyrazolo[1,5-a]pyrimidin-2-yl)-methanone | 382 |
| 3-Bromo-5-thiophen-2-yl-7-trifluoromethyl-pyrazolo[1,5-a]pyrimidine-2-carboxylic acid (pyridin-3-ylmethyl)-amide | 481 |
| 3-Bromo-5-phenyl-7-trifluoromethyl-pyrazolo[1,5-a]pyrimidine-2-carboxylic acid (2-methoxy-ethyl)-amide | 442 |
| (5-Furan-2-yl-7-trifluoromethyl-pyrazolo[1,5-a]pyrimidin-2-yl)-pyrrolidin-1-yl-methanone | 350 |
| (3-Chloro-5-thiophen-2-yl-7-trifluoromethyl-pyrazolo[1,5-a]pyrimidin-2-yl)-morpholin-4-yl-methanone | 416 |
| 3-Chloro-5-phenyl-7-trifluoromethyl-pyrazolo[1,5-a]pyrimidine-2-carboxylic acid (3-methoxy-5-nitro-phenyl)-amide | 491 |
| [5-(4-Methoxy-phenyl)-7-trifluoromethyl-pyrazolo[1,5-a]pyrimidin-2-yl]-morpholin-4-yl-methanone | 406 |
| (4-Methyl-piperazin-1-yl)-(5-phenyl-7-trifluoromethyl-pyrazolo[1,5-a]pyrimidin-2-yl)-methanone | 389 |
| 5-(4-Chloro-phenyl)-7-trifluoromethyl-pyrazolo[1,5-a]pyrimidine-2-carboxylic acid (2-trifluoromethyl-phenyl)-amide | 484 |
| (4-Methyl-piperazin-1-yl)-(5-p-tolyl-7-trifluoromethyl-pyrazolo[1,5-a]pyrimidin-2-yl)-methanone | 403 |
| 3-Chloro-5-furan-2-yl-7-trifluoromethyl-pyrazolo[1,5-a]pyrimidine-2-carboxylic acid (2,4-dimethoxy-phenyl)-amide | 466 |
| 3-Chloro-5-furan-2-yl-7-trifluoromethyl-pyrazolo[1,5-a]pyrimidine-2-carboxylic acid (3-diethylamino-propyl)-amide | 443 |
| 3-Chloro-5-p-tolyl-7-trifluoromethyl-pyrazolo[1,5-a]pyrimidine-2-carboxylic acid (tetrahydro-furan-2-ylmethyl)-amide | 438 |
| 3-Chloro-5-furan-2-yl-7-trifluoromethyl-pyrazolo[1,5-a]pyrimidine-2-carboxylic acid (3-methoxy-5-nitro-phenyl)-amide | 481 |
| (3-Chloro-5-furan-2-yl-7-trifluoromethyl-pyrazolo[1,5-a]pyrimidin-2-yl)-morpholin-4-yl-methanone | 400 |
| 5-(4-Methoxy-phenyl)-7-trifluoromethyl-pyrazolo[1,5-a]pyrimidine-2-carboxylic acid (2-hydroxy-5-methyl-phenyl)-amide | 442 |
| [5-(4-Fluoro-phenyl)-7-trifluoromethyl-pyrazolo[1,5-a]pyrimidin-2-yl]-(4-methyl-piperazin-1-yl)-methanone | 407 |
| 5-(3,4-Dimethoxy-phenyl)-7-trifluoromethyl-pyrazolo[1,5-a]pyrimidine-2-carboxylic acid (3-methoxy-5-nitro-phenyl)-amide | 517 |
| [5-(4-Bromo-phenyl)-7-trifluoromethyl-pyrazolo[1,5-a]pyrimidin-2-yl]-pyrrolidin-1-yl-methanone | 438 |
| 5-Phenyl-7-trifluoromethyl-pyrazolo[1,5-a]pyrimidine-2-carboxylic acid (3-cyano-4,5,6,7-tetrahydro-benzo[b]thiophen-2-yl)-amide | 467 |
| 3-Chloro-5-phenyl-7-trifluoromethyl-pyrazolo[1,5-a]pyrimidine-2-carboxylic acid (2,4-dichloro-phenyl)-amide | 484 |
| [5-(4-Methoxy-phenyl)-7-trifluoromethyl-pyrazolo[1,5-a]pyrimidin-2-yl]-piperidin-1-yl-methanone | 404 |
| 5-Phenyl-7-trifluoromethyl-pyrazolo[1,5-a]pyrimidine-2-carboxylic acid (pyridin-3-ylmethyl)-amide | 397 |
| 5-Phenyl-7-trifluoromethyl-pyrazolo[1,5-a]pyrimidine-2-carboxylic acid (2-chloro-pyridin-3-yl)-amide | 417 |
| 5-Phenyl-7-trifluoromethyl-pyrazolo[1,5-a]pyrimidine-2-carboxylic acid [3-(4-chloro-phenoxy)-5-nitro-phenyl]-amide | 553 |
| 5-Phenyl-7-trifluoromethyl-pyrazolo[1,5-a]pyrimidine-2-carboxylic acid cyclohexylamide | 388 |
| 3-Chloro-5-phenyl-7-trifluoromethyl-pyrazolo[1,5-a]pyrimidine-2-carboxylic acid (2-ethyl-phenyl)-amide | 444 |
| 3-Chloro-5-phenyl-7-trifluoromethyl-pyrazolo[1,5-a]pyrimidine-2-carboxylic acid (2-morpholin-4-yl-ethyl)-amide | 453 |
| (4-Benzyl-piperazin-1-yl)-(3-chloro-5-phenyl-7-trifluoromethyl-pyrazolo[1,5-a]pyrimidin-2-yl)-methanone | 499 |
| 3-Chloro-5-phenyl-7-trifluoromethyl-pyrazolo[1,5-a]pyrimidine-2-carboxylic acid (3-trifluoromethyl-phenyl)-amide | 484 |
| 3-Chloro-5-phenyl-7-trifluoromethyl-pyrazolo[1,5-a]pyrimidine-2-carboxylic acid (3-hydroxy-phenyl)-amide | 432 |
| 3-Bromo-5-phenyl-7-trifluoromethyl-pyrazolo[1,5-a]pyrimidine-2-carboxylic acid (3,4-dimethyl-phenyl)-amide | 488 |
| 3-Bromo-5-phenyl-7-trifluoromethyl-pyrazolo[1,5-a]pyrimidine-2-carboxylic acid (2,3-dichloro-phenyl)-amide | 528 |
| 3-Bromo-5-phenyl-7-trifluoromethyl-pyrazolo[1,5-a]pyrimidine-2-carboxylic acid (2-chloro-pyridin-3-yl)-amide | 495 |
| 3-Bromo-5-phenyl-7-trifluoromethyl-pyrazolo[1,5-a]pyrimidine-2-carboxylic acid cyclohexylamide | 466 |
| 5-Phenyl-7-trifluoromethyl-pyrazolo[1,5-a]pyrimidine-2-carboxylic acid (2-chloro-5-trifluoromethyl-phenyl)-amide | 484 |

-continued

| name | MZ |
|---|---|
| 5-Phenyl-7-trifluoromethyl-pyrazolo[1,5-a]pyrimidine-2-carboxylic acid (4-chloro-2,5-dimethoxy-phenyl)-amide | 476 |
| Azepan-1-yl-(5-phenyl-7-trifluoromethyl-pyrazolo[1,5-a]pyrimidin-2-yl)-methanone | 388 |
| 5-Phenyl-7-trifluoromethyl-pyrazolo[1,5-a]pyrimidine-2-carboxylic acid (2-methylsulfanyl-phenyl)-amide | 428 |
| 3-Chloro-5-phenyl-7-trifluoromethyl-pyrazolo[1,5-a]pyrimidine-2-carboxylic acid (2-bromo-4,6-difluoro-phenyl)-amide | 530 |
| Azepan-1-yl-(3-chloro-5-phenyl-7-trifluoromethyl-pyrazolo[1,5-a]pyrimidin-2-yl)-methanone | 422 |
| 3-Bromo-5-phenyl-7-trifluoromethyl-pyrazolo[1,5-a]pyrimidine-2-carboxylic acid (2-bromo-4,6-difluoro-phenyl)-amide | 574 |
| 3-Bromo-5-phenyl-7-trifluoromethyl-pyrazolo[1,5-a]pyrimidine-2-carboxylic acid (3-diethylamino-propyl)-amide | 497 |
| (4-Benzoyl-piperazin-1-yl)-(5-thiophen-2-yl-7-trifluoromethyl-pyrazolo[1,5-a]pyrimidin-2-yl)-methanone | 485 |
| 5-Thiophen-2-yl-7-trifluoromethyl-pyrazolo[1,5-a]pyrimidine-2-carboxylic acid tert-butylamide | 368 |
| 5-Thiophen-2-yl-7-trifluoromethyl-pyrazolo[1,5-a]pyrimidine-2-carboxylic acid [3-(4-chloro-phenoxy)-5-nitro-phenyl]-amide | 559 |
| 5-Thiophen-2-yl-7-trifluoromethyl-pyrazolo[1,5-a]pyrimidine-2-carboxylic acid [3,5-bis-(4-fluoro-phenoxy)-phenyl]-amide | 608 |
| 5-Thiophen-2-yl-7-trifluoromethyl-pyrazolo[1,5-a]pyrimidine-2-carboxylic acid (2-hydroxy-5-methyl-phenyl)-amide | 418 |
| 5-Thiophen-2-yl-7-trifluoromethyl-pyrazolo[1,5-a]pyrimidine-2-carboxylic acid (3-trifluoromethyl-phenyl)-amide | 456 |
| 5-Thiophen-2-yl-7-trifluoromethyl-pyrazolo[1,5-a]pyrimidine-2-carboxylic acid benzo[1,3]dioxol-5-ylamide | 432 |
| 3-Bromo-5-thiophen-2-yl-7-trifluoromethyl-pyrazolo[1,5-a]pyrimidine-2-carboxylic acid sec-butylamide | 446 |
| 3-Bromo-5-thiophen-2-yl-7-trifluoromethyl-pyrazolo[1,5-a]pyrimidine-2-carboxylic acid (4-chloro-phenyl)-amide | 500 |
| 3-Bromo-5-thiophen-2-yl-7-trifluoromethyl-pyrazolo[1,5-a]pyrimidine-2-carboxylic acid (3-trifluoromethyl-phenyl)-amide | 534 |
| 3-Bromo-5-thiophen-2-yl-7-trifluoromethyl-pyrazolo[1,5-a]pyrimidine-2-carboxylic acid (2-trifluoromethyl-phenyl)-amide | 534 |
| 3-Bromo-5-thiophen-2-yl-7-trifluoromethyl-pyrazolo[1,5-a]pyrimidine-2-carboxylic acid (3-chloro-2-methyl-phenyl)-amide | 514 |
| 3-Bromo-5-thiophen-2-yl-7-trifluoromethyl-pyrazolo[1,5-a]pyrimidine-2-carboxylic acid benzo[1,3]dioxol-5-ylamide | 510 |
| 3-Bromo-5-thiophen-2-yl-7-trifluoromethyl-pyrazolo[1 5-a]pyrimidine-2-carboxylic acid [3-(4-bromo-phenoxy)-5-nitro-phenyl]-amide | 681 |
| 3-Bromo-5-thiophen-2-yl-7-trifluoromethyl-pyrazolo[1,5-a]pyrimidine-2-carboxylic acid [3-(3-chloro-phenoxy)-5-nitro-phenyl]-amide | 637 |
| 5-Furan-2-yl-7-trifluoromethyl-pyrazolo[1,5-a]pyrimidine-2-carboxylic acid (5-chloro-2-methoxy-phenyl)-amide | 436 |
| 5-Furan-2-yl-7-trifluoromethyl-pyrazolo[1,5-a]pyrimidine-2-carboxylic acid [3-(4-iodo-phenoxy)-5-nitro-phenyl]-amide | 635 |
| (3,4-Dihydro-2H-quinolin-1-yl)-(5-furan-2-yl-7-trifluoromethyl-pyrazolo[1,5-a]pyrimidin-2-yl)-methanone | 412 |
| 5-Furan-2-yl-7-trifluoromethyl-pyrazolo[1,5-a]pyrimidine-2-carboxylic acid (2,3-dichloro-phenyl)-amide | 440 |
| [3-Bromo-5-(4-bromo-thiophen-2-yl)-7-trifluoromethyl-pyrazolo[1,5-a]pyrimidin-2-yl]-piperidin-1-yl-methanone | 536 |
| 3-Bromo-5-(4-bromo-thiophen-2-yl)-7-trifluoromethyl-pyrazolo[1,5-a]pyrimidine-2-carboxylic acid cyclohexylamide | 550 |
| (3-Bromo-5-phenyl-7-trifluoromethyl-pyrazolo[1,5-a]pyrimidin-2-yl)-morpholin-4-yl-methanone | 454 |
| 5-(4-Methoxy-phenyl)-7-trifluoromethyl-pyrazolo[1,5-a]pyrimidine-2-carboxylic acid amide | 336 |
| 5-{[3-Bromo-5-(4-methoxy-phenyl)-7-trifluoromethyl-pyrazolo[1,5-a]pyrimidine-2-carbonyl]-amino}-3-methyl-thiophene-2,4-dicarboxylic acid diethyl ester | 654 |
| 5-Phenyl-7-trifluoromethyl-pyrazolo[1,5-a]pyrimidine-2-carboxylic acid (3-chloro-phenyl)-amide | 416 |
| 3-Chloro-5-phenyl-7-trifluoromethyl-pyrazolo[1,5-a]pyrimidine-2-carboxylic acid (3,4-dimethyl-phenyl)-amide | 444 |
| 5-Thiophen-2-yl-7-trifluoromethyl-pyrazolo[1,5-a]pyrimidine-2-carboxylic acid (5-chloro-2-hydroxy-phenyl)-amide | 438 |
| 5-Thiophen-2-yl-7-trifluoromethyl-pyrazolo[1,5-a]pyrimidine-2-carboxylic acid (3-morpholin-4-yl-propyl)-amide | 439 |
| 3-Bromo-5-thiophen-2-yl-7-trifluoromethyl-pyrazolo[1,5-a]pyrimidine-2-carboxylic acid butylamide | 446 |
| (3-Bromo-5-thiophen-2-yl-7-trifluoromethyl-pyrazolo[1,5-a]pyrimidin-2-yl)-morpholin-4-yl-methanone | 460 |
| (3-Bromo-5-thiophen-2-yl-7-trifluoromethyl-pyrazolo[1,5-a]pyrimidin-2-yl)-(4-methyl-piperazin-1-yl)-methanone | 473 |

-continued

| name | MZ |
|---|---|
| 3-Bromo-5-thiophen-2-yl-7-trifluoromethyl-pyrazolo[1,5-a]pyrimidine-2-carboxylic acid (2-morpholin-4-yl-ethyl)-amide | 503 |
| 3-Bromo-5-thiophen-2-yl-7-trifluoromethyl-pyrazolo[1,5-a]pyrimidine-2-carboxylic acid (2,3-dichloro-phenyl)-amide | 534 |
| 3-Bromo-5-thiophen-2-yl-7-trifluoromethyl-pyrazolo[1,5-a]pyrimidine-2-carboxylic acid cyclohexylamide | 472 |
| 3-Bromo-5-thiophen-2-yl-7-trifluoromethyl-pyrazolo[1,5-a]pyrimidine-2-carboxylic acid [3-nitro-5-(pyridin-3-yloxy)-phenyl]-amide | 604 |
| 3-Bromo-5-thiophen-2-yl-7-trifluoromethyl-pyrazolo[1,5-a]pyrimidine-2-carboxylic acid (3-nitro-5-m-tolyloxy-phenyl)-amide | 617 |
| 5-Furan-2-yl-7-trifluoromethyl-pyrazolo[1,5-a]pyrimidine-2-carboxylic acid amide | 296 |
| 5-Furan-2-yl-7-trifluoromethyl-pyrazolo[1,5-a]pyrimidine-2-carboxylic acid (3-methoxy-5-nitro-phenyl)-amide | 447 |
| 7-Methyl-5-phenyl-pyrazolo[1,5-a]pyrimidine-2-carboxylic acid (2,4-dichloro-phenyl)-amide | 396 |
| 2-[(7-Methyl-5-phenyl-pyrazolo[1,5-a]pyrimidine-2-carbonyl)-amino]-benzoic acid methyl ester | 386 |
| 7-Methyl-5-phenyl-pyrazolo[1,5-a]pyrimidine-2-carboxylic acid (pyridin-3-ylmethyl)-amide | 343 |
| 7-Methyl-5-phenyl-pyrazolo[1,5-a]pyrimidine-2-carboxylic acid (3-hydroxy-phenyl)-amide | 344 |
| 7-Methyl-5-phenyl-pyrazolo[1,5-a]pyrimidine-2-carboxylic acid (5-chloro-2-methoxy-phenyl)-amide | 392 |
| 5,7-Diphenyl-pyrazolo[1,5-a]pyrimidine-2-carboxylic acid (furan-2-ylmethyl)-amide | 394 |
| 5,7-Diphenyl-pyrazolo[1,5-a]pyrimidine-2-carboxylic acid (3-trifluoromethyl-phenyl)-amide | 458 |
| 5,7-Diphenyl-pyrazolo[1,5-a]pyrimidine-2-carboxylic acid cyclopentylamide | 382 |
| 5-[(5,7-Diphenyl-pyrazolo[1,5-a]pyrimidine-2-carbonyl)-amino]-3-methyl-thiophene-2,4-dicarboxylic acid diethyl ester | 554 |
| 5-Acetyl-2-[(5,7-diphenyl-pyrazolo[1,5-a]pyrimidine-2-carbonyl)-amino]-4-methyl-thiophene-3-carboxylic acid ethyl ester | 524 |
| 3-Chloro-5-thiophen-2-yl-7-trifluoromethyl-pyrazolo[1,5-a]pyrimidine-2-carboxylic acid (2-ethyl-phenyl)-amide | 450 |
| 3-Chloro-5-thiophen-2-yl-7-trifluoromethyl-pyrazolo[1,5-a]pyrimidine-2-carboxylic acid (5-chloro-2-hydroxy-phenyl)-amide | 472 |
| 3-Chloro-5-thiophen-2-yl-7-trifluoromethyl-pyrazolo[1,5-a]pyrimidine-2-carboxylic acid cyclohexylamide | 428 |
| 3-Chloro-5-thiophen-2-yl-7-trifluoromethyl-pyrazolo[1,5-a]pyrimidine-2-carboxylic acid (3-hydroxy-phenyl)-amide | 438 |
| 3-Chloro-5-thiophen-2-yl-7-trifluoromethyl-pyrazolo[1,5-a]pyrimidine-2-carboxylic acid isobutyl-amide | 402 |
| 3-Chloro-5-thiophen-2-yl-7-trifluoromethyl-pyrazolo[1,5-a]pyrimidine-2-carboxylic acid benzyl-phenyl-amide | 512 |
| 3-Chloro-5-thiophen-2-yl-7-trifluoromethyl-pyrazolo[1,5-a]pyrimidine-2-carboxylic acid (4-trifluoromethoxy-phenyl)-amide | 506 |
| 3-Chloro-5-thiophen-2-yl-7-trifluoromethyl-pyrazolo[1,5-a]pyrimidine-2-carboxylic acid [3,5-bis-(4-fluoro-phenoxy)-phenyl]-amide | 642 |
| 5-(4-Chloro-phenyl)-7-methyl-pyrazolo[1,5-a]pyrimidine-2-carboxylic acid (3,4-dimethyl-phenyl)-amide | 390 |
| 3-Bromo-5-(4-bromo-thiophen-2-yl)-7-trifluoromethyl-pyrazolo[1,5-a]pyrimidine-2-carboxylic acid (2-chloro-pyridin-3-yl)-amide | 579 |
| 3-Bromo-5-(4-bromo-thiophen-2-yl)-7-trifluoromethyl-pyrazolo[1,5-a]pyrimidine-2-carboxylic acid (5-chloro-2-hydroxy-phenyl)-amide | 594 |
| 5-Thiophen-2-yl-7-trifluoromethyl-pyrazolo[1,5-a]pyrimidine-2-carboxylic acid (4-methyl-2-oxo-2H-chromen-7-yl)-amide | 470 |
| 5-(4-Methoxy-phenyl)-7-trifluoromethyl-pyrazolo[1,5-a]pyrimidine-2-carboxylic acid (2-benzoyl-4-bromo-phenyl)-amide | 594 |
| 2-{[5-(4-Methoxy-phenyl)-7-trifluoromethyl-pyrazolo[1,5-a]pyrimidine-2-carbonyl]-amino}-4,5-dimethyl-thiophene-3-carboxylic acid ethyl ester | 518 |
| 3-Chloro-5-(4-chloro-phenyl)-7-trifluoromethyl-pyrazolo[1,5-a]pyrimidine-2-carboxylic acid (3-morpholin-4-yl-propyl)-amide | 636 |
| 5-(4-Methoxy-phenyl)-7-trifluoromethyl-pyrazolo[1,5-a]pyrimidine-2-carboxylic acid [4-(4-acetyl-phenoxy)-phenyl]-amide | 546 |
| 5-(4-Methoxy-phenyl)-7-trifluoromethyl-pyrazolo[1,5-a]pyrimidine-2-carboxylic acid (2-morpholin-4-yl-ethyl)-amide | 449 |
| 5-(4-Methoxy-phenyl)-7-trifluoromethyl-pyrazolo[1,5-a]pyrimidine-2-carboxylic acid (2-morpholin-4-yl-ethyl)-amide | 491 |
| 3-Bromo-5-(4-methoxyphenyl)-7-trifluoromethyl-pyrazolo[1,5-a]pyrimidine-2-carboxylic acid amide | 414 |
| (3,4-Dihydro-2H-quinolin-1-yl)-(5-phenyl-7-trifluoromethyl-pyrazolo[1,5-a]pyrimidin-2-yl)-methanone | 422 |
| 3-Chloro-5-phenyl-7-trifluoromethyl-pyrazolo[1,5-a]pyrimidine-2-carboxylic acid (4-chloro-2,5-dimethoxy-phenyl)-amide | 510 |

-continued

| name | MZ |
|---|---|
| 5-Thiophen-2-yl-7-trifluoromethyl-pyrazolo[1,5-a]pyrimidine-2-carboxylic acid dibenzylamide | 492 |
| 5-Thiophen-2-yl-7-trifluoromethyl-pyrazolo[1,5-a]pyrimidine-2-carboxylic acid isopropylamide | 354 |
| (7-Methyl-5-phenyl-pyrazolo[1,5-a]pyrimidin-2-yl)-morpholin-4-yl-methanone | 322 |
| 7-Methyl-5-phenyl-pyrazolo[1,5-a]pyrimidine-2-carboxylic acid (furan-2-ylmethyl)-amide | 332 |
| 7-Methyl-5-phenyl-pyrazolo[1,5-a]pyrimidine-2-carboxylic acid (2-methoxy-ethyl)-amide | 310 |
| 7-Methyl-5-phenyl-pyrazolo[1,5-a]pyrimidine-2-carboxylic acid (4-trifluoromethoxy-phenyl)-amide | 412 |
| 7-Methyl-5-phenyl-pyrazolo[1,5-a]pyrimidine-2-carboxylic acid [3-(4-bromo-phenylsulfanyl)-5-nitro-phenyl]-amide | 559 |
| 7-Methyl-5-phenyl-pyrazolo[1,5-a]pyrimidine-2-carboxylic acid [3-(3-diethylamino-phenoxy)-5-nitro-phenyl]-amide | 536 |
| (3-Chloro-5-thiophen-2-yl-7-trifluoromethyl-pyrazolo[1,5-a]pyrimidin-2-yl)-piperidin-1-yl-methanone | 414 |
| 3-Chloro-5-thiophen-2-yl-7-trifluoromethyl-pyrazolo[1,5-a]pyrimidine-2-carboxylic acid (2-hydroxy-5-methyl-phenyl)-amide | 452 |
| 3-Chloro-5-thiophen.2-yl-7-trifluoromethyl-pyrazolo[1,5-a]pyrimidine-2-carboxylic acid (4-ethyl-phenyl)-amide | 450 |
| 3-Chloro-5-thiophen-2-yl-7-trifluoromethyl-pyrazolo[1,5-a]pyrimidine-2-carboxylic acid methyl-(2-pyridin-2-yl-ethyl)-amide | 465 |
| 3-Chloro-5-thiophen-2-yl-7-trifluoromethyl-pyrazolo[1,5-a]pyrimidine-2-carboxylic acid pyridin-4-ylamide | 423 |
| 3-Chloro-5-thiophen-2-yl-7-trifluoromethyl-pyrazolo[1,5-a]pyrimidine-2-carboxylic acid (3-diethylamino-propyl)-amide | 459 |
| 3-Chloro-5-thiophen-2-yl-7-trifluoromethyl-pyrazolo[1,5-a]pyrimidine-2-carboxylic acid (3,4-dimethoxy-phenyl)-amide | 482 |
| 3-Chloro-5-thiophen-2-yl-7-trifluoromethyl-pyrazolo[1,5-a]pyrimidine-2-carboxylic acid cyclohexyl-methyl-amide | 442 |
| 3-Chloro-5-thiophen-2-yl-7-trifluoromethyl-pyrazolo[1,5-a]pyrimidine-2-carboxylic acid (3-cyano-4,5,6,7-tetrahydro-benzo[b]thiophen-2-yl)-amide | 507 |
| 3-Chloro-5-thiophen-2-yl-7-trifluoromethyl-pyrazolo[1,5-a]pyrimidine-2-carboxylic acid [3-(4-bromo-phenoxy)-5-nitro-phenyl]-amide | 637 |
| 2-[(3-Chloro-5-thiophen-2-yl-7-trifluoromethyl-pyrazolo[1,5-a]pyrimidine-2-carbonyl)-amino]-4,5,6,7-tetrahydro-benzo[b]thiophene-3-carboxylic acid ethyl ester | 554 |
| 5-(4-Fluoro-phenyl)-7-trifluoromethyl-pyrazolo[1,5-a]pyrimidine-2-carboxylic acid (4-chloro-phenyl)-amide | 434 |
| 5-(4-Fluoro-phenyl)-7-trifluoromethyl-pyrazolo[1,5-a]pyrimidine-2-carboxylic acid (2,3-dichloro-phenyl)-amide | 468 |
| 2-{[5-(4-Fluoro-phenyl)-7-trifluoromethyl-pyrazolo[1,5-a]pyrimidine-2-carbonyl]-amino}-benzoic acid methyl ester | 458 |
| 5-(4-Fluoro-phenyl)-7-trifluoromethyl-pyrazolo[1,5-a]pyrimidine-2-carboxylic acid (2-morpholin-4-yl-ethyl)-amide | 437 |
| 5-(4-Fluoro-phenyl)-7-trifluoromethyl-pyrazolo[1,5-a]pyrimidine-2-carboxylic acid (3-trifluoromethyl-phenyl)-amide | 468 |
| [5-(4-Fluoro-phenyl)-7-trifluoromethyl-pyrazolo[1 5-a]pyrimidin-2-yl]-(4-phenyl-piperazin-1-yl)-methanone | 469 |
| Azepan-1-yl-[5-(4-fluoro-phenyl)-7-trifluoromethyl-pyrazolo[1,5-a]pyrimidin-2-yl]-methanone | 406 |
| 5-(4-Fluoro-phenyl)-7-trifluoromethyl-pyrazolo[1,5-a]pyrimidine-2-carboxylic acid benzo[1,3]dioxol-5-ylamide | 444 |
| [5-(3,4-Dimethoxy-phenyl)-7-trifluoromethyl-pyrazolo[1,5-a]pyrimidin-2-yl]-morpholin-4-yl-methanone | 436 |
| 5-Acetyl-2-{[5-(3,4-dimethoxy-phenyl)-7-trifluoromethyl-pyrazolo[1,5-a]pyrimidine-2-carbonyl]-amino}-4-methyl-thiophene-3-carboxylic acid ethyl ester | 576 |
| (4-Benzhydryl-piperazin-1-yl)-[5-(4-methoxy-phenyl)-7-trifluoromethyl-pyrazolo[1,5-a]pyrimidin-2-yl]-methanone | 571 |
| (4-Benzyl-piperazin-1-yl)-[5-(4-methoxy-phenyl)-7-trifluoromethyl-pyrazolo[1,5-a]pyrimidin-2-yl]-methanone | 495 |
| 5-(4-Methoxy-phenyl)-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 522 |
| 6-tert-Butyl-2-[(3-chloro-5-phenyl-7-trifluoromethyl-pyrazolo[1,5-a]pyrimidine-2-carbonyl)-amino]-4,5,6,7-tetrahydro-benzo[b]thiophene-3-carboxylic acid methyl ester | 590 |
| 2-[(3-Bromo-5-phenyl-7-trifluoromethyl-pyrazolo[1,5-a]pyrimidine-2-carbonyl)-amino]-6-methyl-4,5,6,7-tetrahydro-benzo[b]thiophene-3-carboxylic acid ethyl ester | 606 |
| 3-Bromo-5-phenyl-7-trifluoromethyl-pyrazolo[1,5-a]pyrimidine-2-carboxylic acid cyanomethyl-amide | 423 |

-continued

| name | MZ |
|---|---|
| 2-[(5-Furan-2-yl-7-trifluoromethyl-pyrazolo[1,5-a]pyrimidine-2-carbonyl)-amino]-4,5,6,7-tetrahydro-benzo[b]thiophene-3-carboxylic acid methyl ester | 490 |
| 2-[(5-Furan-2-yl-7-trifluoromethyl-pyrazolo[1,5-a]pyrimidine-2-carbonyl)-amino]-6-methyl-4,5,6,7-tetrahydro-benzo[b]thiophene-3-carboxylic acid ethyl ester | 518 |
| 2-[(5-Furan-2-yl-7-trifluoromethyl-pyrazolo[1,5-a]pyrimidine-2-carbonyl)-amino]-6-methyl-4,5,6,7-tetrahydro-benzo[b]thiophene-3-carboxylic acid ethyl ester | 612 |
| 6-tert-Butyl-2-[(3-chloro-5-thiophen-2-yl-7-trifluoromethyl-pyrazolo[1,5-a]pyrimidine-2-carbonyl)-amino]-4,5,6,7-tetrahydro-benzo[b]thiophene-3-carboxylic acid methyl ester | 596 |
| 2-[(3-Chloro-5-thiophen-2-yl-7-trifluoromethyl-pyrazolo[1,5-a]pyrimidine-2-carbonyl)-amino]-6-methyl-4,5,6,7-tetrahydro-benzo[b]thiophene-3-carboxylic acid ethyl ester | 568 |
| 3-Chloro-5-thiophen-2-yl-7-trifluoromethyl-pyrazolo[1,5-a]pyrimidine-2-carboxylic acid (3-cyano-5,6,7,8-tetrahydro-4H-cyclohepta[b]thiophen-2-yl)-amide | 521 |
| (3-Chloro-5-thiophen-2-yl-7-trifluoromethyl-pyrazolo[1,5-a]pyrimidin-2-yl)-(3,4-dihydro-1H-isoquinolin-2-yl)-methanone | 462 |
| 2-[(5-Thiophen-2-yl-7-trifluoromethyl-pyrazolo[1,5-a]pyrimidine-2-carbonyl)-amino]-5,6-dihydro-4H-cyclopenta[b]thiophene-3-carboxylic acid ethyl ester | 506 |
| 5-Thiophen-2-yl-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide | 529 |
| 5-Thiophen-2-yl-7-trifluoromethyl-pyrazolo[1,5-a]pyrimidine-2-carboxylic acid adamantan-1-ylamide | 446 |
| [5(4-Bromo-phenyl)-7-trifluoromethyl-pyrazolo[1,5-a]pyrimidin-2-yl]-morpholin-4-yl-methanone | 454 |
| 5-(4-Bromo-phenyl)-7-trifluoromethyl-pyrazolo[1,5-a]pyrimidine-2-carboxylic acid (2,4-dichloro-phenyl)-amide | 528 |
| 5-(4-Bromo-phenyl)-7-trifluoromethyl-pyrazolo[1,5-a]pyrimidine-2-carboxylic acid (5-chloro-2-hydroxy-phenyl)-amide | 510 |
| 5-(4-Bromo-phenyl)-7-trifluoromethyl-pyrazolo[1,5-a]pyrimidine-2-carboxylic acid (2-hydroxy-5-methyl-phenyl)-amide | 490 |
| 5-(4-Bromo-phenyl)-7-trifluoromethyl-pyrazolo[1,5-a]pyrimidine-2-carboxylic acid (4-acetyl-phenyl)-amide | 502 |
| 5-(4-Bromo-phenyl)-7-trifluoromethyl-pyrazolo[1,5-a]pyrimidine-2-carboxylic acid (3,4-dimethyl-phenyl)-amide | 488 |
| 5-(4-Bromo-phenyl)-7-trifluoromethyl-pyrazolo[1,5-a]pyrimidine-2-carboxylic acid (2-trifluoromethyl-phenyl)-amide | 528 |
| 5-(4-Bromo-phenyl)-7-trifluoromethyl-pyrazolo[1,5-a]pyrimidine-2-carboxylic acid naphthalen-1-ylamide | 510 |
| (4-Benzhydryl-piperazin-1-yl)-[5-(4-bromo-phenyl)-7-trifluoromethyl-pyrazolo[1,5-a]pyrimidin-2-yl]-methanone | 619 |
| Azepan-1-yl-[5-(4-bromo-phenyl)-7-trifluoromethyl-pyrazolo[1,5-a]pyrimidin-2-yl]-methanone | 466 |
| 5-(4-Bromo-phenyl)-7-trifluoromethyl-pyrazolo[1,5-a]pyrimidine-2-carboxylic acid benzo[1,3]dioxol-4-ylamide | 504 |
| 5-(4-Bromo-phenyl)-7-trifluoromethyl-pyrazolo[1,5-a]pyrimidine-2-carboxylic acid (4-chloro-2,5-dimethoxy-phenyl)-amide | 554 |
| 5-Acetyl-2-{[5-(4-bromo-phenyl)-7-trifluoromethyl-pyrazolo[1,5-a]pyrimidine-2-carbonyl]-amino}-4-methyl-thiophene-3-carboxylic acid ethyl ester | 594 |
| 5-(4-Bromo-phenyl)-7-trifluoromethyl-pyrazolo[1,5-a]pyrimidine-2-carboxylic acid (6-methyl-pyridin-2-yl)-amide | 475 |
| 5-(4-Bromo-phenyl)-7-trifluoromethyl-pyrazolo[1,5-a]pyrimidine-2-carboxylic acid pyridin-3-ylamide | 461 |
| 5-(4-Bromo-phenyl)-7-trifluoromethyl-pyrazolo[1,5-a]pyrimidine-2-carboxylic acid [3-nitro-5-(pyridin-3-yloxy)-phenyl]-amide | 598 |
| 5-(4-Bromo-phenyl)-7-trifluoromethyl-pyrazolo[1,5-a]pyrimidine-2-carboxylic acid (4-chloro-3-fluoro-phenyl)-amide | 512 |
| 5-(4-Bromo-phenyl)-3-chloro-7-trifluoromethyl-pyrazolo[1,5-a]pyrimidine-2-carboxylic acid amide | 418 |
| 5-(4-Bromo-phenyl)-3-chloro-7-trifluoromethyl-pyrazolo[1,5-a]pyrimidine-2-carboxylic acid (3-chloro-2-methyl-phenyl)-amide | 542 |
| (4-Benzhydryl-piperazin-1-yl)-[5-(4-bromo-phenyl)-3-chloro-7-trifluoromethyl-pyrazolo[1,5-a]pyrimidin-2-yl]-methanone | 653 |
| 5-(4-Bromo-phenyl)-3-chloro-7-trifluoromethyl-pyrazolo[1,5-a]pyrimidine-2-carboxylic acid (3-imidazol-1-yl-propyl)-amide | 526 |
| 5-(4-Bromo-phenyl)-3-chloro-7-trifluoromethyl-pyrazolo[1,5-a]pyrimidine-2-carboxylic acid (4-chloro-2,5-dimethoxy-phenyl)-amide | 588 |
| 2-{[5-(4-Bromo-phenyl)-3-chloro-7-trifluoromethyl-pyrazolo[1,5-a]pyrimidine-2-carbonyl]-amino}-4,5,6,7-tetrahydro-benzo[b]thiophene-3-carboxylic acid ethyl ester | 626 |

| name | MZ |
|---|---|
| 5-Acetyl-2-{[5-(4-bromo-phenyl)-3-chloro-7-trifluoromethyl-pyrazolo[1,5-a]pyrimidine-2-carbonyl]-amino}-4-methyl-thiophene-3-carboxylic acid ethyl ester | 628 |
| 5-(4-Bromo-phenyl)-3-chloro-7-trifluoromethyl-pyrazolo[1,5-a]pyrimidine-2-carboxylic acid (5-bromo-pyridin-2-yl)-amide | 573 |
| [5-(4-Bromo-phenyl)-3-chloro-7-trifluoromethyl-pyrazolo[1,5-a]pyrimidin-2-yl]-[4-(2-methoxy-phenyl)-piperazin-1-yl]-methanone | 593 |
| [3-Bromo-5-(4-bromo-phenyl)-7-trifluoromethyl-pyrazolo[1,5-a]pyrimidin-2-yl]-piperidin-1-yl-methanone | 530 |
| [3-Bromo-5-(4-bromo-phenyl)-7-trifluoromethyl-pyrazolo[1,5-a]pyrimidin-2-yl]-(4-methyl-piperazin-1-yl)-methanone | 545 |
| (4-Benzyl-piperazin-1-yl)-[3-bromo-5-(4-bromo-phenyl)-7-trifluoromethyl-pyrazolo[1,5-a]pyrimidin-2-yl]-methanone | 621 |
| 3-Bromo-5-(4-bromo-phenyl)-7-trifluoromethyl-pyrazolo[1,5-a]pyrimidine-2-carboxylic acid (2,4-difluoro-phenyl)-amide | 574 |
| 5-(4-Nitro-phenyl)-7-trifluoromethyl-pyrazolo[1,5-a]pyrimidine-2-carboxylic acid cyclopentylamide | 419 |
| Azepan-1-yl-[5-(4-nitro-phenyl)-7-trifluoromethyl-pyrazolo[1,5-a]pyrimidin-2-yl]-methanone | 433 |
| 5-(4-Nitro-phenyl)-7-trifluoromethyl-pyrazolo[1,5-a]pyrimidine-2-carboxylic acid (3-imidazol-1-yl-propyl)-amide | 459 |
| 5-(4-Nitro-phenyl)-7-trifluoromethyl-pyrazolo[1,5-a]pyrimidine-2-carboxylic acid cyclohexyl-methyl-amide | 447 |
| 3-Methyl-5-{[5-(4-nitro-phenyl)-7-trifluoromethyl-pyrazolo[1,5-a]pyrimidine-2-carbonyl]-amino}-thiophene-2,4-dicarboxylic acid dimethyl ester | 563 |
| (3,4-Dihydro-1H-isoquinolin-2-yl)-[5-(4-nitro-phenyl)-7-trifluoromethyl-pyrazolo[1,5-a]pyrimidin-2-yl]-methanone | 467 |
| 5-(3,4-Dichloro-phenyl)-7-trifluoromethyl-pyrazolo[1,5-a]pyrimidine-2-carboxylic acid cyclohexylamide | 456 |
| 2-{[5-(3,4-Dichloro-phenyl)-7-trifluoromethyl-pyrazolo[1,5-a]pyrimidine-2-carbonyl]-amino}-4,5,6,7-tetrahydro-benzo[b]thiophene-3-carboxylic acid ethyl ester | 582 |
| 5-Phenyl-7-trifluoromethyl-pyrazolo[1,5-a]pyrimidine-2-carboxylic acid (2,4-dichloro-phenyl)-amide | 450 |
| 3-Bromo-5-(4-bromo-phenyl)-7-trifluoromethyl-pyrazolo[1,5-a]pyrimidine-2-carboxylic acid (3,4-dichloro-phenyl)-amide | 606 |
| 3-Chloro-5-thiophen-2-yl-7-trifluoromethyl-pyrazolo[1,5-a]pyrimidine-2-carboxylic acid (5-chloro-2-methoxy-phenyl)-amide | 486 |
| 3-Chloro-5-thiophen-2-yl-7-trifluoromethyl-pyrazolo[1,5-a]pyrimidine-2-carboxylic acid benzo[1,3]dioxol-5-ylamide | 466 |
| 5-Phenyl-7-trifluoromethyl-pyrazolo[1,5-a]pyrimidine-2-carboxylic acid (2,3-dichloro-phenyl)-amide | 450 |
| 5-Phenyl-7-trifluoromethyl-pyrazolo[1,5-a]pyrimidine-2-carboxylic acid (3-chloro-4-fluoro-phenyl)-amide | 434 |
| 3-Chloro-5-phenyl-7-trifluoromethyl-pyrazolo[1,5-a]pyrimidine-2-carboxylic acid (3-chloro-phenyl)-amide | 450 |
| 3-Chloro-5-phenyl-7-trifluoromethyl-pyrazolo[1,5-a]pyrimidine-2-carboxylic acid (2-trifluoromethyl-phenyl)-amide | 484 |
| 3-Chloro-5-phenyl-7-trifluoromethyl-pyrazolo[1,5-a]pyrimidine-2-carboxylic acid (4-cyano-phenyl)-amide | 441 |
| 3-Chloro-5-phenyl-7-trifluoromethyl-pyrazolo[1,5-a]pyrimidine-2-carboxylic acid (2-bromo-phenyl)-amide | 494 |
| 3-Bromo-5-phenyl-7-trifluoromethyl-pyrazolo[1,5-a]pyrimidine-2-carboxylic acid (3,4-dichloro-phenyl)-amide | 528 |
| 3-Bromo-5-phenyl-7-trifluoromethyl-pyrazolo[1,5-a]pyrimidine-2-carboxylic acid (3-chloro-phenyl)-amide | 494 |
| 3-Bromo-5-phenyl-7-trifluoromethyl-pyrazolo[1,5-a]pyrimidine-2-carboxylic acid (5-chloro-2-hydroxy-phenyl)-amide | 510 |
| 3-Bromo-5-phenyl-7-trifluoromethyl-pyrazolo[1,5-a]pyrimidine-2-carboxylic acid (3-chloro-4-fluoro-phenyl)-amide | 512 |
| 3-Bromo-5-phenyl-7-trifluoromethyl-pyrazolo[1,5-a]pyrimidine-2-carboxylic acid (3-chloro-5-trifluoromethyl-pyridin-2-yl)-amide | 563 |
| 3-Bromo-5-phenyl-7-trifluoromethyl-pyrazolo[1,5-a]pyrimidine-2-carboxylic acid (4-bromo-phenyl)-amide | 538 |
| 3-Bromo-5-phenyl-7-trifluoromethyl-pyrazolo[1,5-a]pyrimidine-2-carboxylic acid (2-bromo-phenyl)-amide | 538 |
| 5-Phenyl-7-trifluoromethyl-pyrazolo[1,5-a]pyrimidine-2-carboxylic acid (2-bromo-4,6-difluoro-phenyl)-amide | 496 |
| 3-Chloro-5-phenyl-7-trifluoromethyl-pyrazolo[1,5-a]pyrimidine-2-carboxylic acid 4-chloro-benzylamide | 464 |
| 3-Chloro-5-phenyl-7-trifluoromethyl-pyrazolo[1,5-a]pyrimidine-2-carboxylic acid (4-trifluoromethoxy-phenyl)-amide | 500 |
| 3-Bromo-5-phenyl-7-trifluoromethyl-pyrazolo[1,5-a]pyrimidine-2-carboxylic acid (4-trifluoromethoxy-phenyl)-amide | 544 |
| 5-Thiophen-2-yl-7-trifluoromethyl-pyrazolo[1,5-a]pyrimidine-2-carboxylic acid (3,4-dichloro-phenyl)-amide | 456 |

-continued

| name | MZ |
|---|---|
| 5-Thiophen-2-yl-7-trifluoromethyl-pyrazolo[1,5-a]pyrimidine-2-carboxylic acid (2,4-dichloro-phenyl)-amide | 456 |
| 5-Thiophen-2-yl-7-trifluoromethyl-pyrazolo[1,5-a]pyrimidine-2-carboxylic acid [4-(3,5-dinitro-phenoxy)-phenyl]-amide | 570 |
| 5-Thiophen-2-yl-7-trifluoromethyl-pyrazolo[1,5-a]pyrimidine-2-carboxylic acid (2-chloro-5-trifluoromethyl-phenyl)-amide | 490 |
| 5-Thiophen-2-yl-7-trifluoromethyl-pyrazolo[1,5-a]pyrimidine-2-carboxylic acid [3-(3-chloro-phenoxy)-5-nitro-phenyl]-amide | 559 |
| 5-Thiophen-2-yl-7-trifluoromethyl-pyrazolo[1,5-a]pyrimidine-2-carboxylic acid (2,3-dichloro-phenyl)-amide | 456 |
| 5-Thiophen-2-yl-7-trifluoromethyl-pyrazolo[1,5-a]pyrimidine-2-carboxylic acid (2-bromo-4,6-difluoro-phenyl)-amide | 502 |
| 5-Thiophen-2-yl-7-trifluoromethyl-pyrazolo[1,5-a]pyrimidine-2-carboxylic acid (5-chloro-2-methoxy-phenyl)-amide | 452 |
| 5-Thiophen-2-yl-7-trifluoromethyl-pyrazolo[1,5-a]pyrimidine-2-carboxylic acid (3-chloro-4-fluoro-phenyl)-amide | 440 |
| 3-Bromo-5-thiophen-2-yl-7-trifluoromethyl-pyrazolo[1,5-a]pyrimidine-2-carboxylic acid (3,4-dichloro-phenyl)-amide | 534 |
| 3-Bromo-5-thiophen-2-yl-7-trifluoromethyl-pyrazolo[1,5-a]pyrimidine-2-carboxylic acid (2,4-dichloro-phenyl)-amide | 534 |
| 3-Bromo-5-thiophen-2-yl-7-trifluoromethyl-pyrazolo[1,5-a]pyrimidine-2-carboxylic acid (4-bromo-phenyl)-amide | 544 |
| 3-Bromo-5-thiophen-2-yl-7-trifluoromethyl-pyrazolo[1,5-a]pyrimidine-2-carboxylic acid (2-methylsulfanyl-phenyl)-amide | 512 |
| 5-Furan-2-yl-7-trifluoromethyl-pyrazolo[1,5-a]pyrimidine-2-carboxylic acid [3-(4-fluoro-phenoxy)-5-nitro-phenyl]-amide | 527 |
| 5-Furan-2-yl-7-trifluoromethyl-pyrazolo[1,5-a]pyrimidine-2-carboxylic acid (2-chloro-5-trifluoromethyl-phenyl)-amide | 474 |
| 5-Furan-2-yl-7-trifluoromethyl-pyrazolo[1,5-a]pyrimidine-2-carboxylic acid (3,4-dichloro-phenyl)-amide | 440 |
| 5-Furan-2-yl-7-trifluoromethyl-pyrazolo[1,5-a]pyrimidine-2-carboxylic acid (2,4-dichloro-phenyl)-amide | 440 |
| 5-Furan-2-yl-7-trifluoromethyl-pyrazolo[1,5-a]pyrimidine-2-carboxylic acid (2,5-dichloro-phenyl)-amide | 440 |
| 3-Bromo-5-(4-bromo-thiophen-2-yl)-7-trifluoromethyl-pyrazolo[1,5-a]pyrimidine-2-carboxylic acid (furan-2-ylmethyl)-amide | 548 |
| 3-Bromo-5-(4-bromo-thiophen-2-yl)-7-trifluoromethyl-pyrazolo[1,5-a]pyrimidine-2-carboxylic acid (4-trifluoromethoxy-phenyl)-amide | 628 |
| 3-Bromo-5-(4-bromo-thiophen-2-yl)-7-trifluoromethyl-pyrazolo[1,5-a]pyrimidine-2-carboxylic acid (3,4-dichloro-phenyl)-amide | 612 |
| 3-Bromo-5-phenyl-7-trifluoromethyl-pyrazolo[1,5-a]pyrimidine-2-carboxylic acid (2,4-dichloro-phenyl)-amide | 528 |
| 5-Phenyl-7-trifluoromethyl-pyrazolo[1,5-a]pyrimidine-2-carboxylic acid (3,4-dichloro-phenyl)-amide | 450 |
| 3-Chloro-5-phenyl-7-trifluoromethyl-pyrazolo[1,5-a]pyrimidine-2-carboxylic acid (4-chloro-phenyl)-amide | 450 |
| 3-Chloro-5-phenyl-7-trifluoromethyl-pyrazolo[1,5-a]pyrimidine-2-carboxylic acid (3,4-dichloro-phenyl)-amide | 484 |
| 3-Chloro-5-phenyl-7-trifluoromethyl-pyrazolo[1,5-a]pyrimidine-2-carboxylic acid (3-chloro-2-methyl-phenyl)-amide | 464 |
| 3-Chloro-5-phenyl-7-trifluoromethyl-pyrazolo[1,5-a]pyrimidine-2-carboxylic acid (4-bromo-phenyl)-amide | 494 |
| 3-Bromo-5-phenyl-7-trifluoromethyl-pyrazolo[1,5-a]pyrimidine-2-carboxylic acid (4-cyano-phenyl)-amide | 485 |
| 5-Thiophen-2-yl-7-trifluoromethyl-pyrazolo[1,5-a]pyrimidine-2-carboxylic acid (3-methoxy-5-nitro-phenyl)-amide | 463 |
| 3-Bromo-5-thiophen-2-yl-7-trifluoromethyl-pyrazolo[1,5-a]pyrimidine-2-carboxylic acid (3-chloro-phenyl)-amide | 500 |
| 3-Bromo-5-thiophen-2-yl-7-trifluoromethyl-pyrazolo[1,5-a]pyrimidine-2-carboxylic acid (5-chloro-2-hydroxy-phenyl)-amide | 516 |
| 3-Bromo-5-thiophen-2-yl-7-trifluoromethyl-pyrazolo[1,5-a]pyrimidine-2-carboxylic acid (2,5-dichloro-phenyl)-amide | 534 |
| 3-Bromo-5-thiophen-2-yl-7-trifluoromethyl-pyrazolo[1,5-a]pyrimidine-2-carboxylic acid (2-hydroxy-5-methyl-phenyl)-amide | 496 |
| 3-Bromo-5-thiophen-2-yl-7-trifluoromethyl-pyrazolo[1,5-a]pyrimidine-2-carboxylic acid (3-chloro-4-fluoro-phenyl)-amide | 518 |
| 3-Bromo-5-thiophen-2-yl-7-trifluoromethyl-pyrazolo[1,5-a]pyrimidine-2-carboxylic acid (2-bromo-4,6-difluoro-phenyl)-amide | 580 |
| 3-Chloro-5-thiophen-2-yl-7-trifluoromethyl-pyrazolo[1,5-a]pyrimidine-2-carboxylic acid (4-chloro-phenyl)-amide | 456 |
| 3-Chloro-5-thiophen-2-yl-7-trifluoromethyl-pyrazolo[1,5-a]pyrimidine-2-carboxylic acid (3,4-dichloro-phenyl)-amide | 490 |
| 3-Chloro-5-thiophen-2-yl-7-trifluoromethyl-pyrazolo[1,5-a]pyrimidine-2-carboxylic acid (2,4-dichloro-phenyl)-amide | 490 |
| 3-Chloro-5-thiophen-2-yl-7-trifluoromethyl-pyrazolo[1,5-a]pyrimidine-2-carboxylic acid (3-chloro-4-fluoro-phenyl)-amide | 474 |

-continued

| name | MZ |
|---|---|
| 3-Chloro-5-thiophen-2-yl-7-trifluoromethyl-pyrazolo[1,5-a]pyrimidine-2-carboxylic acid (2-chloro-5-trifluoromethyl-phenyl)-amide | 524 |
| 3-Chloro-5-thiophen-2-yl-7-trifluoromethyl-pyrazolo[1 5-a]pyrimidine-2-carboxylic acid (2-bromo-4,6-difluoro-phenyl)-amide | 536 |
| 3-Chloro-5-thiophen-2-yl-7-trifluoromethyl-pyrazolo[1,5-a]pyrimidine-2-carboxylic acid (2-methylsulfanyl-phenyl)-amide | 468 |
| 3-Chloro-5-thiophen-2-yl-7-trifluoromethyl-pyrazolo[1,5-a]pyrimidine-2-carboxylic acid (3-methoxy-5-nitro-phenyl)-amide | 497 |
| 3-Chloro-5-thiophen-2-yl-7-trifluoromethyl-pyrazolo[1,5-a]pyrimidine-2-carboxylic acid (3-hydroxy-5-nitro-phenyl)-amide | 483 |
| 3-Bromo-5-(4-bromo-thiophen-2-yl)-7-trifluoromethyl-pyrazolo[1,5-a]pyrimidine-2-carboxylic acid (4-chloro-phenyl)-amide | 578 |
| 3-Bromo-5-(4-bromo-thiophen-2-yl)-7-trifluoromethyl-pyrazolo[1,5-a]pyrimidine-2-carboxylic acid (4-chloro-2-methoxy-phenyl)-amide | 608 |
| 3-Bromo-5-(4-bromo-thiophen-2-yl)-7-trifluoromethyl-pyrazolo[1,5-a]pyrimidine-2-carboxylic acid (3,4-dimethyl-phenyl)-amide | 572 |
| 3-Chloro-5-thiophen-2-yl-7-trifluoromethyl-pyrazolo[1,5-a]pyrimidine-2-carboxylic acid (2,3-dichloro-phenyl)-amide | 490 |
| 3-Bromo-5-(4-bromo-thiophen-2-yl)-7-trifluoromethyl-pyrazolo[1,5-a]pyrimidine-2-carboxylic acid (2-bromo-4,6-difluoro-phenyl)-amide | 658 |
| 3-Bromo-5-(4-bromo-thiophen-2-yl)-7-trifluoromethyl-pyrazolo[1,5-a]pyrimidine-2-carboxylic acid (2-hydroxy-5-methyl-phenyl)-amide | 574 |
| 5-Benzo[1,3]dioxol-5-yl-7-trifluoromethyl-pyrazolo[1,5-a]pyrimidine-2-carboxylic acid (4-chloro-phenyl)-amide | 460 |
| 5-Thiophen-2-yl-7-trifluoromethyl-pyrazolo[1,5-a]pyrimidine-2-carboxylic acid benzo[1,2,5]thiadiazol-4-ylamide | 446 |
| 5-Thiophen-2-yl-7-trifluoromethyl-pyrazolo[1,5-a]pyrimidine-2-carboxylic acid (7-nitro-2,3-dihydro-benzo[1,4]dioxin-6-yl)-amide | 491 |
| 3-Bromo-5-phenyl-7-trifluoromethyl-pyrazolo[1,5-a]pyrimidine-2-carboxylic acid (5-bromo-pyridin-2-yl)-amide | 539 |
| 5-Phenyl-7-trifluoromethyl-pyrazolo[1,5-a]pyrimidine-2-carboxylic acid (5-chloro-2-hydroxy-phenyl)-amide | 432 |
| 3-Chloro-5-phenyl-7-trifluoromethyl-pyrazolo[1,5-a]pyrimidine-2-carboxylic acid (5-chloro-2-methoxy-phenyl)-amide | 480 |
| 3-Bromo-5-thiophen-2-yl-7-trifluoromethyl-pyrazolo[1,5-a]pyrimidine-2-carboxylic acid (4-cyano-phenyl)-amide | 491 |
| 3-Bromo-5-thiophen-2-yl-7-trifluoromethyl-pyrazolo[1,5-a]pyrimidine-2-carboxylic acid (4-trifluoromethoxy-phenyl)-amide | 550 |
| 3-Chloro-5-thiophen-2-yl-7-trifluoromethyl-pyrazolo[1,5-a]pyrimidine-2-carboxylic acid (3-chloro-phenyl)-amide | 456 |
| 3-Chloro-5-thiophen-2-yl-7-trifluoromethyl-pyrazolo[1,5-a]pyrimidine-2-carboxylic acid (3-chloro-2-methyl-phenyl)-amide | 470 |
| 3-Chloro-5-thiophen-2-yl-7-trifluoromethyl-pyrazolo[1,5-a]pyrimidine-2-carboxylic acid (2-trifluoromethyl-phenyl)-amide | 490 |
| 3-Chloro-5-thiophen-2-yl-7-trifluoromethyl-pyrazolo[1,5-a]pyrimidine-2-carboxylic acid (3-acetyl-phenyl)-amide | 464 |
| 5-(4-Fluoro-phenyl)-7-trifluoromethyl-pyrazolo[1,5-a]pyrimidine-2-carboxylic acid (3,4-dichloro-phenyl)-amide | 468 |
| 5-(4-Fluoro-phenyl)-7-trifluoromethyl-pyrazolo[1,5-a]pyrimidine-2-carboxylic acid (3-chloro-phenyl)-amide | 434 |
| 5-(4-Fluoro-phenyl)-7-trifluoromethyl-pyrazolo[1,5-a]pyrimidine-2-carboxylic acid (2,4-dichloro-phenyl)-amide | 468 |
| 5-(4-Fluoro-phenyl)-7-trifluoromethyl-pyrazolo[1,5-a]pyrimidine-2-carboxylic acid (2-trifluoromethyl-phenyl)-amide | 468 |
| 5-(4-Fluoro-phenyl)-7-trifluoromethyl-pyrazolo[1,5-a]pyrimidine-2-carboxylic acid (2-chloro-pyridin-3-yl)-amide | 435 |
| 5-(4-Fluoro-phenyl)-7-trifluoromethyl-pyrazolo[1,5-a]pyrimidine-2-carboxylic acid (2-bromo-4,6-difluoro-phenyl)-amide | 514 |
| 5-(4-Methoxy-phenyl)-7-trifluoromethyl-pyrazolo[1,5-a]pyrimidine-2-carboxylic acid (3,4-dichloro-phenyl)-amide | 480 |
| 5-(4-Bromo-phenyl)-7-trifluoromethyl-pyrazolo[1,5-a]pyrimidine-2-carboxylic acid (4-chloro-phenyl)-amide | 494 |
| 5-(4-Bromo-phenyl)-7-trifluoromethyl-pyrazolo[1,5-a]pyrimidine-2-carboxylic acid (3,4-dichloro-phenyl)-amide | 528 |
| 5-(4-Bromo-phenyl)-7-trifluoromethyl-pyrazolo[1,5-a]pyrimidine-2-carboxylic acid (3-chloro-phenyl)-amide | 494 |
| 5-(4-Bromo-phenyl)-7-trifluoromethyl-pyrazolo[1,5-a]pyrimidine-2-carboxylic acid (2,5-dichloro-phenyl)-amide | 528 |
| 5-(4-Bromo-phenyl)-7-trifluoromethyl-pyrazolo[1,5-a]pyrimidine-2-carboxylic acid (2,3-dichloro-phenyl)-amide | 528 |
| 5-(4-Bromo-phenyl)-7-trifluoromethyl-pyrazolo[1,5-a]pyrimidine-2-carboxylic acid (3-chloro-2-methyl-phenyl)-amide | 508 |
| 2-{[5-(4-Bromo-phenyl)-7-trifluoromethyl-pyrazolo[1,5-a]pyrimidine-2-carbonyl]-amino}-benzoic acid methyl ester | 518 |
| 5-(4-Bromo-phenyl)-7-trifluoromethyl-pyrazolo[1,5-a]pyrimidine-2-carboxylic acid (3-trifluoromethyl-phenyl)-amide | 528 |

-continued

| name | MZ |
|---|---|
| 5-(4-Bromo-phenyl)-7-trifluoromethyl-pyrazolo[1,5-a]pyrimidine-2-carboxylic acid (4-bromo-phenyl)-amide | 538 |
| 5-(4-Bromo-phenyl)-7-trifluoromethyl-pyrazolo[1,5-a]pyrimidine-2-carboxylic acid (2-methylsulfanyl-phenyl)-amide | 506 |
| 5-(4-Bromo-phenyl)-7-trifluoromethyl-pyrazolo[1,5-a]pyrimidine-2-carboxylic acid (2-chloro-5-trifluoromethyl-phenyl)-amide | 562 |
| 5-(4-Bromo-phenyl)-7-trifluoromethyl-pyrazolo[1,5-a]pyrimidine-2-carboxylic acid (4-trifluoromethoxy-phenyl)-amide | 544 |
| 5-(4-Bromo-phenyl)-7-trifluoromethyl-pyrazolo[1,5-a]pyrimidine-2-carboxylic acid (2-bromo-4,6-difluoro-phenyl)-amide | 574 |
| 5-(4-Bromo-phenyl)-7-trifluoromethyl-pyrazolo[1,5-a]pyrimidine-2-carboxylic acid (3-acetyl-phenyl)-amide | 502 |
| 5-(4-Bromo-phenyl)-7-trifluoromethyl-pyrazolo[1,5-a]pyrimidine-2-carboxylic acid (2,4-difluoro-phenyl)-amide | 496 |
| 5-(4-Bromo-phenyl)-7-trifluoromethyl-pyrazolo[1,5-a]pyrimidine-2-carboxylic acid (2-chloro-pyridin-3-yl)-amide | 495 |
| 5-(4-Bromo-phenyl)-7-trifluoromethyl-pyrazolo[1,5-a]pyrimidine-2-carboxylic acid (5-bromo-pyridin-2-yl)-amide | 539 |
| 5-(4-Bromo-phenyl)-7-trifluoromethyl-pyrazolo[1,5-a]pyrimidine-2-carboxylic acid (5-chloro-pyridin-2-yl)-amide | 495 |
| 5-(4-Bromo-phenyl)-7-trifluoromethyl-pyrazolo[1,5-a]pyrimidine-2-carboxylic acid (2,6-dichloro-phenyl)-amide | 528 |
| 5-(4-Bromo-phenyl)-7-trifluoromethyl-pyrazolo[1,5-a]pyrimidine-2-carboxylic acid (3-methoxy-5-nitro-phenyl)-amide | 535 |
| 5-(4-Bromo-phenyl)-7-trifluoromethyl-pyrazolo[1,5-a]pyrimidine-2-carboxylic acid (3-methoxy-5-nitro-phenyl)-amide | 615 |
| 5-(4-Bromo-phenyl)-7-trifluoromethyl-pyrazolo[1,5-a]pyrimidine-2-carboxylic acid [3-(4-bromo-phenoxy)-5-nitro-phenyl]-amide | 675 |
| 5-(4-Bromo-phenyl)-7-trifluoromethyl-pyrazolo[1,5-a]pyrimidine-2-carboxylic acid (2-chloro-4-nitro-phenyl)-amide | 539 |
| 5-(4-Bromo-phenyl)-3-chloro-7-trifluoromethyl-pyrazolo[1,5-a]pyrimidine-2-carboxylic acid (furan-2-ylmethyl)-amide | 498 |
| 5-(4-Bromo-phenyl)-3-chloro-7-trifluoromethyl-pyrazolo[1,5-a]pyrimidine-2-carboxylic acid benzylamide | 508 |
| 5-(4-Bromo-phenyl)-3-chloro-7-trifluoromethyl-pyrazolo[1,5-a]pyrimidine-2-carboxylic acid (4-chloro-phenyl)-amide | 528 |
| 5-(4-Bromo-phenyl)-3-chloro-7-trifluoromethyl-pyrazolo[1,5-a]pyrimidine-2-carboxylic acid (3,4-dichloro-phenyl)-amide | 562 |
| 5-(4-Bromo-phenyl)-3-chloro-7-trifluoromethyl-pyrazolo[1,5-a]pyrimidine-2-carboxylic acid (3-chloro-phenyl)-amide | 528 |
| 5-(4-Bromo-phenyl)-3-chloro-7-trifluoromethyl-pyrazolo[1,5-a]pyrimidine-2-carboxylic acid (2,4-dichloro-phenyl)-amide | 562 |
| 5-(4-Bromo-phenyl)-3-chloro-7-trifluoromethyl-pyrazolo[1,5-a]pyrimidine-2-carboxylic acid (2,5-dichloro-phenyl)-amide | 562 |
| 5-(4-Bromo-phenyl)-3-chloro-7-trifluoromethyl-pyrazolo[1,5-a]pyrimidine-2-carboxylic acid (2,3-dichloro-phenyl)-amide | 562 |
| 2-{[5-(4-Bromo-phenyl)-3-chloro-7-trifluoromethyl-pyrazolo[1,5-a]pyrimidine-2-carbonyl]-amino}-benzoic acid methyl ester | 552 |
| 5-(4-Bromo-phenyl)-3-chloro-7-trifluoromethyl-pyrazolo[1,5-a]pyrimidine-2-carboxylic acid (4-acetyl-phenyl)-amide | 536 |
| 5-(4-Bromo-phenyl)-3-chloro-7-trifluoromethyl-pyrazolo[1,5-a]pyrimidine-2-carboxylic acid (2-trifluoromethyl-phenyl)-amide | 562 |
| 5-(4-Bromo-phenyl)-3-chloro-7-trifluoromethyl-pyrazolo[1,5-a]pyrimidine-2-carboxylic acid (3-trifluoromethyl-phenyl)-amide | 562 |
| 5-(4-Bromo-phenyl)-3-chloro-7-trifluoromethyl-pyrazolo[1,5-a]pyrimidine-2-carboxylic acid (2,4-dimethoxy-phenyl)-amide | 554 |
| 5-(4-Bromo-phenyl)-3-chloro-7-trifluoromethyl-pyrazolo[1,5-a]pyrimidine-2-carboxylic acid naphthalen-1-ylamide | 544 |
| 5-(4-Bromo-phenyl)-3-chloro-7-trifluoromethyl-pyrazolo[1,5-a]pyrimidine-2-carboxylic acid (4-bromo-phenyl)-amide | 572 |
| 5-(4-Bromo-phenyl)-3-chloro-7-trifluoromethyl-pyrazolo[1,5-a]pyrimidine-2-carboxylic acid (2-methylsulfanyl-phenyl)-amide | 540 |
| 5-(4-Bromo-phenyl)-3-chloro-7-trifluoromethyl-pyrazolo[1,5-a]pyrimidine-2-carboxylic acid (2-chloro-5-trifluoromethyl-phenyl)-amide | 596 |
| 5-(4-Bromo-phenyl)-3-chloro-7-trifluoromethyl-pyrazolo[1,5-a]pyrimidine-2-carboxylic acid (thiophen-2-ylmethyl)-amide | 514 |
| 5-(4-Bromo-phenyl)-3-chloro-7-trifluoromethyl-pyrazolo[1,5-a]pyrimidine-2-carboxylic acid 4-chloro-benzylamide | 542 |
| 5-(4-Bromo-phenyl)-3-chloro-7-trifluoromethyl-pyrazolo[1,5-a]pyrimidine-2-carboxylic acid benzo[1,3]dioxol-4-ylamide | 538 |
| 5-(4-Bromo-phenyl)-3-chloro-7-trifluoromethyl-pyrazolo[1,5-a]pyrimidine-2-carboxylic acid (1-phenyl-ethyl)-amide | 522 |
| 5-(4-Bromo-phenyl)-3-chloro-7-trifluoromethyl-pyrazolo[1,5-a]pyrimidine-2-carboxylic acid (4-trifluoromethoxy-phenyl)-amide | 578 |
| 5-(4-Bromo-phenyl)-3-chloro-7-trifluoromethyl-pyrazolo[1,5-a]pyrimidine-2-carboxylic acid (4-chloro-2-methoxy-phenyl)-amide | 558 |

-continued

| name | MZ |
|---|---|
| 5-(4-Bromo-phenyl)-3-chloro-7-trifluoromethyl-pyrazolo[1,5-a]pyrimidine-2-carboxylic acid (2-bromo-4,6-difluoro-phenyl)-amide | 608 |
| 5-(4-Bromo-phenyl)-3-chloro-7-trifluoromethyl-pyrazolo[1,5-a]pyrimidine-2-carboxylic acid (1,5-dimethyl-3-oxo-2-phenyl-2,3-dihydro-1H-pyrazol-4-yl)-amide | 604 |
| 5-(4-Bromo-phenyl)-3-chloro-7-trifluoromethyl-pyrazolo[1,5-a]pyrimidine-2-carboxylic acid (2,4-difluoro-phenyl)-amide | 530 |
| 5-(4-Bromo-phenyl)-3-chloro-7-trifluoromethyl-pyrazolo[1,5-a]pyrimidine-2-carboxylic acid (3-cyano-4,5,6,7-tetrahydro-benzo[b]thiophen-2-yl)-amide | 579 |
| 5-(4-Bromo-phenyl)-3-chloro-7-trifluoromethyl-pyrazolo[1,5-a]pyrimidine-2-carboxylic acid (2-chloro-pyridin-3-yl)-amide | 529 |
| 5-(4-Bromo-phenyl)-3-chloro-7-trifluoromethyl-pyrazolo[1,5-a]pyrimidine-2-carboxylic acid (5-chloro-pyridin-2-yl)-amide | 529 |
| 5-(4-Bromo-phenyl)-3-chloro-7-trifluoromethyl-pyrazolo[1,5-a]pyrimidine-2-carboxylic acid phenethyl-amide | 522 |
| 5-(4-Bromo-phenyl)-3-chloro-7-trifluoromethyl-pyrazolo[1,5-a]pyrimidine-2-carboxylic acid (2,6-dichloro-phenyl)-amide | 562 |
| 5-(4-Bromo-phenyl)-3-chloro-7-trifluoromethyl-pyrazolo[1,5-a]pyrimidine-2-carboxylic acid (5-methyl-isoxazol-3-yl)-amide | 499 |
| 5-(4-Bromo-phenyl)-3-chloro-7-trifluoromethyl-pyrazolo[1,5-a]pyrimidine-2-carboxylic acid (3-methoxy-5-nitro-phenyl)-amide | 569 |
| 3-Bromo-5-(4-bromo-phenyl)-7-trifluoromethyl-pyrazolo[1,5-a]pyrimidine-2-carboxylic acid (furan-2-ylmethyl)-amide | 542 |
| 3-Bromo-5-(4-bromo-phenyl)-7-trifluoromethyl-pyrazolo[1,5-a]pyrimidine-2-carboxylic acid benzylamide | 552 |
| 3-Bromo-5-(4-bromo-phenyl)-7-trifluoromethyl-pyrazolo[1,5-a]pyrimidine-2-carboxylic acid (4-chloro-phenyl)-amide | 572 |
| 3-Bromo-5-(4-bromo-phenyl)-7-trifluoromethyl-pyrazolo[1,5-a]pyrimidine-2-carboxylic acid (2,4-dichloro-phenyl)-amide | 606 |
| 3-Bromo-5-(4-bromo-phenyl)-7-trifluoromethyl-pyrazolo[1,5-a]pyrimidine-2-carboxylic acid (2,3-dichloro-phenyl)-amide | 606 |
| 3-Bromo-5-(4-bromo-phenyl)-7-trifluoromethyl-pyrazolo[1,5-a]pyrimidine-2-carboxylic acid naphthalen-1-ylamide | 588 |
| 3-Bromo-5-(4-bromo-phenyl)-7-trifluoromethyl-pyrazolo[1,5-a]pyrimidine-2-carboxylic acid (4-bromo-phenyl)-amide | 616 |
| 5-(4-Nitro-phenyl)-7-trifluoromethyl-pyrazolo[1,5-a]pyrimidine-2-carboxylic acid (2,4-dichloro-phenyl)-amide | 495 |
| 5-(4-Nitro-phenyl)-7-trifluoromethyl-pyrazolo[1,5a]pyrimidine-2-carboxylic acid (2,3-dichloro-phenyl)-amide | 495 |
| 5-(4-Nitro-phenyl)-7-trifluoromethyl-pyrazolo[1,5-a]pyrimidine-2-carboxylic acid (4-acetyl-phenyl)-amide | 469 |
| 5-(4-Nitro-phenyl)-7-trifluoromethyl-pyrazolo[1,5-a]pyrimidine-2-carboxylic acid (5-methyl-isoxazol-3-yl)-amide | 432 |
| 5-(3,4-Dichloro-phenyl)-7-trifluoromethyl-pyrazolo[1,5-a]pyrimidine-2-carboxylic acid (furan-2-ylmethyl)-amide | 454 |
| 5-(3,4-Dichloro-phenyl)-7-trifluoromethyl-pyrazolo[1,5-a]pyrimidine-2-carboxylic acid (3-cyano-4,5,6,7-tetrahydro-benzo[b]thiophen-2-yl)-amide | 535 |
| 5-(3,4-Dichloro-phenyl)-7-trifluoromethyl-pyrazolo[1,5-a]pyrimidine-2-carboxylic acid (3-cyano-6-methyl-4,5,6,7-tetrahydro-benzo[b]thiophen-2-yl)-amide | 549 |
| 5-(3,4-Dichloro-phenyl)-7-trifluoromethyl-pyrazolo[1,5-a]pyrimidine-2-carboxylic acid (5-methyl-isoxazol-3-yl)-amide | 455 |
| 5-(3,4-Dimethoxy-phenyl)-7-trifluoromethyl-pyrazolo[1,5-a]pyrimidine-2-carboxylic acid (3,4-dichloro-phenyl)-amide | 510 |
| (5-Benzo[1,3]dioxol-5-yl-7-trifluoromethyl-pyrazolo[1,5-a]pyrimidin-2-yl)-(4-methyl-piperidin-1-yl)-methanone | 432 |
| 5-Benzo[1,3]dioxol-5-yl-7-trifluoromethyl-pyrazolo[1,5-a]pyrimidine-2-carboxylic acid (3-imidazol-1-yl-propyl)-amide | 458 |
| 5.(3,4-Dimethoxy-phenyl)-7-trifluoromethyl-pyrazolo[1,5-a]pyrimidine-2-carboxylic acid (3,5-dichloro-phenyl)-amide | 510 |
| 5-Benzo[1,3]dioxol-5-yl-7-trifluoromethyl-pyrazolo[1,5-a]pyrimidine-2-carboxylic acid (6-acetyl-benzo[1,3]dioxol-5-yl)-amide | 512 |
| {2-[(5-Benzo[1,3]dioxol-5-yl-7-trifluoromethyl-pyrazolo[1,5-a]pyrimidine-2-carbonyl)-amino]-thiazol-4-yl}-acetic acid ethyl ester | 519 |
| 5-Benzo[1,3]dioxol-5-yl-7-trifluoromethyl-pyrazolo[1,5-a]pyrimidine-2-carboxylic acid m-tolylamide | 440 |
| 5-Thiophen-2-yl-7-trifluoromethyl-pyrazolo[1,5-a]pyrimidine-2-carboxylic acid propylamide | 354 |
| 3-Bromo-5-(4-methoxy-phenyl)-7-trifluoromethyl-pyrazolo[1,5-a]pyrimidine-2-carboxylic acid (2,4-dichloro-phenyl)-amide | 558 |
| (4-Benzhydryl-piperazin-1-yl)-(3-chloro-5-phenyl-7-trifluoromethyl-pyrazolo[1,5-a]pyrimidin-2-yl)-methanone | 575 |
| 3-Chloro-5-phenyl-7-trifluoromethyl-pyrazolo[1,5-a]pyrimidine-2-carboxylic acid (3-nitro-5-phenoxy-phenyl)-amide | 553 |

-continued

| name | MZ |
|------|-----|
| 3-Chloro-5-phenyl-7-trifluoromethyl-pyrazolo[1,5-a]pyrimidine-2-carboxylic acid [3-(4-fluoro-phenoxy)-5-nitro-phenyl]-amide | 571 |
| 3-Chloro-5-phenyl-7-trifluoromethyl-pyrazolo[1 5-a]pyrimidine-2-carboxylic acid [3,5-bis-(4-fluoro-phenoxy)-phenyl]-amide | 636 |
| 5-Phenyl-7-trifluoromethyl-pyrazolo[1,5-a]pyrimidine-2-carboxylic acid (4-trifluoromethoxy-phenyl)-amide | 466 |
| 3-Bromo-5-phenyl-7-trifluoromethyl-pyrazolo[1,5-a]pyrimidine-2-carboxylic acid (4-chloro-2,5-dimethoxy-phenyl)-amide | 554 |
| 7-Methyl-5-phenyl-pyrazolo[1,5-a]pyrimidine-2-carboxylic acid naphthalen-1-ylamide | 378 |
| 7-Methyl-5-phenyl-pyrazolo[1,5-a]pyrimidine-2-carboxylic acid [3-(4-chloro-2-cyclohexyl-phenoxy)-5-nitro-phenyl]-amide | 581 |
| 5,7-Diphenyl-pyrazolo[1,5-a]pyrimidine-2-carboxylic acid sec-butylamide | 370 |
| 5,7-Diphenyl-pyrazolo[1,5-a]pyrimidine-2-carboxylic acid benzyl-methyl-amide | 418 |
| Azepan-1-yl-(5,7-diphenyl-pyrazolo[1,5-a]pyrimidin-2-yl)-methanone | 396 |
| 3-Chloro-5-thiophen-2-yl-7-trifluoromethyl-pyrazolo[1,5-a]pyrimidine-2-carboxylic acid (3-nitro-5-phenoxy-phenyl)-amide | 559 |
| 5-[(3-Chloro-5-thiophen-2-yl-7-trifluoromethyl-pyrazolo[1,5-a]pyrimidine-2-carbonyl)-amino]-3-methyl-thiophene-2,4-dicarboxylic acid diethyl ester | 586 |
| 3-Chloro-5-thiophen-2-yl-7-trifluoromethyl-pyrazolo[1,5-a]pyrimidine-2-carboxylic acid [3-(4-fluoro-phenoxy)-5-nitro-phenyl]-amide | 577 |
| 3-Chloro-5-thiophen-2-yl-7-trifluoromethyl-pyrazolo[1,5-a]pyrimidine-2-carboxylic acid (3-nitro-5-m-tolyloxy-phenyl)-amide | 573 |
| 3-Chloro-5-thiophen-2-yl-7-trifluoromethyl-pyrazolo[1,5-a]pyrimidine-2-carboxylic acid [3-(4-bromo-phenylsulfanyl)-5-nitro-phenyl]-amide | 653 |
| 3-Chloro-5-thiophen-2-yl-7-trifluoromethyl-pyrazolo[1,5-a]pyrimidine-2-carboxylic acid [3-(4-ethoxy-phenoxy)-5-nitro-phenyl]-amide | 603 |
| 5-Thiophen-2-yl-7-trifluoromethyl-pyrazolo[1,5-a]pyrimidine-2-carboxylic acid [4-bromo-2-(2-chloro-benzoyl)-phenyl]-amide | 604 |
| 5-(4-Methoxy-phenyl)-7-trifluoromethyl-pyrazolo[1,5-a]pyrimidine-2-carboxylic acid [4-bromo-2-(2-chloro-benzoyl)-phenyl]-amide | 628 |
| 5-Thiophen-2-yl-7-trifluoromethyl-pyrazolo[1,5-a]pyrimidine-2-carboxylic acid [4-chloro-2-(2-chloro-benzoyl)-phenyl]-amide | 560 |
| 5-(4-Methoxy-phenyl)-7-trifluoromethyl-pyrazolo[1,5-a]pyrimidine-2-carboxylic acid [4-chloro-2-(2-chloro-benzoyl)-phenyl]amide | 584 |
| 5-Thiophen-2-yl-7-trifluoromethyl-pyrazolo[1,5-a]pyrimidine-2-carboxylic acid [4-chloro-2-(3,4,5-trimethoxy-benzoyl)-phenyl]-amide | 616 |
| 5-Thiophen-2-yl-7-trifluoromethyl-pyrazolo[1,5-a]pyrimidine-2-carboxylic acid (6-amino-benzothiazol-2-yl)-(2,4-dichloro-benzoyl)-amide | 632 |
| 5-(4-Methoxy-phenyl)-7-trifluoromethyl-pyrazolo[1,5-a]pyrimidine-2-carboxylic acid (2-benzoyl-4-chloro-phenyl)-amide | 550 |
| 3-Chloro-5-thiophen-2-yl-7-trifluoromethyl-pyrazolo[1,5-a]pyrimidine-2-carboxylic acid [3-(4-acetylamino-phenoxy)-5-nitro-phenyl]-amide | 616 |
| 3-Chloro-5-thiophen-2-yl-7-trifluoromethyl-pyrazolo[1,5-a]pyrimidine-2-carboxylic acid [3-(3-chloro-phenoxy)-5-nitro-phenyl]-amide | 593 |
| 3-Chloro-5-thiophen-2-yl-7-trifluoromethyl-pyrazolo[1,5-a]pyrimidine-2-carboxylic acid [3-(4-chloro-2-cyclohexyl-phenoxy)-5-nitro-phenyl]-amide | 675 |
| 3-Chloro-5-thiophen-2-yl-7-trifluoromethyl-pyrazolo[1,5-a]pyrimidine-2-carboxylic acid [3-nitro-5-(3-trifluoromethyl-phenoxy)-phenyl]-amide | 627 |
| 3-Chloro-5-thiophen-2-yl-7-trifluoromethyl-pyrazolo[1,5-a]pyrimidine-2-carboxylic acid [3-(indan-5-yloxy)-5-nitro-phenyl]-amide | 599 |
| 3-Chloro-5-thiophen-2-yl-7-trifluoromethyl-pyrazolo[1,5-a]pyrimidine-2-carboxylic acid [3-phenoxy-5-(pyridin-3-yloxy)-phenyl]-amide | 607 |
| 2-[(3-Chloro-5-phenyl-7-trifluoromethyl-pyrazolo[1,5-a]pyrimidine-2-carbonyl)-amino]-5,6-dihydro-4H-cyclopenta[b]thiophene-3-carboxylic acid ethyl ester | 534 |
| 2-[(3-Chloro-5-phenyl-7-trifluoromethyl-pyrazolo[1,5-a]pyrimidine-2-carbonyl)-amino]-4,5,6,7-tetrahydro-benzo[b]thiophene-3-carboxylic acid isopropyl ester | 562 |
| 3-Chloro-5-phenyl-7-trifluoromethyl-pyrazolo[1,5-a]pyrimidine-2-carboxylic acid (3-carbamoyl-6-methyl-4,5,6,7-tetrahydro-benzo[b]thiophen-2-yl)-amide | 533 |
| 3-Chloro-5-phenyl-7-trifluoromethyl-pyrazolo[1,5-a]pyrimidine-2-carboxylic acid (6-tert-butyl-3-carbamoyl-4 5,6,7-tetrahydro-benzo[b]thiophen-2-yl)-amide | 575 |
| 2-[(3-Chloro-5-phenyl-7-trifluoromethyl-pyrazolo[1,5-a]pyrimidine-2-carbonyl)-amino]-4,5,6,7-tetrahydro-benzo[b]thiophene-3-carboxylic acid methyl ester | 534 |
| 2-[(3-Chloro-5-phenyl-7-trifluoromethyl-pyrazolo[1,5-a]pyrimidine-2-carbonyl)-amino]-6-methyl-4,5,6,7-tetrahydro-benzo[b]thiophene-3-carboxylic acid ethyl ester | 562 |

-continued

| name | MZ |
|---|---|
| 3-Chloro-5-phenyl-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide | 557 |
| 2-[(3-Chloro-5-phenyl-7-trifluoromethyl-pyrazolo[1,5-a]pyrimidine-2-carbonyl)-amino]-6-methyl-4,5,6,7-tetrahydro-benzo[b]thiophene-3-carboxylic acid methyl ester | 548 |
| 2-[(3-Chloro-5-thiophen-2-yl-7-trifluoromethyl-pyrazolo[1,5-a]pyrimidine-2-carbonyl)-amino]-5,6-dihydro-4H-cyclopenta[b]thiophene-3-carboxylic acid ethyl ester | 540 |
| 3-Chloro-5-thiophen-2-yl-7-trifluoromethyl-pyrazolo[1,5-a]pyrimidine-2-carboxylic acid (6-tert-butyl-3-carbamoyl-4,5,6,7-tetrahydro-benzo[b]thiophen-2-yl)-amide | 581 |
| 2-[(3-Chloro-5-thiophen-2-yl-7-trifluoromethyl-pyrazolo[1,5-a]pyrimidine-2-carbonyl)-amino]-4,5,6,7-tetrahydro-benzo[b]thiophene-3-carboxylic acid methyl ester | 540 |
| 3-Chloro-5-thiophen-2-yl-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide | 563 |
| 2-[(3-Chloro-5-thiophen-2-yl-7-trifluoromethyl-pyrazolo[1,5-a]pyrimidine-2-carbonyl)-amino]-6-methyl-4,5,6,7-tetrahydro-benzo[b]thiophene-3-carboxylic acid methyl ester | 554 |
| 5-(4-Bromo-phenyl)-3-chloro-7-trifluoromethyl-pyrazolo[1,5-a]pyrimidine-2-carboxylic acid (2-morpholin-4-yl-ethyl)-amide | 531 |
| [5-(4-Bromo-phenyl)-3-chloro-7-trifluoromethyl-pyrazolo[1,5-a]pyrimidin-2-yl]-(3,4-dihydro-2H-quinolin-1-yl)-methanone | 534 |
| 5-(4-Bromo-phenyl)-3-chloro-7-trifluoromethyl-pyrazolo[1,5-a]pyrimidine-2-carboxylic acid (3,4-dimethoxy-phenyl)-amide | 554 |
| (4-Benzyl-piperazin-1-yl)-[5-(4-bromo-phenyl)-3-chloro-7-trifluoromethyl-pyrazolo[1,5-a]pyrimidin-2-yl]-methanone | 577 |
| 5-(4-Bromo-phenyl)-3-chloro-7-trifluoromethyl-pyrazolo[1,5-a]pyrimidine-2-carboxylic acid benzyl-phenyl-amide | 584 |
| 2-{[5-(4-Bromo-phenyl)-3-chloro-7-trifluoromethyl-pyrazolo[1,5-a]pyrimidine-2-carbonyl]-amino}-4,5,6,7-tetrahydro-benzo[b]thiophene-3-carboxylic acid methyl ester | 612 |
| 5-(4-Bromo-phenyl)-3-chloro-7-trifluoromethyl-pyrazolo[1,5-a]pyrimidine-2-carboxylic acid (6-tert-butyl-3-cyano-4,5,6,7-tetrahydro-benzo[b]thiophen-2-yl)-amide | 635 |
| [5-(4-Bromo-phenyl)-3-chloro-7-trifluoromethyl-pyrazolo[1,5-a]pyrimidin-2-yl]-(3,4-dihydro-1H-isoquinolin-2-yl)-methanone | 534 |
| 5-(3,4-Dichloro-phenyl)-7-trifluoromethyl-pyrazolo[1,5-a]pyrimidine-2-carboxylic acid (3-cyano-5,6,7,8-tetrahydro-4H-cyclohepta[b]thiophen-2-yl)-amide | 549 |
| (4-Benzhydryl-piperazin-1-yl)-(3-chloro-5-thiophen-2-yl-7-trifluoromethyl-pyrazolo[1,5-a]pyrimidin-2-yl)-methanone | 581 |
| 5-{[5-(4-Bromo-phenyl)-3-chloro-7-trifluoromethyl-pyrazolo[1,5-a]pyrimidine-2-carbonyl]-amino}-3-methyl-thiophene-2,4-dicarboxylic acid diethyl ester | 658 |
| 5-{[5-(3,4-Dichloro-phenyl)-7-trifluoromethyl-pyrazolo[1,5-a]pyrimidine-2-carbonyl]-amino}-3-methyl-thiophene-2,4-dicarboxylic acid diethyl ester | 614 |
| 5-{[5-(3,4-Dichloro-phenyl)-7-trifluoromethyl-pyrazolo[1,5-a]pyrimidine-2-carbonyl]-amino}-3-methyl-thiophene-2,4-dicarboxylic acid dimethyl ester | 586 |
| 5-(4-Bromo-phenyl)-7-trifluoromethyl-pyrazolo[1,5-a]pyrimidine-2-carboxylic acid benzylamide | 474 |
| 5-(4-Bromo-phenyl)-7-trifluoromethyl-pyrazolo[1,5-a]pyrimidine-2-carboxylic acid (thiophen-2-ylmethyl)-amide | 480 |
| 5-(3,4-Dichloro-phenyl)-7-trifluoromethyl-pyrazolo[1,5-a]pyrimidine-2-carboxylic acid (1-phenyl-ethyl)-amide | 478 |
| 5-(3,4-Dichloro-phenyl)-7-trifluoromethyl-pyrazolo[1,5-a]pyrimidine-2-carboxylic acid (pyridin-3-ylmethyl)-amide | 465 |
| 3-Chloro-5-(4-fluoro-phenyl)-7-trifluoromethyl-pyrazolo[1,5-a]pyrimidine-2-carboxylic acid (1-phenyl-ethyl)-amide | 462 |
| 3-Chloro-5-(4-fluoro-phenyl)-7-trifluoromethyl-pyrazolo[1,5-a]pyrimidine-2-carboxylic acid (pyridin-3-ylmethyl)-amide | 449 |
| 3-Chloro-5-(4-chloro-phenyl)-7-trifluoromethyl-pyrazolo[1,5-a]pyrimidine-2-carboxylic acid 4-fluoro-benzylamide | 482 |
| 3-Chloro-5-(4-chloro-phenyl)-7-trifluoromethyl-pyrazolo[1,5-a]pyrimidine-2-carboxylic acid 4-chloro-benzylamide | 498 |
| 3-Chloro-5-p-tolyl-7-trifluoromethyl-pyrazolo[1,5-a]pyrimidine-2-carboxylic acid (1-phenyl-ethyl)-amide | 458 |
| 7-Trifluoromethyl-5,6-dihydro-7a,8,11-triaza-cyclopenta[b]phenanthrene-9-carboxylic acid 4-chloro-benzylamide | 456 |
| 3-Bromo-5-phenyl-7-trifluoromethyl-pyrazolo[1,5-a]pyrimidine-2-carboxylic acid (1-phenyl-ethyl)-amide | 488 |
| 5-(4-Methoxy-phenyl)-7-trifluoromethyl-pyrazolo[1,5-a]pyrimidine-2-carboxylic acid benzylamide | 426 |

-continued

| name | MZ |
|---|---|
| 5-(4-Nitro-phenyl)-7-trifluoromethyl-pyrazolo[1,5-a]pyrimidine-2-carboxylic acid 4-methoxy-benzylamide | 471 |
| 3-Bromo-5-phenyl-7-trifluoromethyl-pyrazolo[1,5-a]pyrimidine-2-carboxylic acid benzyl-methyl-amide | 488 |
| 3-Chloro-5-(4-fluoro-phenyl)-7-trifluoromethyl-pyrazolo[1,5-a]pyrimidine-2-carboxylic acid 4-chloro-benzylamide | 482 |
| 5-Phenyl-7-trifluoromethyl-pyrazolo[1,5-a]pyrimidine-2-carboxylic acid benzyl-methyl-amide | 410 |
| 7-Methyl-5-phenyl-pyrazolo[1,5-a]pyrimidine-2-carboxylic acid benzyl-methyl-amide | 356 |
| 3-Bromo-5-phenyl-7-trifluoromethyl-pyrazolo[1,5-a]pyrimidine-2-carboxylic acid 4-fluoro-benzylamide | 492 |
| 5-(4-Nitro-phenyl)-7-trifluoromethyl-pyrazolo[1,5-a]pyrimidine-2-carboxylic acid 4-chloro-benzylamide | 475 |
| 5,7-Diphenyl-pyrazolo[1,5-a]pyrimidine-2-carboxylic acid (1-phenyl-ethyl)-amide | 418 |
| 5-Phenyl-7-trifluoromethyl-pyrazolo[1,5-a]pyrimidine-2-carboxylic acid (1-phenyl-ethyl)-amide | 410 |
| 5-Phenyl-7-trifluoromethyl-pyrazolo[1,5-a]pyrimidine-2-carboxylic acid 4-chloro-benzylamide | 430 |
| 3-Chloro-5-(4-chloro-phenyl)-7-trifluoromethyl-pyrazolo[1,5-a]pyrimidine-2-carboxylic acid (1-phenyl-ethyl)-amide | 478 |
| 3-Chloro-5-p-tolyl-7-trifluoromethyl-pyrazolo[1,5-a]pyrimidine-2-carboxylic acid benzyl-phenyl-amide | 520 |
| 3-Bromo-5-phenyl-7-trifluoromethyl-pyrazolo[1,5-a]pyrimidine-2-carboxylic acid (pyridin-3-ylmethyl)-amide | 475 |
| 5-p-Tolyl-7-trifluoromethyl-pyrazolo[1,5-a]pyrimidine-2-carboxylic acid dibenzylamide | 500 |
| 5-Phenyl-7-trifluoromethyl-pyrazolo[1,5-a]pyrimidine-2-carboxylic acid dibenzylamide | 486 |
| 3-Bromo-5-phenyl-7-trifluoromethyl-pyrazolo[1,5-a]pyrimidine-2-carboxylic acid dibenzylamide | 564 |
| 5-(4-Bromo-phenyl)-7-trifluoromethyl-pyrazolo[1,5-a]pyrimidine-2-carboxylic acid benzyl-phenyl-amide | 550 |
| 3-Chloro-5-phenyl-7-trifluoromethyl-pyrazolo[1,5-a]pyrimidine-2-carboxylic acid dibenzylamide | 520 |
| 7-Methyl-5-phenyl-pyrazolo[1,5-a]pyrimidine-2-carboxylic acid 4-chloro-benzylamide | 376 |
| 3-Chloro-5-(4-methoxy-phenyl)-7-trifluoromethyl-pyrazolo[1,5-a]pyrimidine-2-carboxylic acid benzylamide | 460 |
| 3-Chloro-5-(4-methoxy-phenyl)-7-trifluoromethyl-pyrazolo[1,5-a]pyrimidine-2-carboxylic acid benzylamide | 444 |
| 3-Bromo-5-phenyl-7-trifluoromethyl-pyrazolo[1,5-a]pyrimidine-2-carboxylic acid 4-methoxy-benzylamide | 504 |
| 3-Chloro-5-(4-chloro-phenyl)-7-trifluoromethyl-pyrazolo[1,5-a]pyrimidine-2-carboxylic acid benzyl-methyl-amide | 478 |
| 3-Chloro-5-(3,4-dimethoxy-phenyl)-7-trifluoromethyl-pyrazolo[1,5-a]pyrimidine-2-carboxylic acid benzylamide | 490 |
| (3,4-Dihydro-1H-isoquinolin-2-yl)-[5-(4-methoxy-phenyl)-7-trifluoromethyl-pyrazolo[1,5-a]pyrimidin-2-yl]-methanone | 452 |
| 3-Chloro-5-p-tolyl-7-trifluoromethyl-pyrazolo[1 5-a]pyrimidine-2-carboxylic acid (pyridin-3-ylmethyl)-amide | 445 |
| (3,4-Dihydro-1H-isoquinolin-2-yl)-(5-phenyl-7-trifluoromethyl-pyrazolo[1,5-a]pyrimidin-2-yl)-methanone | 422 |
| 3-Chloro-5-(4-methoxy-phenyl)-7-trifluoromethyl-pyrazolo[1,5-a]pyrimidine-2-carboxylic acid benzyl-methyl-amide | 474 |
| 5-(3,4-Dimethoxy-phenyl)-7-trifluoromethyl-pyrazolo[1,5-a]pyrimidine-2-carboxylic acid 4-methoxy-benzylamide | 486 |
| 5-(4-Methoxy-phenyl)-7-trifluoromethyl-pyrazolo[1,5-a]pyrimidine-2-carboxylic acid (pyridin-3-ylmethyl)-amide | 427 |
| 3-Chloro-5-(4-methoxy-phenyl)-7-trifluoromethyl-pyrazolo[1,5-a]pyrimidine-2-carboxylic acid 4-methoxy-benzylamide | 490 |
| 3-Chloro-5-phenyl-7-trifluoromethyl-pyrazolo[1,5-a]pyrimidine-2-carboxylic acid 4-fluoro-benzylamide | 448 |
| (3-Chloro-5-phenyl-7-trifluoromethyl-pyrazolo[1,5-a]pyrimidin-2-yl)-(3,4-dihydro-1H-isoquinolin-2-yl)-methanone | 456 |
| 3-Chloro-5-phenyl-7-trifluoromethyl-pyrazolo[1,5-a]pyrimidine-2-carboxylic acid 4-methoxy-benzylamide | 460 |
| 5-(4-Chloro-phenyl)-7-trifluoromethyl-pyrazolo[1,5-a]pyrimidine-2-carboxylic acid 4-fluoro-benzylamide | 448 |
| 5-(4-Chloro-phenyl)-7-trifluoromethyl-pyrazolo[1,5-a]pyrimidine-2-carboxylic acid benzylamide | 430 |
| [5-(4-Bromo-phenyl)-7-trifluoromethyl-pyrazolo[1,5-a]pyrimidin-2-yl]-(3,4-dihydro-1H-isoquinolin-2-yl)-methanone | 500 |
| 3-Chloro-5-(4-chloro-phenyl)-7-trifluoromethyl-pyrazolo[1,5-a]pyrimidine-2-carboxylic acid benzyl-phenyl-amide | 540 |

-continued

| name | MZ |
|---|---|
| (3-Bromo-5-phenyl-7-trifluoromethyl-pyrazolo[1,5-a]pyrimidin-2-yl)-(3,4-dihydro-1H-isoquinolin-2-yl)-methanone | 500 |
| 5-(4-Nitro-phenyl)-7-trifluoromethyl-pyrazolo[1,5-a]pyrimidine-2-carboxylic acid benzylamide | 441 |
| 5-(4-Bromo-phenyl)-3-chloro-7-trifluoromethyl-pyrazolo[1,5-a]pyrimidine-2-carboxylic acid 4-methoxy-benzylamide | 538 |
| 5-(4-Bromo-phenyl)-3-chloro-7-trifluoromethyl-pyrazolo[1,5-a]pyrimidine-2-carboxylic acid 4-methoxy-benzylamide | 431 |
| 5-(4-Bromo-phenyl)-7-trifluoromethyl-pyrazolo[1,5-a]pyrimidine-2-carboxylic acid 4-methoxy-benzylamide | 504 |
| 3-Chloro-5-phenyl-7-trifluoromethyl-pyrazolo[1,5-a]pyrimidine-2-carboxylic acid (1-phenyl-ethyl)-amide | 444 |
| 5-(4-Bromo-phenyl)-7-trifluoromethyl-pyrazolo[1,5-a]pyrimidine-2-carboxylic acid (1-phenyl-ethyl)-amide | 488 |
| 3-Chloro-5-(4-fluoro-phenyl)-7-trifluoromethyl-pyrazolo[1,5-a]pyrimidine-2-carboxylic acid benzyl-methyl-amide | 462 |
| 5-(4-Nitro-phenyl)-7-trifluoromethyl-pyrazolo[1,5-a]pyrimidine-2-carboxylic acid (1-phenyl-ethyl)-amide | 455 |
| 3-Chloro-5-p-tolyl-7-trifluoromethyl-pyrazolo[1,5-a]pyrimidine-2-carboxylic acid benzyl-methyl-amide | 458 |
| 3-Chloro-5-(4-methoxy-phenyl)-7-trifluoromethyl-pyrazolo[1,5-a]pyrimidine-2-carboxylic acid (1-phenyl-ethyl)-amide | 474 |
| 5-p-Tolyl-7-trifluoromethyl-pyrazolo[1,5-a]pyrimidine-2-carboxylic acid benzyl-methyl-amide | 424 |
| 3-Chloro-5-p-tolyl-7-trifluoromethyl-pyrazolo[1,5-a]pyrimidine-2-carboxylic acid 4-methoxy-benzylamide | 474 |
| 3-Chloro-5-(3,4-dimethoxy-phenyl)-7-trifluoromethyl-pyrazolo[1,5-a]pyrimidine-2-carboxylic acid (pyridin-3-ylmethyl)-amide | 491 |
| 3-Bromo-5-phenyl-7-trifluoromethyl-pyrazolo[1,5-a]pyrimidine-2-carboxylic acid benzylamide | 474 |
| 7-Methyl-5-phenyl-pyrazolo[1,5-a]pyrimidine-2-carboxylic acid benzylamide | 342 |
| 5-(4-Bromo-phenyl)-7-trifluoromethyl-pyrazolo[1,5-a]pyrimidine-2-carboxylic acid 4-chloro-benzylamide | 508 |
| 5-(3,4-Dichloro-phenyl)-7-trifluoromethyl-pyrazolo[1,5-a]pyrimidine-2-carboxylic acid benzylamide | 464 |
| 5-(3,4-Dichloro-phenyl)-7-trifluoromethyl-pyrazolo[1,5-a]pyrimidine-2-carboxylic acid phenethyl-amide | 478 |
| 7-Trifluoromethyl-5,6-dihydro-7a,8,11-triaza-cyclopenta[b]phenanthrene-9-carboxylic acid dibenzylamide | 512 |
| 10-Chloro-7-trifluoromethyl-5,6-dihydro-7a,8,11-triaza-cyclopenta[b]phenanthrene-9-carboxylic acid benzyl-methyl-amide | 470 |
| (6-Hydroxy-7-methoxy-1-methyl-3,4-dihydro-1H-isoquinolin-2-yl)-[5-(4-methoxy-phenyl)-7-trifluoromethyl-pyrazolo[1,5-a]pyrimidin-2-yl]-methanone | 512 |
| 5-(4-Chloro-phenyl)-7-trifluoromethyl-pyrazolo[1,5-a]pyrimidine-2-carboxylic acid benzyl-(2-hydroxy-ethyl)-amide | 474 |
| 5-(3,4-Dimethoxy-phenyl)-7-trifluoromethyl-pyrazolo[1,5-a]pyrimidine-2-carboxylic acid 2-chloro-benzylamide | 490 |
| 5-Benzo[1,3]dioxol-5-yl-7-trifluoromethyl-pyrazolo[1,5-a]pyrimidine-2-carboxylic acid 2-chloro-benzylamide | 474 |
| (3,4-Dihydro-1H-isoquinolin-2-yl)-[5-(3,4-dimethoxy-phenyl)-7-trifluoromethyl-pyrazolo[1,5-a]pyrimidin-2-yl]-methanone | 482 |
| 5-(3,4-Dimethoxy-phenyl)-7-trifluoromethyl-pyrazolo[1,5-a]pyrimidine-2-carboxylic acid benzylamide | 456 |
| (5-Benzo[1,3]dioxol-5-yl-7-trifluoromethyl-pyrazolo[1,5-a]pyrimidin-2-yl)-(3,4-dihydro-1H-isoquinolin-2-yl)-methanone | 466 |
| 5-Benzo[1,3]dioxol-5-yl-7-trifluoromethyl-pyrazolo[1,5-a]pyrimidine-2-carboxylic acid benzylamide | 440 |
| 5-Benzo[1,3]dioxol-5-yl-7-trifluoromethyl-pyrazolo[1,5-a]pyrimidine-2-carboxylic acid (pyridin-3-ylmethyl)-amide | 441 |
| 5-(3,4-Dimethoxy-phenyl)-7-trifluoromethyl-pyrazolo[1,5-a]pyrimidine-2-carboxylic acid (benzo[1,3]dioxol-5-ylmethyl)-amide | 500 |
| 5-Benzo[1,3]dioxol-5-yl-7-trifluoromethyl-pyrazolo[1,5-a]pyrimidine-2-carboxylic acid 3-chloro-benzylamide | 474 |
| (5-Benzo[1,3]dioxol-5-yl-7-trifluoromethyl-pyrazolo[1,5-a]pyrimidin-2-yl)-(6,7-dimethoxy-1-methyl-3,4-dihydro-1H-isoquinolin-2-yl)-methanone | 540 |
| 5-Benzo[1,3]dioxol-5-yl-7-trifluoromethyl-pyrazolo[1,5-a]pyrimidine-2-carboxylic acid (benzo[1,3]dioxol-5-ylmethyl)-amide | 484 |
| 7-Amino-5-(3,4-dichloro-phenyl)-pyrazolo[1,5-a]pyrimidine-2-carboxylic acid benzylamide | 411 |
| 5,7-Bis-trifluoromethyl-pyrazolo[1,5-a]pyrimidine-2-carboxylic acid benzylamide | 388 |
| 5-(3,4-Dichloro-phenyl)-7-trifluoromethyl-pyrazolo[1,5-a]pyrimidine-2-carboxylic acid bis-(2-methoxy-ethyl)-amide | 490 |

-continued

| name | MZ |
|---|---|
| 5-(3,4-Dichloro-phenyl)-7-trifluoromethyl-pyrazolo[1,5-a]pyrimidine-2-carboxylic acid (pyridin-2-ylmethyl)-amide | 465 |
| 5-Pyridin-3-yl-7-trifluoromethyl-pyrazolo[1,5-a]pyrimidine-2-carboxylic acid benzylamide | 397 |
| 5-Pyridin-4-yl-7-trifluoromethyl-pyrazolo[1,5-a]pyrimidine-2-carboxylic acid benzylamide | 397 |
| 5-Pyridin-2-yl-7-trifluoromethyl-pyrazolo[1,5-a]pyrimidine-2-carboxylic acid benzylamide | 397 |
| 5-(3,4-Dihydroxy-phenyl)-7-trifluoromethyl-pyrazolo[1,5-a]pyrimidine-2-carboxylic acid benzylamide | 428 |
| 5-Phenyl-7-trifluoromethyl-pyrazolo[1,5-a]pyrimidine-2-carboxylic acid (3-hydroxy-5-nitro-phenyl)-amide | 443 |
| 3-Chloro-5-phenyl-7-trifluoromethyl-pyrazolo[1,5-a]pyrimidine-2-carboxylic acid (5-chloro-2-hydroxy-phenyl)-amide | 466 |
| 3-Chloro-5-phenyl-7-trifluoromethyl-pyrazolo[1,5-a]pyrimidine-2-carboxylic acid (2,3-dichloro-phenyl)-amide | 484 |
| 3-Chloro-5-phenyl-7-trifluoromethyl-pyrazolo[1,5-a]pyrimidine-2-carboxylic acid (3-chloro-4-fluoro-phenyl)-amide | 468 |
| 3-Chloro-5-phenyl-7-trifluoromethyl-pyrazolo[1,5-a]pyrimidine-2-carboxylic acid (2-chloro-pyridin-3-yl)-amide | 451 |
| 3-Bromo-5-phenyl-7-trifluoromethyl-pyrazolo[1,5-a]pyrimidine-2-carboxylic acid (3-chloro-2-methyl-phenyl)-amide | 508 |
| 3-Bromo-5-phenyl-7-trifluoromethyl-pyrazolo[1,5-a]pyrimidine-2-carboxylic acid (3-hydroxy-5-nitro-phenyl)-amide | 521 |
| 3-Bromo-5-phenyl-7-trifluoromethyl-pyrazolo[1,5-a]pyrimidine-2-carboxylic acid benzo[1,3]dioxol-5-ylamide | 504 |
| 5-Thiophen-2-yl-7-trifluoromethyl-pyrazolo[1,5-a]pyrimidine-2-carboxylic acid (2,5-dichloro-phenyl)-amide | 456 |
| 3-Bromo-5-thiophen-2-yl-7-trifluoromethyl-pyrazolo[1,5-a]pyrimidine-2-carboxylic acid (4-acetyl-phenyl)-amide | 508 |
| 5-Furan-2-yl-7-trifluoromethyl-pyrazolo[1,5-a]pyrimidine-2-carboxylic acid (3-chloro-4-fluoro-phenyl)-amide | 424 |
| 3-Chloro-5-thiophen-2-yl-7-trifluoromethyl-pyrazolo[1,5-a]pyrimidine-2-carboxylic acid (2,5-dichloro-phenyl)-amide | 490 |
| 3-Chloro-5-thiophen-2-yl-7-trifluoromethyl-pyrazolo[1,5-a]pyrimidine-2-carboxylic acid (3-trifluoromethyl-phenyl)-amide | 490 |
| 3-Bromo-5-(4-bromo-thiophen-2-yl)-7-trifluoromethyl-pyrazolo[1,5-a]pyrimidine-2-carboxylic acid (3,4-dimethoxy-phenyl)-amide | 604 |
| 5-(4-Fluoro-phenyl)-7-trifluoromethyl-pyrazolo[1,5-a]pyrimidine-2-carboxylic acid (5-chloro-2-hydroxy-phenyl)-amide | 450 |
| 5-(3,4-Dimethoxy-phenyl)-7-trifluoromethyl-pyrazolo[1,5-a]pyrimidine-2-carboxylic acid (2,4-dichloro-phenyl)-amide | 510 |
| 5-(4-Nitro-phenyl)-7-trifluoromethyl-pyrazolo[1,5-a]pyrimidine-2-carboxylic acid (4-chloro-phenyl)-amide | 461 |
| 5-Thiophen-2-yl-7-trifluoromethyl-pyrazolo[1,5-a]pyrimidine-2-carboxylic acid (4-chloro-2-methoxy-phenyl)-amide | 452 |
| 5-(3,4-Dichloro-phenyl)-7-trifluoromethyl-pyrazolo[1,5-a]pyrimidine-2-carboxylic acid benzo[1,3]dioxol-5-ylamide | 494 |
| 3-Chloro-5-furan-2-yl-7-trifluoromethyl-pyrazolo[1,5-a]pyrimidine-2-carboxylic acid (4-chloro-phenyl)-amide | 440 |
| 3-Chloro-5-furan-2-yl-7-trifluoromethyl-pyrazolo[1,5-a]pyrimidine-2-carboxylic acid (3-chloro-phenyl)-amide | 440 |
| 3-Chloro-5-furan-2-yl-7-trifluoromethyl-pyrazolo[1,5-a]pyrimidine-2-carboxylic acid (2-chloro-pyridin-3-yl)-amide | 441 |
| 3-Chloro-5-furan-2-yl-7-trifluoromethyl-pyrazolo[1,5-a]pyrimidine-2-carboxylic acid 4-chloro-benzylamide | 454 |
| 3-Chloro-5-furan-2-yl-7-trifluoromethyl-pyrazolo[1,5-a]pyrimidine-2-carboxylic acid benzo[1,3]dioxol-5-ylamide | 450 |
| 3-Chloro-5-furan-2-yl-7-trifluoromethyl-pyrazolo[1,5-a]pyrimidine-2-carboxylic acid (4-trifluoromethoxy-phenyl)-amide | 490 |
| 3-Chloro-5-furan-2-yl-7-trifluoromethyl-pyrazolo[1,5-a]pyrimidine-2-carboxylic acid (5-methyl-isoxazol-3-yl)-amide | 411 |
| 3-Chloro-5-furan-2-yl-7-trifluoromethyl-pyrazolo[1,5-a]pyrimidine-2-carboxylic acid (3-hydroxy-phenyl)-amide | 422 |
| 3-Chloro-5-(4-methoxy-phenyl)-7-trifluoromethyl-pyrazolo[1,5-a]pyrimidine-2-carboxylic acid (3-chloro-phenyl)-amide | 480 |
| 3-Chloro-5-(4-methoxy-phenyl)-7-trifluoromethyl-pyrazolo[1,5-a]pyrimidine-2-carboxylic acid (2,3-dichloro-phenyl)-amide | 514 |
| 3-Chloro-5-(4-methoxy-phenyl)-7-trifluoromethyl-pyrazolo[1,5-a]pyrimidine-2-carboxylic acid (3-chloro-4-fluoro-phenyl)-amide | 498 |
| 3-Chloro-5-(4-fluoro-phenyl)-7-trifluoromethyl-pyrazolo[1,5-a]pyrimidine-2-carboxylic acid (2-methylsulfanyl-phenyl)-amide | 480 |
| 3-Chloro-5-(4-fluoro-phenyl)-7-trifluoromethyl-pyrazolo[1,5-a]pyrimidine-2-carboxylic acid benzo[1,3]dioxol-5-ylamide | 478 |
| 3-Chloro-5-(4-fluoro-phenyl)-7-trifluoromethyl-pyrazolo[1,5-a]pyrimidine-2-carboxylic acid pyridin-3-ylamide | 435 |

-continued

| name | MZ |
|---|---|
| 3-Chloro-5-(4-chloro-phenyl)-7-trifluoromethyl-pyrazolo[1,5-a]pyrimidine-2-carboxylic acid benzo[1,3]dioxol-5-ylamide | 494 |
| 3-Chloro-5-(4-chloro-phenyl)-7-trifluoromethyl-pyrazolo[1,5-a]pyrimidine-2-carboxylic acid (2-chloro-4-nitro-phenyl)-amide | 529 |
| 3-Chloro-5-p-tolyl-7-trifluoromethyl-pyrazolo[1,5-a]pyrimidine-2-carboxylic acid (2,5-dichloro-phenyl)-amide | 498 |
| 3-Chloro-5-p-tolyl-7-trifluoromethyl-pyrazolo[1,5-a]pyrimidine-2-carboxylic acid (2-chloro-4-nitro-phenyl)-amide | 509 |
| 3-Chloro-5-(3,4-dimethoxy-phenyl)-7-trifluoromethyl-pyrazolo[1,5-a]pyrimidine-2-carboxylic acid (2-bromo-4,6-difluoro-phenyl)-amide | 590 |
| 3-Chloro-5-(3,4-dimethoxy-phenyl)-7-trifluoromethyl-pyrazolo[1,5-a]pyrimidine-2-carboxylic acid (2,4-difluoro-phenyl)-amide | 512 |
| 5-(4-Chloro-phenyl)-7-trifluoromethyl-pyrazolo[1,5-a]pyrimidine-2-carboxylic acid (4-cyano-phenyl)-amide | 441 |
| 5-(4-Chloro-phenyl)-7-trifluoromethyl-pyrazolo[1,5-a]pyrimidine-2-carboxylic acid (2-chloro-pyridin-3-yl)-amide | 451 |
| 5-(4-Chloro-phenyl)-7-trifluoromethyl-pyrazolo[1,5-a]pyrimidine-2-carboxylic acid (2-methylsulfanyl-phenyl)-amide | 462 |
| 5-(4-Chloro-phenyl)-7-trifluoromethyl-pyrazolo[1,5-a]pyrimidine-2-carboxylic acid (2-bromo-4,6-difluoro-phenyl)-amide | 530 |
| 5-(4-Chloro-phenyl)-7-trifluoromethyl-pyrazolo[1,5-a]pyrimidine-2-carboxylic acid (2-chloro-4-nitro-phenyl)-amide | 495 |
| 5-Benzo[1,3]dioxol-5-yl-7-trifluoromethyl-pyrazolo[1,5-a]pyrimidine-2-carboxylic acid (2-chloro-pyridin-3-yl)-amide | 461 |
| 3-Bromo-5-thiophen-2-yl-7-trifluoromethyl-pyrazolo[1,5-a]pyrimidine-2-carboxylic acid (thiophen-2-ylmethyl)-amide | 486 |
| 3-Chloro-5-furan-2-yl-7-trifluoromethyl-pyrazolo[1,5-a]pyrimidine-2-carboxylic acid (2,4-difluoro-phenyl)-amide | 442 |
| 3-Chloro-5-(4-chloro-phenyl)-7-trifluoromethyl-pyrazolo[1,5-a]pyrimidine-2-carboxylic acid (2,6-dichloro-phenyl)-amide | 518 |
| 5-{[3-Chloro-5-(3,4-dimethoxy-phenyl)-7-trifluoromethyl-pyrazolo[1,5-a]pyrimidine-2-carbonyl]-amino}-3-methyl-thiophene-2,4-dicarboxylic acid diethyl ester | 640 |
| 5-(4-Chloro-phenyl)-7-trifluoromethyl-pyrazolo[1,5-a]pyrimidine-2-carboxylic acid (4-acetyl-phenyl)-amide | 458 |
| 3-Chloro-5-furan-2-yl-7-trifluoromethyl-pyrazolo[1,5-a]pyrimidine-2-carboxylic acid (4-acetyl-phenyl)-amide | 448 |
| 3-Chloro-5-(4-methoxy-phenyl)-7-trifluoromethyl-pyrazolo[1,5-a]pyrimidine-2-carboxylic acid (2,4-difluoro-phenyl)-amide | 482 |
| 5-(4-Chloro-phenyl)-7-trifluoromethyl-pyrazolo[1,5-a]pyrimidine-2-carboxylic acid (3-hydroxy-phenyl)-amide | 432 |
| 5-(4-Chloro-phenyl)-7-trifluoromethyl-pyrazolo[1,5-a]pyrimidine-2-carboxylic acid (2,4-difluoro-phenyl)-amide | 452 |
| 3-Chloro-5-(4-fluoro-phenyl)-7-trifluoromethyl-pyrazolo[1,5-a]pyrimidine-2-carboxylic acid (furan-2-ylmethyl)-amide | 438 |
| 5-Benzo[1,3]dioxol-5-yl-7-trifluoromethyl-pyrazolo[1,5-a]pyrimidine-2-carboxylic acid (3-chloro-phenyl)-amide | 460 |
| 5,7-Diphenyl-pyrazolo[1,5-a]pyrimidine-2-carboxylic acid (thiophen-2-ylmethyl)-amide | 410 |
| 5,7-Diphenyl-pyrazolo[1,5-a]pyrimidine-2-carboxylic acid phenethyl-amide | 418 |
| 3-Chloro-5-(3,4-dimethoxy-phenyl)-7-trifluoromethyl-pyrazolo[1,5-a]pyrimidine-2-carboxylic acid tert-butylamide | 456 |
| 5-(3,4-Dimethoxy-phenyl)-7-trifluoromethyl-pyrazolo[1,5-a]pyrimidine-2-carboxylic acid tert-butylamide | 422 |
| 5-Thiophen-2-yl-7-trifluoromethyl-pyrazolo[1,5-a]pyrimidine-2-carboxylic acid benzylamide | 402 |
| 5-Phenyl-7-trifluoromethyl-pyrazolo[1,5-a]pyrimidine-2-carboxylic acid (3,4-dimethyl-phenyl)-amide | 410 |
| 3-Bromo-5-phenyl-7-trifluoromethyl-pyrazolo[1,5-a]pyrimidine-2-carboxylic acid (4-chloro-phenyl)-amide | 494 |
| (2-Methyl-piperidin-1-yl)-(5-phenyl-7-trifluoromethyl-pyrazolo[1,5-a]pyrimidin-2-yl)-methanone | 388 |
| (2-Methyl-piperidin-1-yl)-(5-phenyl-7-trifluoromethyl-pyrazolo[1,5-a]pyrimidin-2-yl)-methanone | 408 |
| 5-Thiophen-2-yl-7-trifluoromethyl-pyrazolo[1,5-a]pyrimidine-2-carboxylic acid cyclohexyl-methyl-amide | 408 |
| 3-Bromo-5-thiophen-2-yl-7-trifluoromethyl-pyrazolo[1,5-a]pyrimidine-2-carboxylic acid propylamide | 432 |
| [3-Bromo-5-(4-bromo-thiophen-2-yl)-7-trifluoromethyl-pyrazolo[1,5-a]pyrimidin-2-yl]-morpholin-4-yl-methanone | 538 |
| 3-Bromo-5-phenyl-7-trifluoromethyl-pyrazolo[1,5-a]pyrimidine-2-carboxylic acid butylamide | 440 |
| 5-(4-Methoxy-phenyl)-7-trifluoromethyl-pyrazolo[1,5-a]pyrimidine-2-carboxylic acid (2,4-dichloro-phenyl)-amide | 480 |
| 3-Chloro-5-phenyl-7-trifluoromethyl-pyrazolo[1,5-a]pyrimidine-2-carboxylic acid (2-hydroxy-5-methyl-phenyl)-amide | 446 |

-continued

| name | MZ |
|---|---|
| 3-Chloro-5-phenyl-7-trifluoromethyl-pyrazolo[1,5-a]pyrimidine-2-carboxylic acid (2,4-dimethoxy-phenyl)-amide | 476 |
| 3-Bromo-5-thiophen-2-yl-7-trifluoromethyl-pyrazolo[1,5-a]pyrimidine-2-carboxylic acid (2-ethyl-phenyl)-amide | 494 |
| (3-Bromo-5-thiophen-2-yl-7-trifluoromethyl-pyrazolo[1,5-a]pyrimidin-2-yl)-(2-ethyl-piperidin-1-yl)-methanone | 486 |
| 3-Bromo-5-thiophen-2-yl-7-trifluoromethyl-pyrazolo[1,5-a]pyrimidine-2-carboxylic acid (3,4-dimethoxy-phenyl)-amide | 526 |
| 3-Bromo-5-thiophen-2-yl-7-trifluoromethyl-pyrazolo[1,5-a]pyrimidine-2-carboxylic acid phenethyl-amide | 494 |
| (5-Furan-2-yl-7-trifluoromethyl-pyrazolo[1,5-a]pyrimidin-2-yl)-(4-phenyl-piperazin-1-yl)-methanone | 441 |
| 3-Bromo-5-thiophen-2-yl-7-trifluoromethyl-pyrazolo[1,5-a]pyrimidine-2-carboxylic acid (1-phenyl-ethyl)-amide | 494 |
| (3-Bromo-5-thiophen-2-yl-7-trifluoromethyl-pyrazolo[1,5-a]pyrimidin-2-yl)-[4-(4-fluoro-phenyl)-piperazin-1-yl]-methanone | 553 |
| 5-(3,4-Dimethoxy-phenyl)-7-trifluoromethyl-pyrazolo[1,5-a]pyrimidine-2-carboxylic acid (5-chloro-2-hydroxy-phenyl)-amide | 492 |
| 5-(3,4-Dimethoxy-phenyl)-7-trifluoromethyl-pyrazolo[1,5-a]pyrimidine-2-carboxylic acid benzo[1,3]dioxol-5-ylamide | 486 |
| 5-(3,4-Dimethoxy-phenyl)-7-trifluoromethyl-pyrazolo[1,5-a]pyrimidine-2-carboxylic acid (3,4-dimethoxy-phenyl)-amide | 502 |
| 6-tert-Butyl-2-{[5-(4-methoxy-phenyl)-7-trifluoromethyl-pyrazolo[1,5-a]pyrimidine-2-carbonyl]-amino}-4,5,6,7-tetrahydro-benzo[b]thiophene-3-carboxylic acid methyl ester | 586 |
| 5-Benzo[1,3]dioxol-5-yl-7-trifluoromethyl-pyrazolo[1,5-a]pyrimidine-2-carboxylic acid (4-acetyl-phenyl)-amide | 468 |
| (5-Benzo[1,3]dioxol-5-yl-7-trifluoromethyl-pyrazolo[1,5-a]pyrimidin-2-yl)-(3,4-dihydro-2H-quinolin-1-yl)-methanone | 466 |
| 5-(3,4-Dichloro-phenyl)-7-trifluoromethyl-pyrazolo[1,5-a]pyrimidine-2-carboxylic acid (4-cyano-phenyl)-amide | 475 |
| 7-Trifluoromethyl-5,6-dihydro-7a,8,11-triaza-cyclopenta[b]phenanthrene-9-carboxylic acid (2-chloro-5-trifluoromethyl-phenyl)-amide | 510 |
| 3-Chloro-5-(4-methoxy-phenyl)-7-trifluoromethyl-pyrazolo[1,5-a]pyrimidine-2-carboxylic acid (2-methoxy-ethyl)-amide | 428 |
| 3-Chloro-5-(4-chloro-phenyl)-7-trifluoromethyl-pyrazolo[1,5-a]pyrimidine-2-carboxylic acid (3-morpholin-4-yl-propyl)-amide | 501 |
| 3-Chloro-5-(4-chloro-phenyl)-7-trifluoromethyl-pyrazolo[1,5-a]pyrimidine-2-carboxylic acid (2-methoxy-ethyl)-amide | 432 |
| 5-Phenyl-7-trifluoromethyl-pyrazolo[1,5-a]pyrimidine-2-carboxylic acid (3,5-diphenoxy-phenyl)-amide | 566 |
| 3-Chloro-5-(4-methoxy-phenyl)-7-trifluoromethyl-pyrazolo[1,5-a]pyrimidine-2-carboxylic acid (3-imidazol-1-yl-propyl)-amide | 478 |
| 3-Chloro-5-(4-fluoro-phenyl)-7-trifluoromethyl-pyrazolo[1,5-a]pyrimidine-2-carboxylic acid tert-butylamide | 414 |
| 5-p-Tolyl-7-trifluoromethyl-pyrazolo[1,5-a]pyrimidine-2-carboxylic acid sec-butylamide | 376 |
| 3-Chloro-5-phenyl-7-trifluoromethyl-pyrazolo[1,5-a]pyrimidine-2-carboxylic acid [3-nitro-5-(6,7,8,9-tetrahydro-dibenzofuran-2-yloxy)-phenyl]-amide | 647 |
| 3-Bromo-5-furan-2-yl-7-trifluoromethyl-pyrazolo[1,5-a]pyrimidine-2-carboxylic acid cyclopentylamide | 442 |
| 3-Chloro-5-furan-2-yl-7-trifluoromethyl-pyrazolo[1,5-a]pyrimidine-2-carboxylic acid isobutyl-amide | 386 |
| 5-Benzo[1,3]dioxol-5-yl-7-trifluoromethyl-pyrazolo[1,5-a]pyrimidine-2-carboxylic acid (3-trifluoromethyl-phenyl)-amide | 494 |
| (5-Benzo[1,3]dioxol-5-yl-7-trifluoromethyl-pyrazolo[1,5-a]pyrimidin-2-yl)-(4-phenyl-piperazin-1-yl)-methanone | 495 |
| [5-(4-Chloro-phenyl)-7-trifluoromethyl-pyrazolo[1,5-a]pyrimidin-2-yl]-(4-methyl-piperazin-1-yl)-methanone | 423 |
| 5-(4-Methoxy-phenyl)-7-trifluoromethyl-pyrazolo[1,5-a]pyrimidine-2-carboxylic acid (5-chloro-2-methyl-phenyl)-amide | 460 |
| 5-(4-Methoxy-phenyl)-7-trifluoromethyl-pyrazolo[1,5-a]pyrimidine-2-carboxylic acid (2,5-dimethyl-phenyl)-amide | 440 |
| 5-(4-Methoxy-phenyl)-7-trifluoromethyl-pyrazolo[1,5-a]pyrimidine-2-carboxylic acid o-tolylamide | 426 |
| 5-(4-Methoxy-phenyl)-7-trifluoromethyl-pyrazolo[1,5-a]pyrimidine-2-carboxylic acid (1-ethyl-pyrrolidin-2-ylmethyl)-amide | 447 |
| 5-p-Tolyl-7-trifluoromethyl-pyrazolo[1,5-a]pyrimidine-2-carboxylic acid indan-5-ylamide | 436 |
| 5-p-Tolyl-7-trifluoromethyl-pyrazolo[1,5-a]pyrimidine-2-carboxylic acid (3,4-dimethyl-phenyl)-amide | 424 |
| 5-p-Tolyl-7-trifluoromethyl-pyrazolo[1,5-a]pyrimidine-2-carboxylic acid (3-chloro-4-methoxy-phenyl)-amide | 460 |
| 5-p-Tolyl-7-trifluoromethyl-pyrazolo[1,5-a]pyrimidine-2-carboxylic acid benzyl-(2-hydroxy-ethyl)-amide | 454 |

-continued

| name | MZ |
|---|---|
| 5-(4-Chloro-phenyl)-7-trifluoromethyl-pyrazolo[1,5-a]pyrimidine-2-carboxylic acid indan-5-ylamide | 456 |
| 1-[5-(4-Chloro-phenyl)-7-trifluoromethyl-pyrazolo[1,5-a]pyrimidine-2-carbonyl]-piperidine-4-carboxylic acid ethyl ester | 480 |
| 4-{[5-(3,4-Dimethoxy-phenyl)-7-trifluoromethyl-pyrazolo[1,5-a]pyrimidine-2-carbonyl]-amino}-piperidine-1-carboxylic acid ethyl ester | 521 |
| 5-(3,4-Dimethoxy-phenyl)-7-trifluoromethyl-pyrazolo[1,5-a]pyrimidine-2-carboxylic acid (3,5-dimethyl-phenyl)-amide | 470 |
| 5-(3,4-Dimethoxy-phenyl)-7-trifluoromethyl-pyrazolo[1,5-a]pyrimidine-2-carboxylic acid (4-methoxy-phenyl)-amide | 472 |
| 4-(5-Benzo[1,3]dioxol-5-yl-7-trifluoromethyl-pyrazolo[1,5-a]pyrimidine-2-carbonyl)-piperazine-1-carboxylic acid ethyl ester | 491 |
| [4-(Furan-2-carbonyl)-piperazin-1-yl]-(5-thiophen-2-yl-7-trifluoromethyl-pyrazolo[1,5-a]pyrimidin-2-yl)-methanone | 475 |
| 3-Bromo-5-(4-methoxy-phenyl)-7-trifluoromethyl-pyrazolo[1,5-a]pyrimidine-2-carboxylic acid (2,4-dimethoxy-phenyl)-amide | 550 |
| 5-(4-Methoxy-phenyl)-7-trifluoromethyl-pyrazolo[1,5-a]pyrimidine-2-carboxylic acid [3-(indan-5-yloxy)-5-nitro-phenyl]-amide | 589 |
| 3-Chloro-5-phenyl-7-trifluoromethyl-pyrazolo[1,5-a]pyrimidine-2-carboxylic acid (3-cyano-5,6,7,8-tetrahydro-4H-cyclohepta[b]thiophen-2-yl)-amide | 515 |
| 2-[(3-Bromo-5-phenyl-7-trifluoromethyl-pyrazolo[1,5-a]pyrimidine-2-carbonyl)-amino]-6-tert-butyl-4,5,6,7-tetrahydro-benzo[b]thiophene-3-carboxylic acid methyl ester | 634 |
| 5-(4-Bromo-phenyl)-7-trifluoromethyl-pyrazolo[1,5-a]pyrimidine-2-carboxylic acid (furan-2-ylmethyl)-amide | 464 |
| 5-(4-Bromo-phenyl)-7-trifluoromethyl-pyrazolo[1,5-a]pyrimidine-2-carboxylic acid (furan-2-ylmethyl)-amide | 467 |
| [5-(4-Bromo-phenyl)-3-chloro-7-trifluoromethyl-pyrazolo[1,5-a]pyrimidin-2-yl]-morpholin-4-yl-methanone | 488 |
| [5-(4-Bromo-phenyl)-3-chloro-7-trifluoromethyl-pyrazolo[1,5-a]pyrimidin-2-yl]-(4-methyl-piperazin-1-yl)-methanone | 501 |
| 5-(4-Nitro-phenyl)-7-trifluoromethyl-pyrazolo[1,5-a]pyrimidine-2-carboxylic acid (3,4,5-trimethoxy-phenyl)-amide | 517 |
| 3-Bromo-5-phenyl-7-trifluoromethyl-pyrazolo[1,5-a]pyrimidine-2-carboxylic acid (4-fluoro-2-nitro-phenyl)-amide | 523 |
| 3-Bromo-5-phenyl-7-trifluoromethyl-pyrazolo[1,5-a]pyrimidine-2-carboxylic acid (thiophen-2-ylmethyl)-amide | 480 |
| 3-Chloro-5-thiophen-2-yl-7-trifluoromethyl-pyrazolo[1,5-a]pyrimidine-2-carboxylic acid (3-imidazol-1-yl-propyl)-amide | 454 |
| 3-Bromo-5-phenyl-7-trifluoromethyl-pyrazolo[1,5-a]pyrimidine-2-carboxylic acid propylamide | 426 |
| 5-Phenyl-7-trifluoromethyl-pyrazolo[1,5-a]pyrimidine-2-carboxylic acid 4-fluoro-benzylamide | 414 |
| 5-Phenyl-7-trifluoromethyl-pyrazolo[1,5-a]pyrimidine-2-carboxylic acid 4-methoxy-benzylamide | 426 |
| 3-Bromo-5-phenyl-7-trifluoromethyl-pyrazolo[1,5-a]pyrimidine-2-carboxylic acid (3-imidazol-1-yl-propyl)-amide | 492 |
| [4-(4-Fluoro-phenyl)-piperazin-1-yl]-(5-thiophen-2-yl-7-trifluoromethyl-pyrazolo[1,5-a]pyrimidin-2-yl)-methanone | 475 |
| 3-Bromo-5-thiophen-2-yl-7-trifluoromethyl-pyrazolo[1,5-a]pyrimidine-2-carboxylic acid isobutyl-amide | 446 |
| 3-Bromo-5-thiophen-2-yl-7-trifluoromethyl-pyrazolo[1,5-a]pyrimidine-2-carboxylic acid (tetrahydro-furan-2-ylmethyl)-amide | 474 |
| 3-Chloro-5-phenyl-7-trifluoromethyl-pyrazolo[1,5-a]pyrimidine-2-carboxylic acid benzylamide | 430 |
| 5-(4-Methoxy-phenyl)-7-trifluoromethyl-pyrazolo[1,5-a]pyrimidine-2-carboxylic acid butylamide | 392 |
| 5-(4-Methoxy-phenyl)-7-trifluoromethyl-pyrazolo[1,5-a]pyrimidine-2-carboxylic acid phenethyl-amide | 440 |
| 3-Bromo-5-thiophen-2-yl-7-trifluoromethyl-pyrazolo[1,5-a]pyrimidine-2-carboxylic acid (3-diethylamino-propyl)-amide | 503 |
| 5,7-Diphenyl-pyrazolo[1,5-a]pyrimidine-2-carboxylic acid benzylamide | 404 |
| 3-Chloro-5-thiophen-2-yl-7-trifluoromethyl-pyrazolo[1,5-a]pyrimidine-2-carboxylic acid benzyl-methyl-amide | 450 |
| 3-Chloro-5-thiophen-2-yl-7-trifluoromethyl-pyrazolo[1,5-a]pyrimidine-2-carboxylic acid 4-chloro-benzylamide | 470 |
| 3-Chloro-5-thiophen-2-yl-7-trifluoromethyl-pyrazolo[1,5-a]pyrimidine-2-carboxylic acid (3-morpholin-4-yl-propyl)-amide | 473 |
| 5-(4-Fluoro-phenyl)-7-trifluoromethyl-pyrazolo[1,5-a]pyrimidine-2-carboxylic acid (furan-2-ylmethyl)-amide | 404 |
| 5-(4-Fluoro-phenyl)-7-trifluoromethyl-pyrazolo[1,5-a]pyrimidine-2-carboxylic acid (tetrahydro-furan-2-ylmethyl)-amide | 408 |
| 5-Thiophen-2-yl-7-trifluoromethyl-pyrazolo[1,5-a]pyrimidine-2-carboxylic acid cyanomethyl-amide | 351 |

-continued

| name | MZ |
|---|---|
| 5-Thiophen-2-yl-7-trifluoromethyl-pyrazolo[1,5-a]pyrimidine-2-carboxylic acid cyanomethyl-amide | 591 |
| 3-Bromo-5-(4-bromo-phenyl)-7-trifluoromethyl-pyrazolo[1,5-a]pyrimidine-2-carboxylic acid (3-imidazol-1-yl-propyl)-amide | 570 |
| 5-(4-Nitro-phenyl)-7-trifluoromethyl-pyrazolo[1,5-a]pyrimidine-2-carboxylic acid benzyl-phenyl-amide | 517 |
| 3-Bromo-5-thiophen-2-yl-7-trifluoromethyl-pyrazolo[1,5-a]pyrimidine-2-carboxylic acid (3-morpholin-4-yl-propyl)-amide | 517 |
| 7-Trifluoromethyl-5,6-dihydro-7a,8,11-triaza-cyclopenta[b]phenanthrene-9-carboxylic acid methyl-(2-pyridin-2-yl-ethyl)-amide | 451 |
| 3-Chloro-5-(4-methoxy-phenyl)-7-trifluoromethyl-pyrazolo[1,5-a]pyrimidine-2-carboxylic acid (2-methylsulfanyl-phenyl)-amide | 492 |
| 3-Chloro-5-p-tolyl-7-trifluoromethyl-pyrazolo[1,5-a]pyrimidine-2-carboxylic acid (3-acetyl-phenyl)-amide | 472 |
| 7-Trifluoromethyl-5,6-dihydro-7a,8,11-triaza-cyclopenta[b]phenanthrene-9-carboxylic acid (2,6-dichloro-phenyl)-amide | 476 |
| 3,6-Dibromo-pyrazolo[1,5-a]pyrimidine-2-carboxylic acid propylamide | 360 |
| 3,6-Dibromo-pyrazolo[1,5-a]pyrimidine-2-carboxylic acid benzylamide | 408 |
| (5,7-Diphenyl-pyrazolo[1,5-a]pyrimidin-2-yl)-morpholin-4-yl-methanone | 384 |
| 3-Chloro-5-thiophen-2-yl-7-trifluoromethyl-pyrazolo[1,5-a]pyrimidine-2-carboxylic acid tert-butylamide | 402 |
| (4-Benzoyl-piperazin-1-yl)-[5-(4-bromo-phenyl)-7-trifluoromethyl-pyrazolo[1,5-a]pyrimidin-2-yl]-methanone | 557 |
| 3-Bromo-5-(4-bromo-phenyl)-7-trifluoromethyl-pyrazolo[1,5-a]pyrimidine-2-carboxylic acid isobutyl-amide | 518 |
| 3-Chloro-5-(3,4-dimethoxy-phenyl)-7-trifluoromethyl-pyrazolo[1,5-a]pyrimidine-2-carboxylic acid naphthalen-1-ylamide | 526 |
| (5-Benzo[1,3]dioxol-5-yl-7-trifluoromethyl-pyrazolo[1,5-a]pyrimidin-2-yl)-piperidin-1-yl-methanone | 418 |
| 5-Furan-2-yl-7-trifluoromethyl-pyrazolo[1,5-a]pyrimidine-2-carboxylic acid cyclohexylamide | 378 |
| 5-Furan-2-yl-7-trifluoromethyl-pyrazolo[1,5-a]pyrimidine-2-carboxylic acid (4-ethoxy-phenyl)-amide | 416 |
| (6-Fluoro-2-methyl-3,4-dihydro-2H-quinolin-1-yl)-(5-furan-2-yl-7-trifluoromethyl-pyrazolo[1,5-a]pyrimidin-2-yl)-methanone | 444 |
| 5-Furan-2-yl-7-trifluoromethyl-pyrazolo[1,5-a]pyrimidine-2-carboxylic acid (1-benzyl-1H-pyrazol-4-yl)-amide | 452 |
| Piperidin-1-yl-(5-thiophen-2-yl-7-trifluoromethyl-pyrazolo[1,5-a]pyrimidin-2-yl)-methanone | 380 |
| 3-Chloro-5-phenyl-7-trifluoromethyl-pyrazolo[1,5-a]pyrimidine-2-carboxylic acid (3-morpholin-4-yl-propyl)-amide | 467 |
| (2-Methyl-piperidin-1-yl)-(5-thiophen-2-yl-7-trifluoromethyl-pyrazolo[1,5-a]pyrimidin-2-yl)-methanone | 394 |
| 5,7-Diphenyl-pyrazolo[1,5-a]pyrimidine-2-carboxylic acid (2-morpholin-4-yl-ethyl)-amide | 427 |
| 7-Methyl-5-phenyl-pyrazolo[1,5-a]pyrimidine-2-carboxylic acid (tetrahydro-furan-2-ylmethyl)-amide | 336 |
| 5-Phenyl-7-trifluoromethyl-pyrazolo[1,5-a]pyrimidine-2-carboxylic acid (thiophen-2-ylmethyl)-amide | 402 |
| 3-Chloro-5-phenyl-7-trifluoromethyl-pyrazolo[1,5-a]pyrimidine-2-carboxylic acid (tetrahydro-furan-2-ylmethyl)-amide | 424 |
| 7-Methyl-5-phenyl-pyrazolo[1,5-a]pyrimidine-2-carboxylic acid (3-methoxy-5-nitro-phenyl)-amide | 403 |
| 3-Chloro-5-phenyl-7-trifluoromethyl-pyrazolo[1,5-a]pyrimidine-2-carboxylic acid (2-methoxy-ethyl)-amide | 398 |
| [3-Bromo-5-(4-methoxy-phenyl)-7-trifluoromethyl-pyrazolo[1,5-a]pyrimidin-2-yl]-piperidin-1-yl-methanone | 482 |
| 5-Phenyl-7-trifluoromethyl-pyrazolo[1,5-a]pyrimidine-2-carboxylic acid (3-imidazol-1-yl-propyl)-amide | 414 |
| (3-Chloro-5-furan-2-yl-7-trifluoromethyl-pyrazolo[1,5-a]pyrimidin-2-yl)-piperidin-1-yl-methanone | 398 |
| 3-Chloro-5-(3,4-dimethoxy-phenyl)-7-trifluoromethyl-pyrazolo[1,5-a]pyrimidine-2-carboxylic acid (thiophen-2-ylmethyl)-amide | 496 |
| (4-Benzyl-piperazin-1-yl)-[3-chloro-5-(4-methoxy-phenyl)-7-trifluoromethyl-pyrazolo[1,5-a]pyrimidin-2-yl]-methanone | 529 |
| (4-Benzyl-piperazin-1-yl)-(5-p-tolyl-7-trifluoromethyl-pyrazolo[1,5-a]pyrimidin-2-yl)-methanone | 479 |
| 7-Trifluoromethyl-5,6-dihydro-7a,8,11-triaza-cyclopenta[b]phenanthrene-9-carboxylic acid benzyl-methyl-amide | 436 |
| [3-Chloro-5-(4-chloro-phenyl)-7-trifluoromethyl-pyrazolo[1,5-a]pyrimidin-2-yl]-morpholin-4-yl-methanone | 444 |

-continued

| name | MZ |
|---|---|
| 5-Thiophen-2-yl-7-trifluoromethyl-pyrazolo[1,5-a]pyrimidine-2-carboxylic acid [2-(3,4-dimethoxy-phenyl)-ethyl]-amide | 476 |
| 5-(3,4-Dimethoxy-phenyl)-7-trifluoromethyl-pyrazolo[1,5-a]pyrimidine-2-carboxylic acid (thiophen-2-ylmethyl)-amide | 462 |
| 5-(4-Chloro-phenyl)-7-trifluoromethyl-pyrazolo[1,5-a]pyrimidine-2-carboxylic acid (3-methanesulfonyl-phenyl)-amide | 494 |
| 3-Chloro-5-phenyl-7-trifluoromethyl-pyrazolo[1,5-a]pyrimidine-2-carboxylic acid phenethyl-amide | 444 |
| 5-(4-Nitro-phenyl)-7-trifluoromethyl-pyrazolo[1,5-a]pyrimidine-2-carboxylic acid phenethyl-amide | 455 |
| 3-Chloro-5-furan-2-yl-7-trifluoromethyl-pyrazolo[1,5-a]pyrimidine-2-carboxylic acid benzyl-methyl-amide | 434 |
| 3-Chloro.5-furan-2-yl-7-trifluoromethyl-pyrazolo[1,5-a]pyrimidine-2-carboxylic acid benzylamide | 420 |
| 3-Bromo-5-phenyl-7-trifluoromethyl-pyrazolo[1,5-a]pyrimidine-2-carboxylic acid phenethyl-amide | 488 |
| 3-Chloro-5-furan-2-yl-7-trifluoromethyl-pyrazolo[1,5-a]pyrimidine-2-carboxylic acid methyl-(2-pyridin-2-yl-ethyl)-amide | 449 |
| 10-Chloro-7-trifluoromethyl-5,6-dihydro-7a,8,11-triaza-cyclopenta[b]phenanthrene-9-carboxylic acid methyl-(2-pyridin-2-yl-ethyl)-amide | 485 |
| 3-Bromo-5-thiophen-2-yl-7-trifluoromethyl-pyrazolo[1,5-a]pyrimidine-2-carboxylic acid 4-fluoro-benzylamide | 498 |
| 5-(3,4-Dimethoxy-phenyl)-7-trifluoromethyl-pyrazolo[1,5-a]pyrimidine-2-carboxylic acid cyclohexylamide | 448 |
| [5-(3,4-Dimethoxy-phenyl)-7-trifluoromethyl-pyrazolo[1,5-a]pyrimidin-2-yl]-(4-methyl-piperidin-1-yl)-methanone | 448 |
| 5-Benzo[1,3]dioxol-5-yl-7-trifluoromethyl-pyrazolo[1,5-a]pyrimidine-2-carboxylic acid (2-trifluoromethyl-phenyl)-amide | 494 |
| 5-Benzo[1,3]dioxol-5-yl-7-trifluoromethyl-pyrazolo[1,5-a]pyrimidine-2-carboxylic acid (3-cyano-4-ethyl-5-methyl-thiophen-2-yl)-amide | 499 |
| 4-{[5-(4-Methoxy-phenyl)-7-trifluoromethyl-pyrazolo[1,5-a]pyrimidine-2-carbonyl]-amino}-piperidine-1-carboxylic acid ethyl ester | 491 |
| 1-[5-(4-Methoxy-phenyl)-7-trifluoromethyl-pyrazolo[1,5-a]pyrimidine-2-carbonyl]-piperidine-4-carboxylic acid ethyl ester | 476 |
| 1-(5-p-Tolyl-7-trifluoromethyl-pyrazolo[1,5-a]pyrimidine-2-carbonyl)-piperidine-4-carboxylic acid ethyl ester | 460 |
| 4-(5-p-Tolyl-7-trifluoromethyl-pyrazolo[1,5-a]pyrimidine-2-carbonyl)-piperazine-1-carboxylic acid ethyl ester | 461 |
| 4-{[5-(4-Chloro-phenyl)-7-trifluoromethyl-pyrazolo[1,5-a]pyrimidine-2-carbonyl]-amino}-piperidine-1-carboxylic acid ethyl ester | 495 |
| 5-(3,4-Dimethoxy-phenyl)-7-trifluoromethyl-pyrazolo[1,5-a]pyrimidine-2-carboxylic acid (2,5-dimethyl-phenyl)-amide | 470 |
| 5-(3,4-Dimethoxy-phenyl)-7-trifluoromethyl-pyrazolo[1,5-a]pyrimidine-2-carboxylic acid (2,3-dimethyl-phenyl)-amide | 470 |
| 5-(3,4-Dimethoxy-phenyl)-7-trifluoromethyl-pyrazolo[1,5-a]pyrimidine-2-carboxylic acid (4-ethoxy-phenyl)-amide | 486 |
| 3-Bromo-5-furan-2-yl-7-trifluoromethyl-pyrazolo[1,5-a]pyrimidine-2-carboxylic acid (2-morpholin-4-yl-ethyl)-amide | 487 |
| (3-Bromo-5-furan-2-yl-7-trifluoromethyl-pyrazolo[1,5-a]pyrimidin-2-yl)-piperidin-1-yl-methanone | 442 |
| 3-Bromo-5-furan-2-yl-7-trifluoromethyl-pyrazolo[1,5-a]pyrimidine-2-carboxylic acid (4-methyl-pyridin-2-yl)-amide | 465 |
| (3-Bromo-5-furan-2-yl-7-trifluoromethyl-pyrazolo[1,5-a]pyrimidin-2-yl)-morpholin-4-yl-methanone | 444 |
| 3-Bromo-5-furan-2-yl-7-trifluoromethyl-pyrazolo[1,5-a]pyrimidine-2-carboxylic acid (3-imidazol-1-yl-propyl)-amide | 482 |
| 3-Bromo-5-furan-2-yl-7-trifluoromethyl-pyrazolo[1,5-a]pyrimidine-2-carboxylic acid propylamide | 416 |
| (3-Bromo-5-furan-2-yl-7-trifluoromethyl-pyrazolo[1,5-a]pyrimidin-2-yl)-(4-methyl-piperazin-1-yl)-methanone | 457 |
| 3-Bromo-5-phenyl-7-trifluoromethyl-pyrazolo[1,5-a]pyrimidine-2-carboxylic acid (2-hydroxy-5-methyl-phenyl)-amide | 490 |
| (3-Bromo-5-phenyl-7-trifluoromethyl-pyrazolo[1,5-a]pyrimidin-2-yl)-(hexahydro-pyrrolo[1,2-a]pyrazin-2-yl)-methanone | 493 |
| 5-tert-Butyl-7-trifluoromethyl-pyrazolo[1,5-a]pyrimidine-2-carboxylic acid (2-chloro-pyridin-3-yl)-amide | 397 |
| 5-(3,4-Dimethyl-phenyl)-7-trifluoromethyl-pyrazolo[1,5-a]pyrimidine-2-carboxylic acid (1-ethyl-5-methyl-1H-pyrazol-4-ylmethyl)-methyl-amide | 470 |
| (3-Bromo-5-phenyl-7-trifluoromethyl-pyrazolo[1,5-a]pyrimidin-2-yl)-piperidin-1-yl-methanone | 452 |
| 5-(4-Methoxy-phenyl)-7-trifluoromethyl-pyrazolo[1,5-a]pyrimidine-2-carboxylic acid (2-trifluoromethyl-phenyl)-amide | 480 |
| 3-Bromo-5-phenyl-7-trifluoromethyl-pyrazolo[1,5-a]pyrimidine-2-carboxylic acid cyclopentylamide | 452 |

-continued

| name | MZ |
|---|---|
| 3-Bromo-5-phenyl-7-trifluoromethyl-pyrazolo[1,5-a]pyrimidine-2-carboxylic acid tert-butylamide | 440 |
| 3-Bromo-5-phenyl-7-trifluoromethyl-pyrazolo[1,5-a]pyrimidine-2-carboxylic acid (furan-2-ylmethyl)-amide | 464 |
| (3-Bromo-5-phenyl-7-trifluoromethyl-pyrazolo[1,5-a]pyrimidin-2-yl)-(2-methyl-piperidin-1-yl)-methanone | 466 |
| 5-Thiophen-2-yl-7-trifluoromethyl-pyrazolo[1,5-a]pyrimidine-2-carboxylic acid (2-trifluoromethyl-phenyl)-amide | 456 |
| 3-Bromo-5-thiophen-2-yl-7-trifluoromethyl-pyrazolo[1,5-a]pyrimidine-2-carboxylic acid isopropylamide | 432 |
| (3-Bromo-5-thiophen-2-yl-7-trifluoromethyl-pyrazolo[1,5-a]pyrimidin-2-yl)-piperidin-1-yl-methanone | 458 |
| 3-Bromo-5-thiophen-2-yl-7-trifluoromethyl-pyrazolo[1,5-a]pyrimidine-2-carboxylic acid benzylamide | 480 |
| 3-Bromo-5-thiophen-2-yl-7-trifluoromethyl-pyrazolo[1,5-a]pyrimidine-2-carboxylic acid (furan-2-ylmethyl)-amide | 470 |
| 3-Bromo-5-thiophen-2-yl-7-trifluoromethyl-pyrazolo[1,5-a]pyrimidine-2-carboxylic acid pyridin-4-ylamide | 467 |
| 3-Bromo-5-thiophen-2-yl-7-trifluoromethyl-pyrazolo[1,5-a]pyrimidine-2-carboxylic acid (3-imidazol-1-yl-propyl)-amide | 498 |
| Azepan-1-yl-[5-(3,4-dimethoxy-phenyl)-7-trifluoromethyl-pyrazolo[1,5-a]pyrimidin-2-yl]-methanone | 448 |
| 5-Furan-2-yl-7-trifluoromethyl-pyrazolo[1,5-a]pyrimidine-2-carboxylic acid adamantan-1-ylamide | 430 |
| 3-Bromo-5-thiophen-2-yl-7-trifluoromethyl-pyrazolo[1,5-a]pyrimidine-2-carboxylic acid cyanomethyl-amide | 429 |
| (5-Furan-2-yl-7-trifluoromethyl-pyrazolo[1,5-a]pyrimidin-2-yl)-(1,3,3-trimethyl-6-aza-bicyclo[3.2.1]oct-6-yl)-methanone | 432 |
| [4-(3-Fluoro-benzoyl)-piperazin-1-yl]-(5-furan-2-yl-7-trifluoromethyl-pyrazolo[1,5-a]pyrimidin-2-yl)-methanone | 487 |
| 1-(5-Furan-2-yl-7-trifluoromethyl-pyrazolo[1,5-a]pyrimidine-2-carbonyl)-piperidine-4-carboxylic acid ethyl ester | 436 |
| (5-Furan-2-yl-7-trifluoromethyl-pyrazolo[1,5-a]pyrimidin-2-yl)-(2,4,6-trimethyl-piperidin-1-yl)-methanone | 406 |
| 5-Furan-2-yl-7-trifluoromethyl-pyrazolo[1,5-a]pyrimidine-2-carboxylic acid (2-acetyl-4,5-dimethoxy-phenyl)-amide | 474 |
| 5-Furan-2-yl-7-trifluoromethyl-pyrazolo[1,5-a]pyrimidine-2-carboxylic acid adamantan-1-yl-methyl-amide | 444 |
| 5-Furan-2-yl-7-trifluoromethyl-pyrazolo[1,5-a]pyrimidine-2-carboxylic acid [3,5-dimethyl-1-(2-methyl-benzyl)-1H-pyrazol-4-yl]-amide | 494 |
| 5-Furan-2-yl-7-trifluoromethyl-pyrazolo[1,5-a]pyrimidine-2-carboxylic acid [3,5-dimethyl-1-(4-methyl-benzyl)-1H-pyrazol-4-yl]-amide | 494 |
| 5-Furan-2-yl-7-trifluoromethyl-pyrazolo[1,5-a]pyrimidine-2-carboxylic acid [1-(4-fluoro-benzyl)-3,5-dimethyl-1H-pyrazol-4-yl]-amide | 498 |
| 5-[(6-Bromo-pyrazolo[1,5-a]pyrimidine-2-carbonyl)-amino]-3-methyl-thiophene-2,4-dicarboxylic acid diethyl ester | 480 |
| (4-Methyl-piperidin-1-yl)-(5-phenyl-7-trifluoromethyl-pyrazolo[1,5-a]pyrimidin-2-yl)-methanone | 388 |
| (3-Bromo-5-thiophen-2-yl-7-trifluoromethyl-pyrazolo[1,5-a]pyrimidin-2-yl)-(2,6-dimethyl-piperidin-1-yl)-methanone | 486 |
| 5-Furan-2-yl-7-trifluoromethyl-pyrazolo[1,5-a]pyrimidine-2-carboxylic acid (tetrahydro-furan-2-ylmethyl)-amide | 380 |
| 3-Chloro-5-thiophen-2-yl-7-trifluoromethyl-pyrazolo[1,5-a]pyrimidine-2-carboxylic acid (tetrahydro-furan-2-ylmethyl)-amide | 430 |

It is understood that the examples and embodiments described herein are for illustrative purposes only and that various modifications or changes in light thereof will be suggested to persons skilled in the art and are to included within the spirit and purview of this application and are considered within the scope of the appended claims.

All publications, patents, and patent applications cited herein are hereby incorporated by reference in their entirety for all purposes.

What is claimed is:

1. A method of decreasing ion flow through a voltage-dependent sodium channel in a cell, said method comprising contacting said cell with a sodium channel-inhibiting amount of a compound comprising a pyrazolopyrimidine moiety.

2. The method according to claim 1, wherein said cell is in a human.

3. The method of claim 1, wherein said pyrazolopyrimidine moiety is a pyrazolo[1,5-a]pyrimidine moiety.

4. A method of decreasing ion flow through voltage-dependent sodium channels in a cell, said method comprising contacting said cell with a sodium channel-inhibiting amount of a compound of the formula:

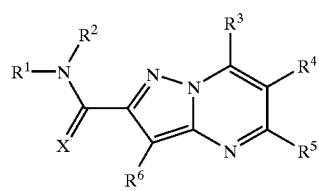

wherein
- R¹ is a member selected from substituted or unsubstituted alkyl, substituted or unsubstituted aryl, substituted or unsubstituted heteroaryl, substituted or unsubstituted heterocycloalkyl, and substituted or unsubstituted aryl (alkyl);
- R² is a member selected from hydrogen and substituted or unsubstituted alkyl; R¹ and R² taken together with the nitrogen atom to which they are optionally joined to form a 4- to 8-membered heterocycloaryl ring;
- R³ is a member selected from hydrogen, substituted or unsubstituted alkyl, halo, amino, substituted or unsubstituted aryl, substituted or unsubstituted heteroaryl and substituted or unsubstituted heterocycloalkyl;
- R⁴ is a member selected from hydrogen, halo, substituted or unsubstituted alkyl and substituted or unsubstituted aryl;
- R⁵ is a member selected from substituted or unsubstituted alkyl, substituted or unsubstituted aryl, substituted or unsubstituted heteroaryl and substituted or unsubstituted heterocycloalkyl;
- R⁶ is a member selected from hydrogen, halo, substituted or unsubstituted aryl, substituted or unsubstituted heteroaryl, and substituted or unsubstituted heterocycloalkyl; and
- X is a member selected from O and S.

5. A method of treating pain through inhibition of a voltage-dependent sodium channel, wherein said pain is selected from inflammatory pain, neuropathic pain and combinations thereof, said method comprising administering to a subject in need of such treatment, an effective amount of a compound having the formula:

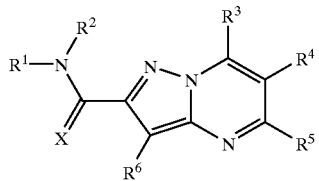

wherein
- R¹ is a member selected from substituted or unsubstituted alkyl, substituted or unsubstituted aryl, substituted or unsubstituted heteroaryl, substituted or unsubstituted heterocycloalkyl, and substituted or unsubstituted aryl (alkyl);
- R² is a member selected from hydrogen and substituted or unsubstituted alkyl; R¹ and R² taken together with the nitrogen atom to which they are optionally joined to form a 4- to 8-membered heterocycloaryl ring;
- R³ is a member selected from hydrogen, substituted or unsubstituted alkyl, halo, amino, substituted or unsubstituted aryl, substituted or unsubstituted heteroaryl and substituted or unsubstituted heterocycloalkyl;
- R⁴ is a member selected from hydrogen, halo, substituted or unsubstituted alkyl and substituted or unsubstituted aryl;
- R⁵ is a member selected from substituted or unsubstituted alkyl, substituted or unsubstituted aryl, substituted or unsubstituted heteroaryl and substituted or unsubstituted heterocycloalkyl;
- R⁶ is a member selected from hydrogen, halo, substituted or unsubstituted aryl, substituted or unsubstituted heteroaryl, and substituted or unsubstituted heterocycloalkyl; and
- X is a member selected from O and S.

6. A method of decreasing ion flow through a voltage-dependent sodium channel in a cell, wherein said cell is in a human, and said method comprises contacting said cell with a sodium channel-inhibiting amount of a compound of the formula:

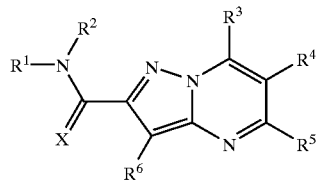

wherein
- R¹ is a member selected from substituted or unsubstituted alkyl, substituted or unsubstituted aryl, substituted or unsubstituted heteroaryl, substituted or unsubstituted heterocycloalkyl, and substituted or unsubstituted aryl (alkyl);
- R² is a member selected from hydrogen and substituted or unsubstituted alkyl; R¹ and R² taken together with the nitrogen atom to which they are optionally joined to form a 4- to 8-membered heterocycloaryl ring;
- R³ is a member selected from hydrogen, substituted or unsubstituted alkyl, halo, amino, substituted or unsubstituted aryl, substituted or unsubstituted heteroaryl and substituted or unsubstituted heterocycloalkyl;
- R⁴ is a member selected from hydrogen, halo, substituted or unsubstituted alkyl and substituted or unsubstituted aryl;
- R⁵ is a member selected from substituted or unsubstituted alkyl, substituted or unsubstituted aryl, substituted or unsubstituted heteroaryl and substituted or unsubstituted heterocycloalkyl;
- R⁶ is a member selected from hydrogen, halo, substituted or unsubstituted aryl, substituted or unsubstituted heteroaryl, and substituted or unsubstituted heterocycloalkyl; and
- X is a member selected from O and S.

7. A method of decreasing ion flow through a voltage-dependent sodium channel in a cell, said method comprising contacting said cell with a sodium channel-inhibiting amount of a composition comprising a pharmaceutically acceptable excipient and a compound having the fonnula:

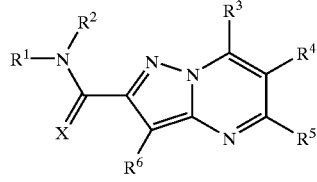

wherein
- R¹ is a member selected from substituted or unsubstituted alkyl, substituted or unsubstituted arylo, substituted or unsubstituted heteroaryl, substituted or unsubstituted heterocycloalkyl, and substituted or unsubstituted aryl (alkyl);
- R² is a member selected from hydrogen and substituted or unsubstituted alkyl; R¹ and R² taken together with the nitrogen atom to which they are optionally joined to form a 4- to 8-membered heterocycloaryl ring;

R³ is a member selected from hydrogen, substituted or unsubstituted alkyl, halo, amino, substituted or unsubstituted aryl, substituted or unsubstituted heteroaryl and substituted or unsubstituted heterocycloalkyl;

R⁴ is a member selected from hydrogen, halo, substituted or unsubstituted alkyl and substituted or unsubstituted aryl;

R⁵ is a member selected from substituted or unsubstituted alkyl, substituted or unsubstituted aryl, substituted or unsubstituted heteroaryl and substituted or unsubstituted heterocycloalkyl;

R⁶ is a member selected from hydrogen, halo, substituted or unsubstituted aryl, substituted or unsubstituted heteroaryl, and substituted or unsubstituted heterocycloalkyl; and X is a member selected from O and S.

8. A method of treating pain through inhibition of a voltage-dependent sodium channel, wherein said pain is selected from inflammatory pain, neuropathic pain and combinations thereof, said method comprising administering to a subject in need of such treatment, an effective amount of a composition comprising a pharmaceutically acceptable excipient and a compound having the formula:

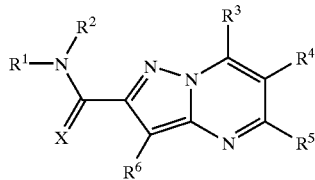

wherein

R¹ is a member selected from substituted or unsubstituted alkyl, substituted or unsubstituted aryl, substituted or unsubstituted heteroaryl, substituted or unsubstituted heterocycloalkyl, and substituted or unsubstituted aryl (alkyl);

R² is a member selected from hydrogen and substituted or unsubstituted alkyl; R¹ and R² taken together with the nitrogen atom to which they are optionally joined to form a 4- to 8-membered heterocycloaryl ring;

R³ is a member selected from hydrogen, substituted or unsubstituted alkyl, halo, amino, substituted or unsubstituted aryl, substituted or unsubstituted heteroaryl and substituted or unsubstituted heterocycloalkyl;

R⁴ is a member selected from hydrogen, halo, substituted or unsubstituted alkyl and substituted or unsubstituted aryl;

R⁵ is a member selected from substituted or unsubstituted alkyl, substituted or unsubstituted aryl, substituted or unsubstituted heteroaryl and substituted or unsubstituted heterocycloalkyl;

R⁶ is a member selected from hydrogen, halo, substituted or unsubstituted aryl, substituted or unsubstituted heteroaryl, and substituted or unsubstituted heterocycloalkyl; and X is a member selected from O and S.

* * * * *